United States Patent
Aoki et al.

(10) Patent No.: US 12,377,085 B2
(45) Date of Patent: *Aug. 5, 2025

(54) PROLONGED ECTOPARASITE-CONTROLLING AGENT FOR ANIMAL

(71) Applicant: Mitsui Chemicals Crop & Life Solutions, Inc., Tokyo (JP)

(72) Inventors: Yoji Aoki, Chiba (JP); Shinichi Banba, Chiba (JP); Markus Berger, Berlin (DE); Lars Baerfacker, Duesseldorf (DE)

(73) Assignee: Mitsui Chemicals Crop & Life Solutions, Inc., Tokyo (JP)

( * ) Notice: Subject to any disclaimer, the term of this patent is extended or adjusted under 35 U.S.C. 154(b) by 11 days.

This patent is subject to a terminal disclaimer.

(21) Appl. No.: 18/119,564

(22) Filed: Mar. 9, 2023

(65) Prior Publication Data

US 2023/0226037 A1 Jul. 20, 2023

Related U.S. Application Data

(63) Continuation of application No. 16/648,530, filed as application No. PCT/JP2018/036162 on Sep. 19, 2018, now Pat. No. 11,696,913.

(30) Foreign Application Priority Data

Sep. 20, 2017 (JP) ................................. 2017-179947

(51) Int. Cl.
  *A61K 31/455* (2006.01)
  *A61K 31/166* (2006.01)
  *A61P 33/14* (2006.01)

(52) U.S. Cl.
  CPC .......... *A61K 31/455* (2013.01); *A61K 31/166* (2013.01); *A61P 33/14* (2018.01)

(58) Field of Classification Search
  CPC .................................................. A61K 31/455
  See application file for complete search history.

(56) References Cited

U.S. PATENT DOCUMENTS

| | | | |
|---|---|---|---|
| 9,839,216 B2 | 12/2017 | Pitterna et al. | |
| 11,696,913 B2 * | 7/2023 | Aoki ...................... | A01N 37/24 514/355 |
| 2009/0099204 A1 | 4/2009 | Yoshida et al. | |
| 2011/0201687 A1 * | 8/2011 | Kobayashi ............ | C07C 237/42 564/155 |
| 2014/0343049 A1 | 11/2014 | Toueg et al. | |
| 2017/0000120 A1 | 1/2017 | Pitterna et al. | |
| 2018/0362447 A1 | 12/2018 | Takahashi et al. | |
| 2020/0181107 A1 | 6/2020 | Wu et al. | |

FOREIGN PATENT DOCUMENTS

| | | |
|---|---|---|
| CN | 102119143 A | 7/2011 |
| EP | 1916236 A1 | 4/2008 |
| EP | 2529620 A1 | 12/2012 |
| EP | 3081552 A1 | 10/2016 |
| JP | 7277445 B2 | 5/2023 |
| WO | 2005/073165 A1 | 8/2005 |
| WO | 2007/013150 A1 | 2/2007 |
| WO | 2009/080203 A2 | 7/2009 |
| WO | 2010/013567 A1 | 2/2010 |
| WO | 2010/018714 A1 | 2/2010 |
| WO | 2010/018857 A1 | 2/2010 |
| WO | 2011/093415 A1 | 8/2011 |

(Continued)

OTHER PUBLICATIONS

Australian Office Action (AUOA) dated Jun. 19, 2023 for Australian Patent Application No. 2018335796.
International Search Report (ISR) issued in PCT/JP2018/036162 mailed on Dec. 14, 2018.
Written Opinion of the ISA issued in PCT/JP2018/036162 mailed on Dec. 14, 2018.
Russian Search Report (RUSR) dated Oct. 22, 2021 for Russian Patent Application.
Chinese Office Action (CNOA) dated Aug. 14, 2023 for Chinese patent application No. 202210305455.9.

*Primary Examiner* — Nizal S Chandrakumar
(74) *Attorney, Agent, or Firm* — RANKIN, HILL & CLARK LLP

(57) ABSTRACT

A compound represented by Formula (1) can be used as a prolonged ectoparasite-controlling agent for an animal. A preparation for systemic application for use in prolonged control of an ectoparasite in an animal include the compound. A method for prolonged control of an ectoparasite on an animal includes systemically applying the compound. The compound may be used for preparing a medicament for prolonged control of an ectoparasite on an animal. A horticultural or agricultural insecticide containing the compound, and a method of protecting a crop from a harmful organism is also provided.

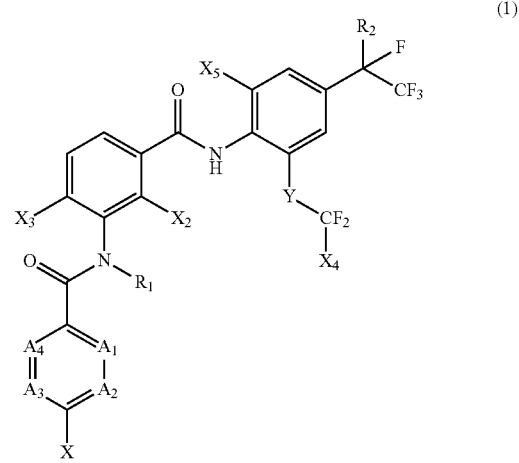

4 Claims, No Drawings

(56) References Cited

FOREIGN PATENT DOCUMENTS

| WO | 2014/161849 A1 | 10/2014 |
|----|----------------|---------|
| WO | 2015/097091 A1 | 7/2015  |
| WO | 2015/097094 A1 | 7/2015  |
| WO | 2017/104838 A1 | 6/2017  |
| WO | 2019001361 A1  | 1/2019  |
| WO | 2019012377 A1  | 1/2019  |
| WO | 2019059412 A1  | 3/2019  |

* cited by examiner

PROLONGED ECTOPARASITE-CONTROLLING AGENT FOR ANIMAL

CROSS-REFERENCE TO RELATED APPLICATIONS

This application is a continuation application of U.S. Ser. No. 16/648,530, filed on Mar. 18, 2020, which is a U.S. National Stage Entry of PCT/JP2018/036162, filed on Sep. 19, 2018, which claims priority from prior Japanese Patent Application No. 2017-179947, filed on Sep. 20, 2017. The entire contents of each of these applications are incorporated herein by reference.

TECHNICAL FIELD

The present invention relates to the use of a specific carboxamide derivative in the prolonged control of ectoparasites on animals by systemic application of said compound to said animal and to preparations for said use.

BACKGROUND ART

In WO2005/073165, WO2010/018714 and WO2011/093415 certain carboxamide derivatives and their pesticidal activities are disclosed. Methods for synthesis of such compounds as well as certain intermediates are described in WO2010/013567 and WO2010/018857. Further, pest control compositions containing carboxamide derivatives in combination with other compounds are described in WO2007/013150.

SUMMARY

Surprisingly, we have found that the compound as disclosed herein exhibits an excellent activity with respect to protection from harmful organisms. In particular, we have found that the compound has an excellent insecticidal activity, and have also found that the compound has a long-acting activity against ectoparasites upon systemic application to animals, and are therefore suitable for a prolonged control of ectoparasites on animals. Based on these findings, the present disclosure provides a prolonged ectoparasite-controlling agent for an animal, a preparation for systemic application for use in prolonged control of an ectoparasite on an animal, a method for prolonged control of an ectoparasite on an animal, use of the compound as disclosed herein for preparing a medicament for prolonged control of an ectoparasite on an animal, a horticultural or agricultural insecticide, a method of protecting a crop from a harmful organism, a composition including the compound as disclosed herein mixed with an inert carrier and an optional auxiliary agent, a mixture including the compound as disclosed herein combined with at least one other insecticide and/or fungicide, and a compound represented by a specific chemical formula.

The present invention relates to the following aspects.

[1] A prolonged ectoparasite-controlling agent for an animal represented by the following Formula (1):

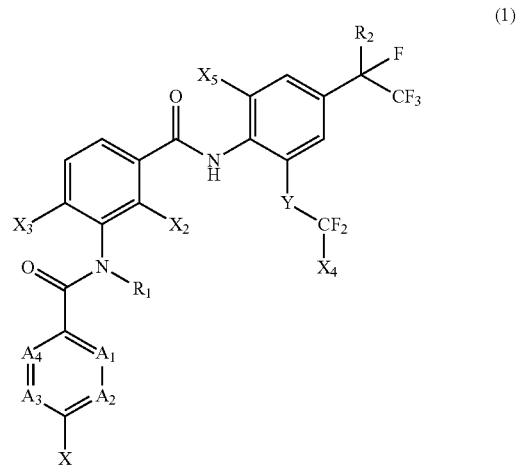

wherein
each of $A_1$, $A_2$ and $A_3$ independently represents a nitrogen atom or a C—$X_1$ group, provided that at least one of $A_1$ or $A_2$ represents a C—$X_1$ group, and provided that when $A_3$ represents a nitrogen atom, $A_1$ represents C—$X_1$ and $A_2$ represents a nitrogen atom;
$A_4$ represents a C—$X_1$ group;
$R_1$ represents a hydrogen atom or a $C_1$-$C_4$ alkyl group;
$R_2$ represents a trifluoromethyl group or a pentafluoroethyl group
X represents a halogen atom, a $C_1$-$C_4$ alkyl group, a $C_1$-$C_4$ haloalkyl group, a $C_1$-$C_4$ alkoxyl group, a $C_1$-$C_4$ haloalkoxyl, a $C_1$-$C_4$ alkylthio group, a $C_1$-$C_4$ haloalkylthio group, a $C_1$-$C_4$ alkylsulfinyl group, a $C_1$-$C_4$ haloalkylsulfinyl group, a $C_1$-$C_4$ alkylsulfonyl group, a $C_1$-$C_4$ haloalkylsulfonyl group, an aminosulfinyl group, an aminosulfonyl group, a sulfamoyl group, a nitro group or a cyano group;
each $X_1$ independently represents a hydrogen atom, a halogen atom, a $C_1$-$C_4$ alkyl group, a $C_1$-$C_4$ haloalkyl group, a $C_1$-$C_4$ alkoxyl group, a $C_1$-$C_4$ haloalkoxyl or a cyano group, provided that when X and $X_1$ are bonded to adjacent carbon atoms, X and $X_1$ together with the carbon atoms may form a five- or six-membered ring system which may be aromatic or non-aromatic, where the ring contains 0, 1, 2 or 3 hetero atoms each independently selected from N, O and S as ring members:
each of $X_2$, $X_3$ and $X_4$ independently represents a hydrogen atom or a fluorine atom;
$X_5$ represents a chlorine atom, a bromine atom or an iodine atom; and
Y represents a single bond, O, S, a sulfoxide group or a sulfonyl group.
[2] The prolonged ectoparasite-controlling agent according to [1], wherein
each of $A_1$ and $A_3$ independently represents a C—$X_1$ group;
$A_2$ represent a nitrogen atom or a C—$X_1$ group;
$A_4$ represents a C—$X_1$ group;
$R_1$ represents a hydrogen atom or a $C_1$-$C_4$ alkyl group;
$R_2$ represents a trifluoromethyl group:
X represents halogen atom or a $C_1$-$C_4$ haloalkyl group;
$X_1$ represents a hydrogen atom;
each of $X_2$ and $X_4$ represents a fluorine atom;
$X_3$ represents a hydrogen atom;

X₅ represents a bromine atom or an iodine atom; and

Y represents a single bond or a sulfonyl group.

[3] The prolonged ectoparasite-controlling agent according to [1] or [2], wherein the prolonged ectoparasite-controlling agent is systemically applied via an oral route.

[4] The prolonged ectoparasite-controlling agent according to [1] or [2], wherein the prolonged ectoparasite-controlling agent is systemically applied via a parenteral route.

[5] The prolonged ectoparasite-controlling agent according to [1] or [2], wherein the prolonged ectoparasite-controlling agent is systemically applied via a dermal route.

[6] A preparation for systemic application for use in prolonged control of an ectoparasite on an animal, the preparation including the compound represented by Formula (1).

[7] The preparation according to [6], wherein the preparation is for oral use.

[8] The preparation according to [6], wherein the preparation is for parenteral use.

[9] The preparation according to [6], wherein the preparation is for dermal use.

[10] The preparation according to any of [6] to [9], wherein the preparation is a single-dose preparation.

[11] A method for prolonged control of an ectoparasite on an animal, including systemically applying the compound represented by Formula (1).

[12] Use of the compound represented by Formula (1), for preparing a medicament for prolonged control of an ectoparasite on an animal, wherein said medicament is applied systemically to said animal.

[13] A horticultural or agricultural insecticide containing the compound represented by Formula (1) as an active ingredient.

[14] A method of protecting a crop from a harmful organism, the method including treating a crop or a soil for the crop with an effective amount of the compound represented by Formula (1).

[15] A composition including the compound represented by Formula (1) mixed with an inert carrier, and optionally with an auxiliary agent.

[16] A mixture including the compound represented by Formula (1) combined with at least one other insecticide and/or fungicide.

[17] A compound represented by the following Formula (2):

wherein

R₁ represents a hydrogen atom or a C₁-C₄ alkyl group;

R₂ represents a trifluoromethyl group or a pentafluoroethyl group;

X represents a fluorine atom, a difluoromethyl group or a trifluoromethyl group;

X₅ represents a bromine atom or iodine atom;

A represents a nitrogen atom or a C—H group; and

Y represents a single bond, O, S, a sulfoxide group or a sulfonyl group when A represents a nitrogen atom, and Y represents S, a sulfoxide group or a sulfonyl group when A represents a C—H group.

[18] The compound according to [17], wherein the compound is selected from the group consisting of N-(2-fluoro-3-((2-iodo-4-(perfluoropropan-2-yl)-6-(trifluoromethyl)phenyl)carbamoyl)phenyl)-6-(trifluoromethyl)nicotinamide, N-(2-fluoro-3-((2-iodo-4-(perfluoropropan-2-yl)-6-(trifluoromethyl)phenyl)carbamoyl)phenyl)-N-methyl-6-(trifluoromethyl)nicotinamide, 6-fluoro-N-(2-fluoro-3-((2-iodo-4-(perfluoropropan-2-yl)-6-(trifluoromethyl)phenyl)carbamoyl)phenyl)nicotinamide, 6-fluoro-N-(2-fluoro-3-((2-iodo-4-(perfluoropropan-2-yl)-6-(trifluoromethyl)phenyl)carbamoyl)phenyl)-N-methylnicotinamide, 2-fluoro-3-(4-fluoro-N-methylbenzamido)-N-(2-iodo-4-(perfluoropropan-2-yl)-6-((trifluoromethyl)sulfonyl)phenyl)benzamide, and 2-fluoro-3-(4-fluorobenzamido)-N-(2-iodo-4-(perfluoropropan-2-yl)-6-((trifluoromethyl)sulfonyl)phenyl)benzamide.

According to the present disclosure, a prolonged ectoparasite-controlling agent for an animal, a preparation for systemic application for use in prolonged control of an ectoparasite on an animal, a method for prolonged control of an ectoparasite on an animal, use of the compound as disclosed herein for preparing a medicament for prolonged control of an ectoparasite on an animal, a horticultural or agricultural insecticide, a method of protecting a crop from a harmful organism, a composition including the compound as disclosed herein mixed with an inert carrier and an optional auxiliary agent, a mixture including the compound as disclosed herein combined with at least one other insecticide and/or fungicide, and a compound represented by a specific chemical formula, can be provided.

DETAILED DESCRIPTION

In the present disclosure, a compound represented by the following Formula (1) may be used for various applications as described herein.

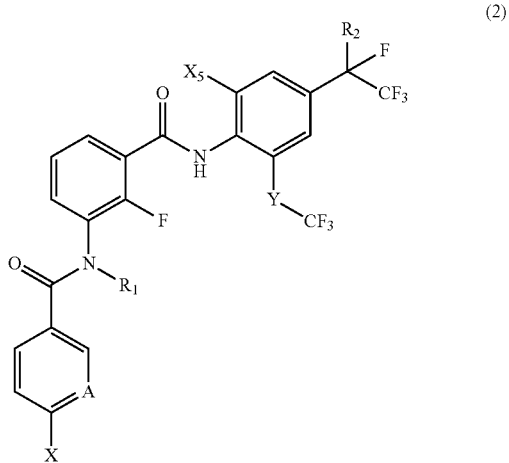

(2)

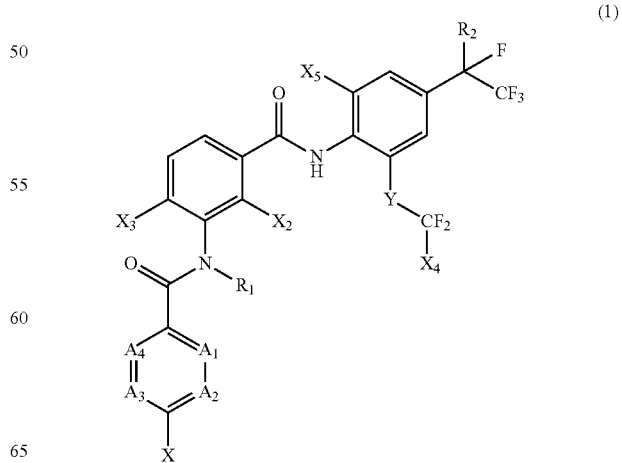

(1)

In Formula (1), each of $A_1$, $A_2$ and $A_3$ independently represents a nitrogen atom or a C—$X_1$ group, provided that at least one of $A_1$ or $A_2$ represents a C—$X_1$ group, and provided that when $A_3$ represents a nitrogen atom, $A_1$ represents C—$X_1$ and $A_2$ represents a nitrogen atom;

$A_4$ represents a C—$X_1$ group;

$R_1$ represents a hydrogen atom or a $C_1$-$C_4$ alkyl group;

$R_2$ represents a trifluoromethyl group or a pentafluoroethyl group

X represents a halogen atom, a $C_1$-$C_4$ alkyl group, a $C_1$-$C_4$ haloalkyl group, a $C_1$-$C_4$ alkoxyl group, a $C_1$-$C_4$ haloalkoxyl, a $C_1$-$C_4$ alkylthio group, a $C_1$-$C_4$ haloalkylthio group, a $C_1$-$C_4$ alkylsulfinyl group, a $C_1$-$C_4$ haloalkylsulfinyl group, a $C_1$-$C_4$ alkylsulfonyl group, a $C_1$-$C_4$ haloalkylsulfonyl group, an aminosulfinyl group, an aminosulfonyl group, a sulfamoyl group, a nitro group or a cyano group;

each $X_1$ independently represents a hydrogen atom, a halogen atom, a $C_1$-$C_4$ alkyl group, a $C_1$-$C_4$ haloalkyl group, a $C_1$-$C_4$ alkoxyl group, a $C_1$-$C_4$ haloalkoxyl or a cyano group, provided that when X and $X_1$ are bonded to adjacent carbon atoms, X and $X_1$ together with the carbon atoms may form a five- or six-membered ring system which may be aromatic or non-aromatic, where the ring contains 0, 1, 2 or 3 hetero atoms each independently selected from N, O and S as ring members;

each of $X_2$, $X_3$ and $X_4$ independently represents a hydrogen atom or a fluorine atom;

$X_5$ represents a chlorine atom, a bromine atom or an iodine atom; and

Y represents a single bond, O, S, a sulfoxide group or a sulfonyl group.

The terms used in the formulae, including Formula (1), have the meanings as described below.

As used herein, the terms "n-", "i-", "s-", and "t-" mean "normal-", "iso-", "secondary-" and "tertiary-", respectively.

The term "$C_1$-$C_4$ alkyl group" in the present invention represents, for example, a linear or branched alkyl group having from 1 to 4 carbon atoms such as methyl, ethyl, n-propyl, i-propyl, n-butyl, i-butyl, s-butyl, t-butyl.

The term "halogen atom" in the present invention represents a fluorine atom, a chlorine atom, a bromine atom, or an iodine atom.

The term "$C_1$-$C_4$ haloalkyl group" in the present invention represents, for example, a linear or branched alkyl group having from 1 to 4 carbon atoms substituted with one or more halogen atoms which may be the same as or different from each other, such as trifluoromethyl, pentafluoroethyl, heptafluoro-n-propyl, heptafluoro-i-propyl, 2,2-difluoroethyl, 2,2-dichloroethyl, 2,2,2-trifluoroethyl, 2-fluoroethyl, 2-chloroethyl, 2-bromoethyl, 2-iodoethyl, 2,2,2-trichloroethyl, 2,2,2-tribromoethyl, 1,3-difluoro-2-propyl, 1,3-dichloro-2-propyl, 1-chloro-3-fluoro-2-propyl, 1,1,1-trifluoro-2-propyl, 2,3,3,3-tetrafluoro-n-propyl, 1,1,1,3,3,3-hexafluoro-2-propyl, 1,1,1,3,3,3-hexafluoro-2-chloro-2-propyl, 1,1,1,3,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3,3-hexafluoro-1-bromo-2-propyl, 2,2,3,3,3-pentafluoro-n-propyl, 3-fluoro-n-propyl, 3-chloro-n-propyl, 3-bromo-n-propyl, nonafluoro-n-butyl, nonafluoro-i-butyl, nonafluoro-s-butyl, or nonafluoro-t-butyl. Preferably the $C_1$-$C_4$ haloalkyl group is a $C_1$-$C_4$ fluoroalkyl group, in particular a $C_1$-$C_4$ perfluoroalkyl group.

The term "$C_1$-$C_4$ alkoxy group" in the present invention represents, for example, a linear or branched alkoxy group having from 1 to 4 carbon atoms, such as methoxy, ethoxy, n-propoxy, i-propoxy, n-butoxy, i-butoxy, s-butoxy or t-butoxy.

The term "$C_1$-$C_4$ haloalkoxy group" in the present invention represents, for example, a linear or branched alkoxy group having from 1 to 4 carbon atoms substituted with one or more halogen atoms which may be the same as or different from each other, such as difluoromethoxy, trifluoromethoxy, pentafluoroethoxy, heptafluoro-n-propoxy, heptafluoro-i-propoxy, 2,2-difluoroethoxy, 2,2-dichloroethoxy, 2,2,2-trifluoroethoxy, 2-fluoroethoxy, 2-chloroethoxy, 2-bromoethoxy, 2-iodoethoxy, 2,2,2-trichloroethoxy, 2,2,2-tribromoethoxy, 1,3-difluoro-2-propoxy, 1,3-dichloro-2-propoxy, 1-chloro-3-fluoro-2-propoxy, 1,1,1-trifluoro-2-propoxy, 2,3,3,3-tetrafluoro-n-propoxy, 1,1,1,3,3,3-hexafluoro-2-propoxy, 1,1,1,3,3,3-hexafluoro-2-chloro-2-propoxy, 1,1,1,3,3,3-hexafluoro-2-bromo-2-propoxy, 1,1,2,3,3,3-hexafluoro-2-chloro-n-propoxy, 1,1,2,3,3,3-hexafluoro-2-bromo-n-propoxy, 1,1,2,3,3,3-hexafluoro-1-bromo-2-propoxy, 2,2,3,3,3-pentafluoro-n-propoxy, 3-fluoro-n-propoxy, 3-chloro-n-propoxy, 3-bromo-n-propoxy, nonafluoro-n-butoxy, nonafluoro-i-butoxy, nonafluoro-s-butoxy, or nonafluoro-t-butoxy. Preferably the $C_1$-$C_4$ haloalkoxy group is a $C_1$-$C_4$ fluoroalkoxy group, in particular a $C_1$-$C_4$ perfluoroalkoxy group.

The term "$C_1$-$C_4$ alkylthio group" in the present invention represents, for example, a linear or branched alkylthio group having from 1 to 4 carbon atoms, such as methylthio, ethylthio, n-propylthio, i-propylthio, n-butylthio, i-butylthio, s-butylthio, or t-butylthio.

The term "$C_1$-$C_4$ haloalkylthio group" in the present invention represents, for example, a linear or branched alkylthio group having from 1 to 4 carbon atom substituted with one or more halogen atoms which may be the same as or different from each other, such as difluoromethylthio, trifluoromethylthio, pentafluoroethylthio, heptafluoro-n-propylthio, heptafluoro-i-propylthio, 2,2-difluoroethylthio, 2,2-dichloroethylthio, 2,2,2-trifluoroethylthio, 2-fluoroethylthio, 2-chloroethylthio, 2-bromoethylthio, 2-iodoethylthio, 2,2,2-trichloroethylthio, 2,2,2-tribromoethylthio, 1,3-difluoro-2-propylthio, 1,3-dichloro-2-propylthio, 1-chloro-3-fluoro-2-propylthio, 1,1,1-trifluoro-2-propylthio, 2,3,3,3-tetrafluoro-n-propylthio, 1,1,1,3,3,3-hexafluoro-2-propylthio, 1,1,1,3,3,3-hexafluoro-2-chloro-2-propylthio, 1,1,1,3,3,3-hexafluoro-2-bromo-2-propylthio, 1,1,2,3,3,3-hexafluoro-2-chloro-n-propylthio, 1,1,2,3,3,3-hexafluoro-2-bromo-n-propylthio, 1,1,2,3,3,3-hexafluoro-1-bromo-2-propylthio, 2,2,3,3,3-pentafluoro-n-propylthio, 3-fluoro-n-propylthio, 3-chloro-n-propylthio, 3-bromo-n-propylthio, nonafluoro-n-butylthio, nonafluoro-i-butylthio, nonafluoro-s-butylthio, or nonafluoro-t-butylthio. Preferably the $C_1$-$C_4$ haloalkylthio group is a $C_1$-$C_4$ fluoroalkylthio group, in particular a $C_1$-$C_4$ perfluoroalkylthio group.

The term "$C_1$-$C_4$ alkylsulfinyl group" in the present invention represents, for example, a linear or branched alkylsulfinyl group having from 1 to 4 carbon atoms, such as methylsulfinyl, ethylsulfinyl, n-propylsulfinyl, i-propylsulfinyl, n-butylsulfinyl, i-butylsulfinyl, s-butylsulfinyl, or t-butylsulfinyl.

The term "$C_1$-$C_4$ haloalkylsulfinyl group" in the present invention represents, for example, a linear or branched alkylsulfinyl group having from 1 to 4 carbon atom substituted with one or more halogen atoms which may be the same as or different from each other, such as difluoromethylsulfinyl, trifluoromethylsulfinyl, pentafluoroethylsulfinyl, heptafluoro-n-propylsulfinyl, heptafluoro-i-propylsulfinyl, 2,2-difluoroethylsulfinyl, 2,2-dichloroethylsulfinyl, 2,2,2- trifluoroethylsulfinyl, 2-fluoroethylsulfinyl, 2-chloroethylsulfinyl, 2-bromoethylsulfinyl, 2-iodoethylsulfinyl, 2,2,2-trichloroethylsulfinyl, 2,2,2-tribromoethylsulfinyl, 1,3-difluoro-2-propylsulfinyl, 1,3-dichloro-2-propylsulfinyl, 1-chloro-3-fluoro-2-propylsulfinyl, 1,1,1-trifluoro-2-propylsulfinyl, 2,3,3,3-tetrafluoro-n-propylsulfinyl, 1,1,1,3,3,3-hexafluoro-2-propylsulfinyl, 1,1,1,3,3,3-hexafluoro-2-chloro-2-propylsulfinyl, 1,1,1,3,3,3-hexafluoro-2-bromo-2-propylsulfinyl, 1,1,2,3,3,3-hexafluoro-2-chloro-n-propylsulfinyl, 1,1,2,3,3,3-hexafluoro-2-bromo-n-propylsulfinyl, 1,1,2,3,3,3-hexafluoro-1-bromo-2-propylsulfinyl, 2,2,3,3,3-pentafluoro-n-propylsulfinyl, 3-fluoro-n-propylsulfinyl, 3-chloro-n-propylsulfinyl, 3-bromo-n-propylsulfinyl, nonafluoro-n-butylsulfinyl, nonafluoro-i-butylsulfinyl, nonafluoro-s-butylsulfinyl, or nonafluoro-t-butylsulfinyl. Preferably the $C_1$-$C_4$ haloalkylsulfinyl group is a $C_1$-$C_4$ fluoroalkylsulfinyl group, in particular a $C_1$-$C_4$ perfluoroalkylsulfinyl group.

The term "$C_1$-$C_4$ alkylsulfonyl group" in the present invention represents, for example, a linear or branched alkylsulfonyl group having from 1 to 4 carbon atoms, such as methylsulfonyl, ethylsulfonyl, n-propylsulfonyl, i-propylsulfonyl, n-butylsulfonyl, i-butylsulfonyl, s-butylsulfonyl, t-butylsulfonyl or the like.

The term "$C_1$-$C_4$ haloalkylsulfonyl group" in the present invention represents, for example, a linear or branched alkylsulfonyl group having from 1 to 4 carbon atom substituted with one or more halogen atoms which may be the same as or different from each other, such as difluoromethylsulfonyl, trifluoromethylsulfonyl, pentafluoroethylsulfonyl, heptafluoro-n-propylsulfonyl, heptafluoro-i-propylsulfonyl, 2,2-difluoroethylsulfonyl, 2,2-dichloroethylsulfonyl, 2,2,2-trifluoroethylsulfonyl, 2-fluoroethylsulfonyl, 2-chloroethylsulfonyl, 2-bromoethylsulfonyl, 2-iodoethylsulfonyl, 2,2,2-trichloroethylsulfonyl, 2,2,2-tribromoethylsulfonyl, 1,3-difluoro-2-propylsulfonyl, 1,3-dichloro-2-propylsulfonyl, 1-chloro-3-fluoro-2-propylsulfonyl, 1,1,1-trifluoro-2-propylsulfonyl, 2,3,3,3-tetrafluoro-n-propylsulfonyl, 1,1,1,3,3,3-hexafluoro-2-propylsulfonyl, 1,1,1,3,3,3-hexafluoro-2-chloro-2-propylsulfonyl, 1,1,1,3,3,3-hexafluoro-2-bromo-2-propylsulfonyl, 1,1,2,3,3,3-hexafluoro-2-chloro-n-propylsulfonyl, 1,1,2,3,3,3-hexafluoro-2-bromo-n-propylsulfonyl, 1,1,2,3,3,3-hexafluoro-1-bromo-2-propylsulfonyl, 2,2,3,3,3-pentafluoro-n-propylsulfonyl, 3-fluoro-n-propylsulfonyl, 3-chloro-n-propylsulfonyl, 3-bromo-n-propylsulfonyl, nonafluoro-n-butylsulfonyl, nonafluoro-i-butylsulfonyl, nonafluoro-s-butylsulfonyl, or nonafluoro-t-butylsulfonyl. Preferably the $C_1$-$C_4$ haloalkylsulfonyl group is a $C_1$-$C_4$ fluoroalkylsulfonyl group, in particular a $C_1$-$C_4$ perfluoroalkylsulfonyl group.

The compound represented by Formula (1) according to the present invention may include one or plural chiral carbon atoms or chiral centers in its structural formulae, and thus two or more optical isomers (enantiomers or diastereomers) may exist. However, the scope of the present invention includes each of the optical isomers and mixtures thereof at any proportions.

In Formula (1) preferable definitions of substituents include the following: Preferably, X represents a fluorine atom or a trifluoromethyl group. Preferably, $R_1$ represents a hydrogen atom or a methyl group. Preferably, $X_1$ represents a hydrogen atom or a fluorine atom.

In an embodiment, the compound represented by Formula (1) is a compound in which each of $A_1$ and $A_3$ independently represents a C—$X_1$ group, $A_2$ represent a nitrogen atom or a C—$X_1$ group, $A_4$ represents a C—$X_1$ group, $R_1$ represents a hydrogen atom or a $C_1$-$C_4$ alkyl group, $R_2$ represents a trifluoromethyl group: X represents halogen atom or a $C_1$-$C_4$ haloalkyl group, $X_1$ represents a hydrogen atom, each of $X_2$ and $X_4$ represents a fluorine atom, $X_3$ represents a hydrogen atom, $X_5$ represents a bromine atom or an iodine atom, and Y represents a single bond or a sulfonyl group.

Examples of the compound represented by Formula (1) which can be used in the present invention include the compounds listed in Table 1. The compounds listed in Table 1 is represented by the following Formula (Formula (1)) in which $R_1$ is $CH_3$, $R_2$ is $CF_3$, $X_2$ is F, $X_3$ is H, $X_4$ is F, $X_5$ is I, Y is single bond, and $A_1$, $A_2$, $A_3$, $A_4$ and X are as indicated in Table 1.

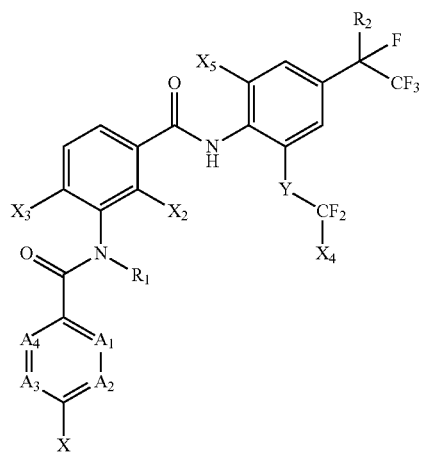

TABLE 1

| $A_1$ | $A_2$ | $A_3$ | $A_4$ | X |
|---|---|---|---|---|
| CH | CH | CH | CH | F |
| CH | CH | CH | CH | Cl |
| CH | CH | CH | CH | Br |
| CH | CH | CH | CH | I |
| CH | CH | CH | CH | $CH_3$ |
| CH | CH | CH | CH | $CH_2CH_3$ |
| CH | CH | CH | CH | $CF_3$ |
| CH | CH | CH | CH | $CHF_2$ |
| CH | CH | CH | CH | $CF_2CF_3$ |
| CH | CH | CH | CH | $CF(CF_3)_2$ |
| CH | CH | CH | CH | $OCH_3$ |
| CH | CH | CH | CH | $OCH_2CH_3$ |
| CH | CH | CH | CH | $OCF_3$ |
| CH | CH | CH | CH | $OCHF_2$ |
| CH | CH | CH | CH | $SCH_3$ |
| CH | CH | CH | CH | $SCH_2CH_3$ |
| CH | CH | CH | CH | $SCF_3$ |
| CH | CH | CH | CH | $SOCH_3$ |
| CH | CH | CH | CH | $SOCH_2CH_3$ |
| CH | CH | CH | CH | $SOCF_3$ |
| CH | CH | CH | CH | $SO_2CH_3$ |
| CH | CH | CH | CH | $SO_2CH_2CH_3$ |
| CH | CH | CH | CH | $SO_2CF_3$ |
| CH | CH | CH | CH | $SO_2NH_2$ |
| CH | CH | CH | CH | $NO_2$ |
| CH | CH | CH | CH | —CN |
| CF | CH | CH | CH | F |
| CF | CH | CH | CH | Cl |
| CF | CH | CH | CH | Br |
| CF | CH | CH | CH | I |
| CF | CH | CH | CH | $CH_3$ |
| CF | CH | CH | CH | $CH_2CH_3$ |
| CF | CH | CH | CH | $CF_3$ |
| CF | CH | CH | CH | $CHF_2$ |
| CF | CH | CH | CH | $CF_2CF_3$ |

TABLE 1-continued

| A₁ | A₂ | A₃ | A₄ | X |
|---|---|---|---|---|
| CF | CH | CH | CH | CF(CF₃)₂ |
| CF | CH | CH | CH | OCH₃ |
| CF | CH | CH | CH | OCH₂CH₃ |
| CF | CH | CH | CH | OCF₃ |
| CF | CH | CH | CH | OCHF₂ |
| CF | CH | CH | CH | SCH₃ |
| CF | CH | CH | CH | SCH₂CH₃ |
| CF | CH | CH | CH | SCF₃ |
| CF | CH | CH | CH | SOCH₃ |
| CF | CH | CH | CH | SOCH₂CH₃ |
| CF | CH | CH | CH | SOCF₃ |
| CF | CH | CH | CH | SO₂CH₃ |
| CF | CH | CH | CH | SO₂CH₂CH₃ |
| CF | CH | CH | CH | SO₂CF₃ |
| CF | CH | CH | CH | SO₂NH₂ |
| CF | CH | CH | CH | NO₂ |
| CF | CH | CH | CH | —CN |
| CH | CF | CH | CH | F |
| CH | CF | CH | CH | Cl |
| CH | CF | CH | CH | Br |
| CH | CF | CH | CH | I |
| CH | CF | CH | CH | CH₃ |
| CH | CF | CH | CH | CH₂CH₃ |
| CH | CF | CH | CH | CF₃ |
| CH | CF | CH | CH | CHF₂ |
| CH | CF | CH | CH | CF₂CF₃ |
| CH | CF | CH | CH | CF(CF₃)₂ |
| CH | CF | CH | CH | OCH₃ |
| CH | CF | CH | CH | OCH₂CH₃ |
| CH | CF | CH | CH | OCF₃ |
| CH | CF | CH | CH | OCHF₂ |
| CH | CF | CH | CH | SCH₃ |
| CH | CF | CH | CH | SCH₂CH₃ |
| CH | CF | CH | CH | SCF₃ |
| CH | CF | CH | CH | SOCH₃ |
| CH | CF | CH | CH | SOCH₂CH₃ |
| CH | CF | CH | CH | SOCF₃ |
| CH | CF | CH | CH | SO₂CH₃ |
| CH | CF | CH | CH | SO₂CH₂CH₃ |
| CH | CF | CH | CH | SO₂CF₃ |
| CH | CF | CH | CH | SO₂NH₂ |
| CH | CF | CH | CH | NO₂ |
| CH | CF | CH | CH | —CN |
| CCl | CH | CH | CH | F |
| CCl | CH | CH | CH | Cl |
| CCl | CH | CH | CH | Br |
| CCl | CH | CH | CH | I |
| CCl | CH | CH | CH | CH₃ |
| CCl | CH | CH | CH | CH₂CH₃ |
| CCl | CH | CH | CH | CF₃ |
| CCl | CH | CH | CH | CHF₂ |
| CCl | CH | CH | CH | CF₂CF₃ |
| CCl | CH | CH | CH | CF(CF₃)₂ |
| CCl | CH | CH | CH | OCH₃ |
| CCl | CH | CH | CH | OCH₂CH₃ |
| CCl | CH | CH | CH | OCF₃ |
| CCl | CH | CH | CH | OCHF₂ |
| CCl | CH | CH | CH | SCH₃ |
| CCl | CH | CH | CH | SCH₂CH₃ |
| CCl | CH | CH | CH | SCF₃ |
| CCl | CH | CH | CH | SOCH₃ |
| CCl | CH | CH | CH | SOCH₂CH₃ |
| CCl | CH | CH | CH | SOCF₃ |
| CCl | CH | CH | CH | SO₂CH₃ |
| CCl | CH | CH | CH | SO₂CH₂CH₃ |
| CCl | CH | CH | CH | SO₂CF₃ |
| CCl | CH | CH | CH | SO₂NH₂ |
| CCl | CH | CH | CH | NO₂ |
| CCl | CH | CH | CH | —CN |
| CH | CCl | CH | CH | F |
| CH | CCl | CH | CH | Cl |
| CH | CCl | CH | CH | Br |
| CH | CCl | CH | CH | I |
| CH | CCl | CH | CH | CH₃ |
| CH | CCl | CH | CH | CH₂CH₃ |
| CH | CCl | CH | CH | CF₃ |
| CH | CCl | CH | CH | CHF₂ |
| CH | CCl | CH | CH | CF₂CF₃ |
| CH | CCl | CH | CH | CF(CF₃)₂ |
| CH | CCl | CH | CH | OCH₃ |
| CH | CCl | CH | CH | OCH₂CH₃ |
| CH | CCl | CH | CH | OCF₃ |
| CH | CCl | CH | CH | OCHF₂ |
| CH | CCl | CH | CH | SCH₃ |
| CH | CCl | CH | CH | SCH₂CH₃ |
| CH | CCl | CH | CH | SCF₃ |
| CH | CCl | CH | CH | SOCH₃ |
| CH | CCl | CH | CH | SOCH₂CH₃ |
| CH | CCl | CH | CH | SOCF₃ |
| CH | CCl | CH | CH | SO₂CH₃ |
| CH | CCl | CH | CH | SO₂CH₂CH₃ |
| CH | CCl | CH | CH | SO₂CF₃ |
| CH | CCl | CH | CH | SO₂NH₂ |
| CH | CCl | CH | CH | NO₂ |
| CH | CCl | CH | CH | —CN |
| CCH₃ | CH | CH | CH | F |
| CCH₃ | CH | CH | CH | Cl |
| CCH₃ | CH | CH | CH | Br |
| CCH₃ | CH | CH | CH | I |
| CCH₃ | CH | CH | CH | CH₃ |
| CCH₃ | CH | CH | CH | CH₂CH₃ |
| CCH₃ | CH | CH | CH | CF₃ |
| CCH₃ | CH | CH | CH | CHF₂ |
| CCH₃ | CH | CH | CH | CF₂CF₃ |
| CCH₃ | CH | CH | CH | CF(CF₃)₂ |
| CCH₃ | CH | CH | CH | OCH₃ |
| CCH₃ | CH | CH | CH | OCH₂CH₃ |
| CCH₃ | CH | CH | CH | OCF₃ |
| CCH₃ | CH | CH | CH | OCHF₂ |
| CCH₃ | CH | CH | CH | SCH₃ |
| CCH₃ | CH | CH | CH | SCH₂CH₃ |
| CCH₃ | CH | CH | CH | SCF₃ |
| CCH₃ | CH | CH | CH | SOCH₃ |
| CCH₃ | CH | CH | CH | SOCH₂CH₃ |
| CCH₃ | CH | CH | CH | SOCF₃ |
| CCH₃ | CH | CH | CH | SO₂CH₃ |
| CCH₃ | CH | CH | CH | SO₂CH₂CH₃ |
| CCH₃ | CH | CH | CH | SO₂CF₃ |
| CCH₃ | CH | CH | CH | SO₂NH₂ |
| CCH₃ | CH | CH | CH | NO₂ |
| CCH₃ | CH | CH | CH | —CN |
| CH | CCH₃ | CH | CH | F |
| CH | CCH₃ | CH | CH | Cl |
| CH | CCH₃ | CH | CH | Br |
| CH | CCH₃ | CH | CH | I |
| CH | CCH₃ | CH | CH | CH₃ |
| CH | CCH₃ | CH | CH | CH₂CH₃ |
| CH | CCH₃ | CH | CH | CF₃ |
| CH | CCH₃ | CH | CH | CHF₂ |
| CH | CCH₃ | CH | CH | CF₂CF₃ |
| CH | CCH₃ | CH | CH | CF(CF₃)₂ |
| CH | CCH₃ | CH | CH | OCH₃ |
| CH | CCH₃ | CH | CH | OCH₂CH₃ |
| CH | CCH₃ | CH | CH | OCF₃ |
| CH | CCH₃ | CH | CH | OCHF₂ |
| CH | CCH₃ | CH | CH | SCH₃ |
| CH | CCH₃ | CH | CH | SCH₂CH₃ |
| CH | CCH₃ | CH | CH | SCF₃ |
| CH | CCH₃ | CH | CH | SOCH₃ |
| CH | CCH₃ | CH | CH | SOCH₂CH₃ |
| CH | CCH₃ | CH | CH | SOCF₃ |
| CH | CCH₃ | CH | CH | SO₂CH₃ |
| CH | CCH₃ | CH | CH | SO₂CH₂CH₃ |
| CH | CCH₃ | CH | CH | SO₂CF₃ |
| CH | CCH₃ | CH | CH | SO₂NH₂ |
| CH | CCH₃ | CH | CH | NO₂ |
| CH | CCH₃ | CH | CH | —CN |
| CCF₃ | CH | CH | CH | F |
| CCF₃ | CH | CH | CH | Cl |
| CCF₃ | CH | CH | CH | Br |
| CCF₃ | CH | CH | CH | I |
| CCF₃ | CH | CH | CH | CH₃ |
| CCF₃ | CH | CH | CH | CH₂CH₃ |
| CCF₃ | CH | CH | CH | CF₃ |
| CCF₃ | CH | CH | CH | CHF₂ |
| CCF₃ | CH | CH | CH | CF₂CF₃ |

TABLE 1-continued

| A₁ | A₂ | A₃ | A₄ | X |
|---|---|---|---|---|
| CCF₃ | CH | CH | CH | CF(CF₃)₂ |
| CCF₃ | CH | CH | CH | OCH₃ |
| CCF₃ | CH | CH | CH | OCH₂CH₃ |
| CCF₃ | CH | CH | CH | OCF₃ |
| CCF₃ | CH | CH | CH | OCHF₂ |
| CCF₃ | CH | CH | CH | SCH₃ |
| CCF₃ | CH | CH | CH | SCH₂CH₃ |
| CCF₃ | CH | CH | CH | SCF₃ |
| CCF₃ | CH | CH | CH | SOCH₃ |
| CCF₃ | CH | CH | CH | SOCH₂CH₃ |
| CCF₃ | CH | CH | CH | SOCF₃ |
| CCF₃ | CH | CH | CH | SO₂CH₃ |
| CCF₃ | CH | CH | CH | SO₂CH₂CH₃ |
| CCF₃ | CH | CH | CH | SO₂CF₃ |
| CCF₃ | CH | CH | CH | SO₂NH₂ |
| CCF₃ | CH | CH | CH | NO₂ |
| CCF₃ | CH | CH | CH | —CN |
| CH | CCF₃ | CH | CH | F |
| CH | CCF₃ | CH | CH | Cl |
| CH | CCF₃ | CH | CH | Br |
| CH | CCF₃ | CH | CH | I |
| CH | CCF₃ | CH | CH | CH₃ |
| CH | CCF₃ | CH | CH | CH₂CH₃ |
| CH | CCF₃ | CH | CH | CF₃ |
| CH | CCF₃ | CH | CH | CHF₂ |
| CH | CCF₃ | CH | CH | CF₂CF₃ |
| CH | CCF₃ | CH | CH | CF(CF₃)₂ |
| CH | CCF₃ | CH | CH | OCH₃ |
| CH | CCF₃ | CH | CH | OCH₂CH₃ |
| CH | CCF₃ | CH | CH | OCF₃ |
| CH | CCF₃ | CH | CH | OCHF₂ |
| CH | CCF₃ | CH | CH | SCH₃ |
| CH | CCF₃ | CH | CH | SCH₂CH₃ |
| CH | CCF₃ | CH | CH | SCF₃ |
| CH | CCF₃ | CH | CH | SOCH₃ |
| CH | CCF₃ | CH | CH | SOCH₂CH₃ |
| CH | CCF₃ | CH | CH | SOCF₃ |
| CH | CCF₃ | CH | CH | SO₂CH₃ |
| CH | CCF₃ | CH | CH | SO₂CH₂CH₃ |
| CH | CCF₃ | CH | CH | SO₂CF₃ |
| CH | CCF₃ | CH | CH | SO₂NH₂ |
| CH | CCF₃ | CH | CH | NO₂ |
| CH | CCF₃ | CH | CH | —CN |
| CH | N | N | CH | F |
| CH | N | N | CH | Cl |
| CH | N | N | CH | Br |
| CH | N | N | CH | I |
| CH | N | N | CH | CH₃ |
| CH | N | N | CH | CH₂CH₃ |
| CH | N | N | CH | CF₃ |
| CH | N | N | CH | CHF₂ |
| CH | N | N | CH | CF₂CF₃ |
| CH | N | N | CH | CF(CF₃)₂ |
| CH | N | N | CH | OCH₃ |
| CH | N | N | CH | OCH₂CH₃ |
| CH | N | N | CH | OCF₃ |
| CH | N | N | CH | OCHF₂ |
| CH | N | N | CH | SCH₃ |
| CH | N | N | CH | SCH₂CH₃ |
| CH | N | N | CH | SCF₃ |
| CH | N | N | CH | SOCH₃ |
| CH | N | N | CH | SOCH₂CH₃ |
| CH | N | N | CH | SOCF₃ |
| CH | N | N | CH | SO₂CH₃ |
| CH | N | N | CH | SO₂CH₂CH₃ |
| CH | N | N | CH | SO₂CF₃ |
| CH | N | N | CH | SO₂NH₂ |
| CH | N | N | CH | NO₂ |
| CH | N | N | CH | —CN |
| CF | N | N | CH | F |
| CF | N | N | CH | Cl |
| CF | N | N | CH | Br |
| CF | N | N | CH | I |
| CF | N | N | CH | CH₃ |
| CF | N | N | CH | CH₂CH₃ |
| CF | N | N | CH | CF₃ |
| CF | N | N | CH | CHF₂ |
| CF | N | N | CH | CF₂CF₃ |
| CF | N | N | CH | CF(CF₃)₂ |
| CF | N | N | CH | OCH₃ |
| CF | N | N | CH | OCH₂CH₃ |
| CF | N | N | CH | OCF₃ |
| CF | N | N | CH | OCHF₂ |
| CF | N | N | CH | SCH₃ |
| CF | N | N | CH | SCH₂CH₃ |
| CF | N | N | CH | SCF₃ |
| CF | N | N | CH | SOCH₃ |
| CF | N | N | CH | SOCH₂CH₃ |
| CF | N | N | CH | SOCF₃ |
| CF | N | N | CH | SO₂CH₃ |
| CF | N | N | CH | SO₂CH₂CH₃ |
| CF | N | N | CH | SO₂CF₃ |
| CF | N | N | CH | SO₂NH₂ |
| CF | N | N | CH | NO₂ |
| CF | N | N | CH | —CN |
| CCl | N | N | CH | F |
| CCl | N | N | CH | Cl |
| CCl | N | N | CH | Br |
| CCl | N | N | CH | I |
| CCl | N | N | CH | CH₃ |
| CCl | N | N | CH | CH₂CH₃ |
| CCl | N | N | CH | CF₃ |
| CCl | N | N | CH | CHF₂ |
| CCl | N | N | CH | CF₂CF₃ |
| CCl | N | N | CH | CF(CF₃)₂ |
| CCl | N | N | CH | OCH₃ |
| CCl | N | N | CH | OCH₂CH₃ |
| CCl | N | N | CH | OCF₃ |
| CCl | N | N | CH | OCHF₂ |
| CCl | N | N | CH | SCH₃ |
| CCl | N | N | CH | SCH₂CH₃ |
| CCl | N | N | CH | SCF₃ |
| CCl | N | N | CH | SOCH₃ |
| CCl | N | N | CH | SOCH₂CH₃ |
| CCl | N | N | CH | SOCF₃ |
| CCl | N | N | CH | SO₂CH₃ |
| CCl | N | N | CH | SO₂CH₂CH₃ |
| CCl | N | N | CH | SO₂CF₃ |
| CCl | N | N | CH | SO₂NH₂ |
| CCl | N | N | CH | NO₂ |
| CCl | N | N | CH | —CN |
| CCH₃ | N | N | CH | F |
| CCH₃ | N | N | CH | Cl |
| CCH₃ | N | N | CH | Br |
| CCH₃ | N | N | CH | I |
| CCH₃ | N | N | CH | CH₃ |
| CCH₃ | N | N | CH | CH₂CH₃ |
| CCH₃ | N | N | CH | CF₃ |
| CCH₃ | N | N | CH | CHF₂ |
| CCH₃ | N | N | CH | CF₂CF₃ |
| CCH₃ | N | N | CH | CF(CF₃)₂ |
| CCH₃ | N | N | CH | OCH₃ |
| CCH₃ | N | N | CH | OCH₂CH₃ |
| CCH₃ | N | N | CH | OCF₃ |
| CCH₃ | N | N | CH | OCHF₂ |
| CCH₃ | N | N | CH | SCH₃ |
| CCH₃ | N | N | CH | SCH₂CH₃ |
| CCH₃ | N | N | CH | SCF₃ |
| CCH₃ | N | N | CH | SOCH₃ |
| CCH₃ | N | N | CH | SOCH₂CH₃ |
| CCH₃ | N | N | CH | SOCF₃ |
| CCH₃ | N | N | CH | SO₂CH₃ |
| CCH₃ | N | N | CH | SO₂CH₂CH₃ |
| CCH₃ | N | N | CH | SO₂CF₃ |
| CCH₃ | N | N | CH | SO₂NH₂ |
| CCH₃ | N | N | CH | NO₂ |
| CCH₃ | N | N | CH | —CN |
| CCF₃ | N | N | CH | F |
| CCF₃ | N | N | CH | Cl |
| CCF₃ | N | N | CH | Br |
| CCF₃ | N | N | CH | I |
| CCF₃ | N | N | CH | CH₃ |
| CCF₃ | N | N | CH | CH₂CH₃ |
| CCF₃ | N | N | CH | CF₃ |
| CCF₃ | N | N | CH | CHF₂ |
| CCF₃ | N | N | CH | CF₂CF₃ |

TABLE 1-continued

| A₁ | A₂ | A₃ | A₄ | X |
|---|---|---|---|---|
| CCF₃ | N | N | CH | CF(CF₃)₂ |
| CCF₃ | N | N | CH | OCH₃ |
| CCF₃ | N | N | CH | OCH₂CH₃ |
| CCF₃ | N | N | CH | OCF₃ |
| CCF₃ | N | N | CH | OCHF₂ |
| CCF₃ | N | N | CH | SCH₃ |
| CCF₃ | N | N | CH | SCH₂CH₃ |
| CCF₃ | N | N | CH | SCF₃ |
| CCF₃ | N | N | CH | SOCH₃ |
| CCF₃ | N | N | CH | SOCH₂CH₃ |
| CCF₃ | N | N | CH | SOCF₃ |
| CCF₃ | N | N | CH | SO₂CH₃ |
| CCF₃ | N | N | CH | SO₂CH₂CH₃ |
| CCF₃ | N | N | CH | SO₂CF₃ |
| CCF₃ | N | N | CH | SO₂NH₂ |
| CCF₃ | N | N | CH | NO₂ |
| CCF₃ | N | N | CH | —CN |
| N | CH | CH | CH | F |
| N | CH | CH | CH | Cl |
| N | CH | CH | CH | Br |
| N | CH | CH | CH | I |
| N | CH | CH | CH | CH₃ |
| N | CH | CH | CH | CH₂CH₃ |
| N | CH | CH | CH | CF₃ |
| N | CH | CH | CH | CHF₂ |
| N | CH | CH | CH | CF₂CF₃ |
| N | CH | CH | CH | CF(CF₃)₂ |
| N | CH | CH | CH | OCH₃ |
| N | CH | CH | CH | OCH₂CH₃ |
| N | CH | CH | CH | OCF₃ |
| N | CH | CH | CH | OCHF₂ |
| N | CH | CH | CH | SCH₃ |
| N | CH | CH | CH | SCH₂CH₃ |
| N | CH | CH | CH | SCF₃ |
| N | CH | CH | CH | SOCH₃ |
| N | CH | CH | CH | SOCH₂CH₃ |
| N | CH | CH | CH | SOCF₃ |
| N | CH | CH | CH | SO₂CH₃ |
| N | CH | CH | CH | SO₂CH₂CH₃ |
| N | CH | CH | CH | SO₂CF₃ |
| N | CH | CH | CH | SO₂NH₂ |
| N | CH | CH | CH | NO₂ |
| N | CH | CH | CH | —CN |
| N | CF | CH | CH | F |
| N | CF | CH | CH | Cl |
| N | CF | CH | CH | Br |
| N | CF | CH | CH | I |
| N | CF | CH | CH | CH₃ |
| N | CF | CH | CH | CH₂CH₃ |
| N | CF | CH | CH | CF₃ |
| N | CF | CH | CH | CHF₂ |
| N | CF | CH | CH | CF₂CF₃ |
| N | CF | CH | CH | CF(CF₃)₂ |
| N | CF | CH | CH | OCH₃ |
| N | CF | CH | CH | OCH₂CH₃ |
| N | CF | CH | CH | OCF₃ |
| N | CF | CH | CH | OCHF₂ |
| N | CF | CH | CH | SCH₃ |
| N | CF | CH | CH | SCH₂CH₃ |
| N | CF | CH | CH | SCF₃ |
| N | CF | CH | CH | SOCH₃ |
| N | CF | CH | CH | SOCH₂CH₃ |
| N | CF | CH | CH | SOCF₃ |
| N | CF | CH | CH | SO₂CH₃ |
| N | CF | CH | CH | SO₂CH₂CH₃ |
| N | CF | CH | CH | SO₂CF₃ |
| N | CF | CH | CH | SO₂NH₂ |
| N | CF | CH | CH | NO₂ |
| N | CF | CH | CH | —CN |
| N | CH | CF | CH | F |
| N | CH | CF | CH | Cl |
| N | CH | CF | CH | Br |
| N | CH | CF | CH | I |
| N | CH | CF | CH | CH₃ |
| N | CH | CF | CH | CH₂CH₃ |
| N | CH | CF | CH | CF₃ |
| N | CH | CF | CH | CHF₂ |
| N | CH | CF | CH | CF₂CF₃ |
| N | CH | CF | CH | CF(CF₃)₂ |
| N | CH | CF | CH | OCH₃ |
| N | CH | CF | CH | OCH₂CH₃ |
| N | CH | CF | CH | OCF₃ |
| N | CH | CF | CH | OCHF₂ |
| N | CH | CF | CH | SCH₃ |
| N | CH | CF | CH | SCH₂CH₃ |
| N | CH | CF | CH | SCF₃ |
| N | CH | CF | CH | SOCH₃ |
| N | CH | CF | CH | SOCH₂CH₃ |
| N | CH | CF | CH | SOCF₃ |
| N | CH | CF | CH | SO₂CH₃ |
| N | CH | CF | CH | SO₂CH₂CH₃ |
| N | CH | CF | CH | SO₂CF₃ |
| N | CH | CF | CH | SO₂NH₂ |
| N | CH | CF | CH | NO₂ |
| N | CH | CF | CH | —CN |
| N | CH | CH | CF | F |
| N | CH | CH | CF | Cl |
| N | CH | CH | CF | Br |
| N | CH | CH | CF | I |
| N | CH | CH | CF | CH₃ |
| N | CH | CH | CF | CH₂CH₃ |
| N | CH | CH | CF | CF₃ |
| N | CH | CH | CF | CHF₂ |
| N | CH | CH | CF | CF₂CF₃ |
| N | CH | CH | CF | CF(CF₃)₂ |
| N | CH | CH | CF | OCH₃ |
| N | CH | CH | CF | OCH₂CH₃ |
| N | CH | CH | CF | OCF₃ |
| N | CH | CH | CF | OCHF₂ |
| N | CH | CH | CF | SCH₃ |
| N | CH | CH | CF | SCH₂CH₃ |
| N | CH | CH | CF | SCF₃ |
| N | CH | CH | CF | SOCH₃ |
| N | CH | CH | CF | SOCH₂CH₃ |
| N | CH | CH | CF | SOCF₃ |
| N | CH | CH | CF | SO₂CH₃ |
| N | CH | CH | CF | SO₂CH₂CH₃ |
| N | CH | CH | CF | SO₂CF₃ |
| N | CH | CH | CF | SO₂NH₂ |
| N | CH | CH | CF | NO₂ |
| N | CH | CH | CF | —CN |
| N | CCl | CH | CH | F |
| N | CCl | CH | CH | Cl |
| N | CCl | CH | CH | Br |
| N | CCl | CH | CH | I |
| N | CCl | CH | CH | CH₃ |
| N | CCl | CH | CH | CH₂CH₃ |
| N | CCl | CH | CH | CF₃ |
| N | CCl | CH | CH | CHF₂ |
| N | CCl | CH | CH | CF₂CF₃ |
| N | CCl | CH | CH | CF(CF₃)₂ |
| N | CCl | CH | CH | OCH₃ |
| N | CCl | CH | CH | OCH₂CH₃ |
| N | CCl | CH | CH | OCF₃ |
| N | CCl | CH | CH | OCHF₂ |
| N | CCl | CH | CH | SCH₃ |
| N | CCl | CH | CH | SCH₂CH₃ |
| N | CCl | CH | CH | SCF₃ |
| N | CCl | CH | CH | SOCH₃ |
| N | CCl | CH | CH | SOCH₂CH₃ |
| N | CCl | CH | CH | SOCF₃ |
| N | CCl | CH | CH | SO₂CH₃ |
| N | CCl | CH | CH | SO₂CH₂CH₃ |
| N | CCl | CH | CH | SO₂CF₃ |
| N | CCl | CH | CH | SO₂NH₂ |
| N | CCl | CH | CH | NO₂ |
| N | CCl | CH | CH | —CN |
| N | CH | CCl | CH | F |
| N | CH | CCl | CH | Cl |
| N | CH | CCl | CH | Br |
| N | CH | CCl | CH | I |
| N | CH | CCl | CH | CH₃ |
| N | CH | CCl | CH | CH₂CH₃ |
| N | CH | CCl | CH | CF₃ |
| N | CH | CCl | CH | CHF₂ |
| N | CH | CCl | CH | CF₂CF₃ |

TABLE 1-continued

| A₁ | A₂ | A₃ | A₄ | X |
|---|---|---|---|---|
| N | CH | CCl | CH | CF(CF₃)₂ |
| N | CH | CCl | CH | OCH₃ |
| N | CH | CCl | CH | OCH₂CH₃ |
| N | CH | CCl | CH | OCF₃ |
| N | CH | CCl | CH | OCHF₂ |
| N | CH | CCl | CH | SCH₃ |
| N | CH | CCl | CH | SCH₂CH₃ |
| N | CH | CCl | CH | SCF₃ |
| N | CH | CCl | CH | SOCH₃ |
| N | CH | CCl | CH | SOCH₂CH₃ |
| N | CH | CCl | CH | SOCF₃ |
| N | CH | CCl | CH | SO₂CH₃ |
| N | CH | CCl | CH | SO₂CH₂CH₃ |
| N | CH | CCl | CH | SO₂CF₃ |
| N | CH | CCl | CH | SO₂NH₂ |
| N | CH | CCl | CH | NO₂ |
| N | CH | CCl | CH | —CN |
| N | CH | CH | CCl | F |
| N | CH | CH | CCl | Cl |
| N | CH | CH | CCl | Br |
| N | CH | CH | CCl | I |
| N | CH | CH | CCl | CH₃ |
| N | CH | CH | CCl | CH₂CH₃ |
| N | CH | CH | CCl | CF₃ |
| N | CH | CH | CCl | CHF₂ |
| N | CH | CH | CCl | CF₂CF₃ |
| N | CH | CH | CCl | CF(CF₃)₂ |
| N | CH | CH | CCl | OCH₃ |
| N | CH | CH | CCl | OCH₂CH₃ |
| N | CH | CH | CCl | OCF₃ |
| N | CH | CH | CCl | OCHF₂ |
| N | CH | CH | CCl | SCH₃ |
| N | CH | CH | CCl | SCH₂CH₃ |
| N | CH | CH | CCl | SCF₃ |
| N | CH | CH | CCl | SOCH₃ |
| N | CH | CH | CCl | SOCH₂CH₃ |
| N | CH | CH | CCl | SOCF₃ |
| N | CH | CH | CCl | SO₂CH₃ |
| N | CH | CH | CCl | SO₂CH₂CH₃ |
| N | CH | CH | CCl | SO₂CF₃ |
| N | CH | CH | CCl | SO₂NH₂ |
| N | CH | CH | CCl | NO₂ |
| N | CH | CH | CCl | —CN |
| N | CCH₃ | CH | CH | F |
| N | CCH₃ | CH | CH | Cl |
| N | CCH₃ | CH | CH | Br |
| N | CCH₃ | CH | CH | I |
| N | CCH₃ | CH | CH | CH₃ |
| N | CCH₃ | CH | CH | CH₂CH₃ |
| N | CCH₃ | CH | CH | CF₃ |
| N | CCH₃ | CH | CH | CHF₂ |
| N | CCH₃ | CH | CH | CF₂CF₃ |
| N | CCH₃ | CH | CH | CF(CF₃)₂ |
| N | CCH₃ | CH | CH | OCH₃ |
| N | CCH₃ | CH | CH | OCH₂CH₃ |
| N | CCH₃ | CH | CH | OCF₃ |
| N | CCH₃ | CH | CH | OCHF₂ |
| N | CCH₃ | CH | CH | SCH₃ |
| N | CCH₃ | CH | CH | SCH₂CH₃ |
| N | CCH₃ | CH | CH | SCF₃ |
| N | CCH₃ | CH | CH | SOCH₃ |
| N | CCH₃ | CH | CH | SOCH₂CH₃ |
| N | CCH₃ | CH | CH | SOCF₃ |
| N | CCH₃ | CH | CH | SO₂CH₃ |
| N | CCH₃ | CH | CH | SO₂CH₂CH₃ |
| N | CCH₃ | CH | CH | SO₂CF₃ |
| N | CCH₃ | CH | CH | SO₂NH₂ |
| N | CCH₃ | CH | CH | NO₂ |
| N | CCH₃ | CH | CH | —CN |
| N | CH | CCH₃ | CH | F |
| N | CH | CCH₃ | CH | Cl |
| N | CH | CCH₃ | CH | Br |
| N | CH | CCH₃ | CH | I |
| N | CH | CCH₃ | CH | CH₃ |
| N | CH | CCH₃ | CH | CH₂CH₃ |
| N | CH | CCH₃ | CH | CF₃ |
| N | CH | CCH₃ | CH | CHF₂ |
| N | CH | CCH₃ | CH | CF₂CF₃ |
| N | CH | CCH₃ | CH | CF(CF₃)₂ |
| N | CH | CCH₃ | CH | OCH₃ |
| N | CH | CCH₃ | CH | OCH₂CH₃ |
| N | CH | CCH₃ | CH | OCF₃ |
| N | CH | CCH₃ | CH | OCHF₂ |
| N | CH | CCH₃ | CH | SCH₃ |
| N | CH | CCH₃ | CH | SCH₂CH₃ |
| N | CH | CCH₃ | CH | SCF₃ |
| N | CH | CCH₃ | CH | SOCH₃ |
| N | CH | CCH₃ | CH | SOCH₂CH₃ |
| N | CH | CCH₃ | CH | SOCF₃ |
| N | CH | CCH₃ | CH | SO₂CH₃ |
| N | CH | CCH₃ | CH | SO₂CH₂CH₃ |
| N | CH | CCH₃ | CH | SO₂CF₃ |
| N | CH | CCH₃ | CH | SO₂NH₂ |
| N | CH | CCH₃ | CH | NO₂ |
| N | CH | CCH₃ | CH | —CN |
| N | CH | CH | CCH₃ | F |
| N | CH | CH | CCH₃ | Cl |
| N | CH | CH | CCH₃ | Br |
| N | CH | CH | CCH₃ | I |
| N | CH | CH | CCH₃ | CH₃ |
| N | CH | CH | CCH₃ | CH₂CH₃ |
| N | CH | CH | CCH₃ | CF₃ |
| N | CH | CH | CCH₃ | CHF₂ |
| N | CH | CH | CCH₃ | CF₂CF₃ |
| N | CH | CH | CCH₃ | CF(CF₃)₂ |
| N | CH | CH | CCH₃ | OCH₃ |
| N | CH | CH | CCH₃ | OCH₂CH₃ |
| N | CH | CH | CCH₃ | OCF₃ |
| N | CH | CH | CCH₃ | OCHF₂ |
| N | CH | CH | CCH₃ | SCH₃ |
| N | CH | CH | CCH₃ | SCH₂CH₃ |
| N | CH | CH | CCH₃ | SCF₃ |
| N | CH | CH | CCH₃ | SOCH₃ |
| N | CH | CH | CCH₃ | SOCH₂CH₃ |
| N | CH | CH | CCH₃ | SOCF₃ |
| N | CH | CH | CCH₃ | SO₂CH₃ |
| N | CH | CH | CCH₃ | SO₂CH₂CH₃ |
| N | CH | CH | CCH₃ | SO₂CF₃ |
| N | CH | CH | CCH₃ | SO₂NH₂ |
| N | CH | CH | CCH₃ | NO₂ |
| N | CH | CH | CCH₃ | —CN |
| N | CCF₃ | CH | CH | F |
| N | CCF₃ | CH | CH | Cl |
| N | CCF₃ | CH | CH | Br |
| N | CCF₃ | CH | CH | I |
| N | CCF₃ | CH | CH | CH₃ |
| N | CCF₃ | CH | CH | CH₂CH₃ |
| N | CCF₃ | CH | CH | CF₃ |
| N | CCF₃ | CH | CH | CHF₂ |
| N | CCF₃ | CH | CH | CF₂CF₃ |
| N | CCF₃ | CH | CH | CF(CF₃)₂ |
| N | CCF₃ | CH | CH | OCH₃ |
| N | CCF₃ | CH | CH | OCH₂CH₃ |
| N | CCF₃ | CH | CH | OCF₃ |
| N | CCF₃ | CH | CH | OCHF₂ |
| N | CCF₃ | CH | CH | SCH₃ |
| N | CCF₃ | CH | CH | SCH₂CH₃ |
| N | CCF₃ | CH | CH | SCF₃ |
| N | CCF₃ | CH | CH | SOCH₃ |
| N | CCF₃ | CH | CH | SOCH₂CH₃ |
| N | CCF₃ | CH | CH | SOCF₃ |
| N | CCF₃ | CH | CH | SO₂CH₃ |
| N | CCF₃ | CH | CH | SO₂CH₂CH₃ |
| N | CCF₃ | CH | CH | SO₂CF₃ |
| N | CCF₃ | CH | CH | SO₂NH₂ |
| N | CCF₃ | CH | CH | NO₂ |
| N | CCF₃ | CH | CH | —CN |
| N | CH | CCF₃ | CH | F |
| N | CH | CCF₃ | CH | Cl |
| N | CH | CCF₃ | CH | Br |
| N | CH | CCF₃ | CH | I |
| N | CH | CCF₃ | CH | CH₃ |
| N | CH | CCF₃ | CH | CH₂CH₃ |
| N | CH | CCF₃ | CH | CF₃ |
| N | CH | CCF₃ | CH | CHF₂ |
| N | CH | CCF₃ | CH | CF₂CF₃ |

TABLE 1-continued

| A₁ | A₂ | A₃ | A₄ | X |
|---|---|---|---|---|
| N | CH | CCF₃ | CH | CF(CF₃)₂ |
| N | CH | CCF₃ | CH | OCH₃ |
| N | CH | CCF₃ | CH | OCH₂CH₃ |
| N | CH | CCF₃ | CH | OCF₃ |
| N | CH | CCF₃ | CH | OCHF₂ |
| N | CH | CCF₃ | CH | SCH₃ |
| N | CH | CCF₃ | CH | SCH₂CH₃ |
| N | CH | CCF₃ | CH | SCF₃ |
| N | CH | CCF₃ | CH | SOCH₃ |
| N | CH | CCF₃ | CH | SOCH₂CH₃ |
| N | CH | CCF₃ | CH | SOCF₃ |
| N | CH | CCF₃ | CH | SO₂CH₃ |
| N | CH | CCF₃ | CH | SO₂CH₂CH₃ |
| N | CH | CCF₃ | CH | SO₂CF₃ |
| N | CH | CCF₃ | CH | SO₂NH₂ |
| N | CH | CCF₃ | CH | NO₂ |
| N | CH | CCF₃ | CH | —CN |
| N | CH | CH | CCF₃ | F |
| N | CH | CH | CCF₃ | Cl |
| N | CH | CH | CCF₃ | Br |
| N | CH | CH | CCF₃ | I |
| N | CH | CH | CCF₃ | CH₃ |
| N | CH | CH | CCF₃ | CH₂CH₃ |
| N | CH | CH | CCF₃ | CF₃ |
| N | CH | CH | CCF₃ | CHF₂ |
| N | CH | CH | CCF₃ | CF₂CF₃ |
| N | CH | CH | CCF₃ | CF(CF₃)₂ |
| N | CH | CH | CCF₃ | OCH₃ |
| N | CH | CH | CCF₃ | OCH₂CH₃ |
| N | CH | CH | CCF₃ | OCF₃ |
| N | CH | CH | CCF₃ | OCHF₂ |
| N | CH | CH | CCF₃ | SCH₃ |
| N | CH | CH | CCF₃ | SCH₂CH₃ |
| N | CH | CH | CCF₃ | SCF₃ |
| N | CH | CH | CCF₃ | SOCH₃ |
| N | CH | CH | CCF₃ | SOCH₂CH₃ |
| N | CH | CH | CCF₃ | SOCF₃ |
| N | CH | CH | CCF₃ | SO₂CH₃ |
| N | CH | CH | CCF₃ | SO₂CH₂CH₃ |
| N | CH | CH | CCF₃ | SO₂CF₃ |
| N | CH | CH | CCF₃ | SO₂NH₂ |
| N | CH | CH | CCF₃ | NO₂ |
| N | CH | CH | CCF₃ | —CN |
| CH | N | CH | CH | F |
| CH | N | CH | CH | Cl |
| CH | N | CH | CH | Br |
| CH | N | CH | CH | I |
| CH | N | CH | CH | CH₃ |
| CH | N | CH | CH | CH₂CH₃ |
| CH | N | CH | CH | CF₃ |
| CH | N | CH | CH | CHF₂ |
| CH | N | CH | CH | CF₂CF₃ |
| CH | N | CH | CH | CF(CF₃)₂ |
| CH | N | CH | CH | OCH₃ |
| CH | N | CH | CH | OCH₂CH₃ |
| CH | N | CH | CH | OCF₃ |
| CH | N | CH | CH | OCHF₂ |
| CH | N | CH | CH | SCH₃ |
| CH | N | CH | CH | SCH₂CH₃ |
| CH | N | CH | CH | SCF₃ |
| CH | N | CH | CH | SOCH₃ |
| CH | N | CH | CH | SOCH₂CH₃ |
| CH | N | CH | CH | SOCF₃ |
| CH | N | CH | CH | SO₂CH₃ |
| CH | N | CH | CH | SO₂CH₂CH₃ |
| CH | N | CH | CH | SO₂CF₃ |
| CH | N | CH | CH | SO₂NH₂ |
| CH | N | CH | CH | NO₂ |
| CH | N | CH | CH | —CN |
| CF | N | CH | CH | F |
| CF | N | CH | CH | Cl |
| CF | N | CH | CH | Br |
| CF | N | CH | CH | I |
| CF | N | CH | CH | CH₃ |
| CF | N | CH | CH | CH₂CH₃ |
| CF | N | CH | CH | CF₃ |
| CF | N | CH | CH | CHF₂ |
| CF | N | CH | CH | CF₂CF₃ |
| CF | N | CH | CH | CF(CF₃)₂ |
| CF | N | CH | CH | OCH₃ |
| CF | N | CH | CH | OCH₂CH₃ |
| CF | N | CH | CH | OCF₃ |
| CF | N | CH | CH | OCHF₂ |
| CF | N | CH | CH | SCH₃ |
| CF | N | CH | CH | SCH₂CH₃ |
| CF | N | CH | CH | SCF₃ |
| CF | N | CH | CH | SOCH₃ |
| CF | N | CH | CH | SOCH₂CH₃ |
| CF | N | CH | CH | SOCF₃ |
| CF | N | CH | CH | SO₂CH₃ |
| CF | N | CH | CH | SO₂CH₂CH₃ |
| CF | N | CH | CH | SO₂CF₃ |
| CF | N | CH | CH | SO₂NH₂ |
| CF | N | CH | CH | NO₂ |
| CF | N | CH | CH | —CN |
| CH | N | CF | CH | F |
| CH | N | CF | CH | Cl |
| CH | N | CF | CH | Br |
| CH | N | CF | CH | I |
| CH | N | CF | CH | CH₃ |
| CH | N | CF | CH | CH₂CH₃ |
| CH | N | CF | CH | CF₃ |
| CH | N | CF | CH | CHF₂ |
| CH | N | CF | CH | CF₂CF₃ |
| CH | N | CF | CH | CF(CF₃)₂ |
| CH | N | CF | CH | OCH₃ |
| CH | N | CF | CH | OCH₂CH₃ |
| CH | N | CF | CH | OCF₃ |
| CH | N | CF | CH | OCHF₂ |
| CH | N | CF | CH | SCH₃ |
| CH | N | CF | CH | SCH₂CH₃ |
| CH | N | CF | CH | SCF₃ |
| CH | N | CF | CH | SOCH₃ |
| CH | N | CF | CH | SOCH₂CH₃ |
| CH | N | CF | CH | SOCF₃ |
| CH | N | CF | CH | SO₂CH₃ |
| CH | N | CF | CH | SO₂CH₂CH₃ |
| CH | N | CF | CH | SO₂CF₃ |
| CH | N | CF | CH | SO₂NH₂ |
| CH | N | CF | CH | NO₂ |
| CH | N | CF | CH | —CN |
| CH | N | CH | CF | F |
| CH | N | CH | CF | Cl |
| CH | N | CH | CF | Br |
| CH | N | CH | CF | I |
| CH | N | CH | CF | CH₃ |
| CH | N | CH | CF | CH₂CH₃ |
| CH | N | CH | CF | CF₃ |
| CH | N | CH | CF | CHF₂ |
| CH | N | CH | CF | CF₂CF₃ |
| CH | N | CH | CF | CF(CF₃)₂ |
| CH | N | CH | CF | OCH₃ |
| CH | N | CH | CF | OCH₂CH₃ |
| CH | N | CH | CF | OCF₃ |
| CH | N | CH | CF | OCHF₂ |
| CH | N | CH | CF | SCH₃ |
| CH | N | CH | CF | SCH₂CH₃ |
| CH | N | CH | CF | SCF₃ |
| CH | N | CH | CF | SOCH₃ |
| CH | N | CH | CF | SOCH₂CH₃ |
| CH | N | CH | CF | SOCF₃ |
| CH | N | CH | CF | SO₂CH₃ |
| CH | N | CH | CF | SO₂CH₂CH₃ |
| CH | N | CH | CF | SO₂CF₃ |
| CH | N | CH | CF | SO₂NH₂ |
| CH | N | CH | CF | NO₂ |
| CH | N | CH | CF | —CN |
| CCl | N | CH | CH | F |
| CCl | N | CH | CH | Cl |
| CCl | N | CH | CH | Br |
| CCl | N | CH | CH | I |
| CCl | N | CH | CH | CH₃ |
| CCl | N | CH | CH | CH₂CH₃ |
| CCl | N | CH | CH | CF₃ |
| CCl | N | CH | CH | CHF₂ |
| CCl | N | CH | CH | CF₂CF₃ |

TABLE 1-continued

| A₁ | A₂ | A₃ | A₄ | X |
|---|---|---|---|---|
| CCl | N | CH | CH | CF(CF₃)₂ |
| CCl | N | CH | CH | OCH₃ |
| CCl | N | CH | CH | OCH₂CH₃ |
| CCl | N | CH | CH | OCF₃ |
| CCl | N | CH | CH | OCHF₂ |
| CCl | N | CH | CH | SCH₃ |
| CCl | N | CH | CH | SCH₂CH₃ |
| CCl | N | CH | CH | SCF₃ |
| CCl | N | CH | CH | SOCH₃ |
| CCl | N | CH | CH | SOCH₂CH₃ |
| CCl | N | CH | CH | SOCF₃ |
| CCl | N | CH | CH | SO₂CH₃ |
| CCl | N | CH | CH | SO₂CH₂CH₃ |
| CCl | N | CH | CH | SO₂CF₃ |
| CCl | N | CH | CH | SO₂NH₂ |
| CCl | N | CH | CH | NO₂ |
| CCl | N | CH | CH | —CN |
| CH | N | CCl | CH | F |
| CH | N | CCl | CH | Cl |
| CH | N | CCl | CH | Br |
| CH | N | CCl | CH | I |
| CH | N | CCl | CH | CH₃ |
| CH | N | CCl | CH | CH₂CH₃ |
| CH | N | CCl | CH | CF₃ |
| CH | N | CCl | CH | CHF₂ |
| CH | N | CCl | CH | CF₂CF₃ |
| CH | N | CCl | CH | CF(CF₃)₂ |
| CH | N | CCl | CH | OCH₃ |
| CH | N | CCl | CH | OCH₂CH₃ |
| CH | N | CCl | CH | OCF₃ |
| CH | N | CCl | CH | OCHF₂ |
| CH | N | CCl | CH | SCH₃ |
| CH | N | CCl | CH | SCH₂CH₃ |
| CH | N | CCl | CH | SCF₃ |
| CH | N | CCl | CH | SOCH₃ |
| CH | N | CCl | CH | SOCH₂CH₃ |
| CH | N | CCl | CH | SOCF₃ |
| CH | N | CCl | CH | SO₂CH₃ |
| CH | N | CCl | CH | SO₂CH₂CH₃ |
| CH | N | CCl | CH | SO₂CF₃ |
| CH | N | CCl | CH | SO₂NH₂ |
| CH | N | CCl | CH | NO₂ |
| CH | N | CCl | CH | —CN |
| CH | N | CH | CCl | F |
| CH | N | CH | CCl | Cl |
| CH | N | CH | CCl | Br |
| CH | N | CH | CCl | I |
| CH | N | CH | CCl | CH₃ |
| CH | N | CH | CCl | CH₂CH₃ |
| CH | N | CH | CCl | CF₃ |
| CH | N | CH | CCl | CHF₂ |
| CH | N | CH | CCl | CF₂CF₃ |
| CH | N | CH | CCl | CF(CF₃)₂ |
| CH | N | CH | CCl | OCH₃ |
| CH | N | CH | CCl | OCH₂CH₃ |
| CH | N | CH | CCl | OCF₃ |
| CH | N | CH | CCl | OCHF₂ |
| CH | N | CH | CCl | SCH₃ |
| CH | N | CH | CCl | SCH₂CH₃ |
| CH | N | CH | CCl | SCF₃ |
| CH | N | CH | CCl | SOCH₃ |
| CH | N | CH | CCl | SOCH₂CH₃ |
| CH | N | CH | CCl | SOCF₃ |
| CH | N | CH | CCl | SO₂CH₃ |
| CH | N | CH | CCl | SO₂CH₂CH₃ |
| CH | N | CH | CCl | SO₂CF₃ |
| CH | N | CH | CCl | SO₂NH₂ |
| CH | N | CH | CCl | NO₂ |
| CH | N | CH | CCl | —CN |
| CCH₃ | N | CH | CH | F |
| CCH₃ | N | CH | CH | Cl |
| CCH₃ | N | CH | CH | Br |
| CCH₃ | N | CH | CH | I |
| CCH₃ | N | CH | CH | CH₃ |
| CCH₃ | N | CH | CH | CH₂CH₃ |
| CCH₃ | N | CH | CH | CF₃ |
| CCH₃ | N | CH | CH | CHF₂ |
| CCH₃ | N | CH | CH | CF₂CF₃ |
| CCH₃ | N | CH | CH | CF(CF₃)₂ |
| CCH₃ | N | CH | CH | OCH₃ |
| CCH₃ | N | CH | CH | OCH₂CH₃ |
| CCH₃ | N | CH | CH | OCF₃ |
| CCH₃ | N | CH | CH | OCHF₂ |
| CCH₃ | N | CH | CH | SCH₃ |
| CCH₃ | N | CH | CH | SCH₂CH₃ |
| CCH₃ | N | CH | CH | SCF₃ |
| CCH₃ | N | CH | CH | SOCH₃ |
| CCH₃ | N | CH | CH | SOCH₂CH₃ |
| CCH₃ | N | CH | CH | SOCF₃ |
| CCH₃ | N | CH | CH | SO₂CH₃ |
| CCH₃ | N | CH | CH | SO₂CH₂CH₃ |
| CCH₃ | N | CH | CH | SO₂CF₃ |
| CCH₃ | N | CH | CH | SO₂NH₂ |
| CCH₃ | N | CH | CH | NO₂ |
| CCH₃ | N | CH | CH | —CN |
| CH | N | CCH₃ | CH | F |
| CH | N | CCH₃ | CH | Cl |
| CH | N | CCH₃ | CH | Br |
| CH | N | CCH₃ | CH | I |
| CH | N | CCH₃ | CH | CH₃ |
| CH | N | CCH₃ | CH | CH₂CH₃ |
| CH | N | CCH₃ | CH | CF₃ |
| CH | N | CCH₃ | CH | CHF₂ |
| CH | N | CCH₃ | CH | CF₂CF₃ |
| CH | N | CCH₃ | CH | CF(CF₃)₂ |
| CH | N | CCH₃ | CH | OCH₃ |
| CH | N | CCH₃ | CH | OCH₂CH₃ |
| CH | N | CCH₃ | CH | OCF₃ |
| CH | N | CCH₃ | CH | OCHF₂ |
| CH | N | CCH₃ | CH | SCH₃ |
| CH | N | CCH₃ | CH | SCH₂CH₃ |
| CH | N | CCH₃ | CH | SCF₃ |
| CH | N | CCH₃ | CH | SOCH₃ |
| CH | N | CCH₃ | CH | SOCH₂CH₃ |
| CH | N | CCH₃ | CH | SOCF₃ |
| CH | N | CCH₃ | CH | SO₂CH₃ |
| CH | N | CCH₃ | CH | SO₂CH₂CH₃ |
| CH | N | CCH₃ | CH | SO₂CF₃ |
| CH | N | CCH₃ | CH | SO₂NH₂ |
| CH | N | CCH₃ | CH | NO₂ |
| CH | N | CCH₃ | CH | —CN |
| CH | N | CH | CCH₃ | F |
| CH | N | CH | CCH₃ | Cl |
| CH | N | CH | CCH₃ | Br |
| CH | N | CH | CCH₃ | I |
| CH | N | CH | CCH₃ | CH₃ |
| CH | N | CH | CCH₃ | CH₂CH₃ |
| CH | N | CH | CCH₃ | CF₃ |
| CH | N | CH | CCH₃ | CHF₂ |
| CH | N | CH | CCH₃ | CF₂CF₃ |
| CH | N | CH | CCH₃ | CF(CF₃)₂ |
| CH | N | CH | CCH₃ | OCH₃ |
| CH | N | CH | CCH₃ | OCH₂CH₃ |
| CH | N | CH | CCH₃ | OCF₃ |
| CH | N | CH | CCH₃ | OCHF₂ |
| CH | N | CH | CCH₃ | SCH₃ |
| CH | N | CH | CCH₃ | SCH₂CH₃ |
| CH | N | CH | CCH₃ | SCF₃ |
| CH | N | CH | CCH₃ | SOCH₃ |
| CH | N | CH | CCH₃ | SOCH₂CH₃ |
| CH | N | CH | CCH₃ | SOCF₃ |
| CH | N | CH | CCH₃ | SO₂CH₃ |
| CH | N | CH | CCH₃ | SO₂CH₂CH₃ |
| CH | N | CH | CCH₃ | SO₂CF₃ |
| CH | N | CH | CCH₃ | SO₂NH₂ |
| CH | N | CH | CCH₃ | NO₂ |
| CH | N | CH | CCH₃ | —CN |
| CCF₃ | N | CH | CH | F |
| CCF₃ | N | CH | CH | Cl |
| CCF₃ | N | CH | CH | Br |
| CCF₃ | N | CH | CH | I |
| CCF₃ | N | CH | CH | CH₃ |
| CCF₃ | N | CH | CH | CH₂CH₃ |
| CCF₃ | N | CH | CH | CF₃ |
| CCF₃ | N | CH | CH | CHF₂ |
| CCF₃ | N | CH | CH | CF₂CF₃ |

TABLE 1-continued

| $A_1$ | $A_2$ | $A_3$ | $A_4$ | X |
|---|---|---|---|---|
| $CCF_3$ | N | CH | CH | $CF(CF_3)_2$ |
| $CCF_3$ | N | CH | CH | $OCH_3$ |
| $CCF_3$ | N | CH | CH | $OCH_2CH_3$ |
| $CCF_3$ | N | CH | CH | $OCF_3$ |
| $CCF_3$ | N | CH | CH | $OCHF_2$ |
| $CCF_3$ | N | CH | CH | $SCH_3$ |
| $CCF_3$ | N | CH | CH | $SCH_2CH_3$ |
| $CCF_3$ | N | CH | CH | $SCF_3$ |
| $CCF_3$ | N | CH | CH | $SOCH_3$ |
| $CCF_3$ | N | CH | CH | $SOCH_2CH_3$ |
| $CCF_3$ | N | CH | CH | $SOCF_3$ |
| $CCF_3$ | N | CH | CH | $SO_2CH_3$ |
| $CCF_3$ | N | CH | CH | $SO_2CH_2CH_3$ |
| $CCF_3$ | N | CH | CH | $SO_2CF_3$ |
| $CCF_3$ | N | CH | CH | $SO_2NH_2$ |
| $CCF_3$ | N | CH | CH | $NO_2$ |
| $CCF_3$ | N | CH | CH | —CN |
| CH | N | $CCF_3$ | CH | F |
| CH | N | $CCF_3$ | CH | Cl |
| CH | N | $CCF_3$ | CH | Br |
| CH | N | $CCF_3$ | CH | I |
| CH | N | $CCF_3$ | CH | $CH_3$ |
| CH | N | $CCF_3$ | CH | $CH_2CH_3$ |
| CH | N | $CCF_3$ | CH | $CF_3$ |
| CH | N | $CCF_3$ | CH | $CHF_2$ |
| CH | N | $CCF_3$ | CH | $CF_2CF_3$ |
| CH | N | $CCF_3$ | CH | $CF(CF_3)_2$ |
| CH | N | $CCF_3$ | CH | $OCH_3$ |
| CH | N | $CCF_3$ | CH | $OCH_2CH_3$ |
| CH | N | $CCF_3$ | CH | $OCF_3$ |
| CH | N | $CCF_3$ | CH | $OCHF_2$ |
| CH | N | $CCF_3$ | CH | $SCH_3$ |
| CH | N | $CCF_3$ | CH | $SCH_2CH_3$ |
| CH | N | $CCF_3$ | CH | $SCF_3$ |
| CH | N | $CCF_3$ | CH | $SOCH_3$ |
| CH | N | $CCF_3$ | CH | $SOCH_2CH_3$ |
| CH | N | $CCF_3$ | CH | $SOCF_3$ |
| CH | N | $CCF_3$ | CH | $SO_2CH_3$ |
| CH | N | $CCF_3$ | CH | $SO_2CH_2CH_3$ |
| CH | N | $CCF_3$ | CH | $SO_2CF_3$ |
| CH | N | $CCF_3$ | CH | $SO_2NH_2$ |
| CH | N | $CCF_3$ | CH | $NO_2$ |
| CH | N | $CCF_3$ | CH | —CN |
| CH | N | CH | $CCF_3$ | F |
| CH | N | CH | $CCF_3$ | Cl |
| CH | N | CH | $CCF_3$ | Br |
| CH | N | CH | $CCF_3$ | I |
| CH | N | CH | $CCF_3$ | $CH_3$ |
| CH | N | CH | $CCF_3$ | $CH_2CH_3$ |
| CH | N | CH | $CCF_3$ | $CF_3$ |
| CH | N | CH | $CCF_3$ | $CHF_2$ |
| CH | N | CH | $CCF_3$ | $CF_2CF_3$ |
| CH | N | CH | $CCF_3$ | $CF(CF_3)_2$ |
| CH | N | CH | $CCF_3$ | $OCH_3$ |
| CH | N | CH | $CCF_3$ | $OCH_2CH_3$ |
| CH | N | CH | $CCF_3$ | $OCF_3$ |
| CH | N | CH | $CCF_3$ | $OCHF_2$ |
| CH | N | CH | $CCF_3$ | $SCH_3$ |
| CH | N | CH | $CCF_3$ | $SCH_2CH_3$ |
| CH | N | CH | $CCF_3$ | $SCF_3$ |
| CH | N | CH | $CCF_3$ | $SOCH_3$ |
| CH | N | CH | $CCF_3$ | $SOCH_2CH_3$ |
| CH | N | CH | $CCF_3$ | $SOCF_3$ |
| CH | N | CH | $CCF_3$ | $SO_2CH_3$ |
| CH | N | CH | $CCF_3$ | $SO_2CH_2CH_3$ |
| CH | N | CH | $CCF_3$ | $SO_2CF_3$ |
| CH | N | CH | $CCF_3$ | $SO_2NH_2$ |
| CH | N | CH | $CCF_3$ | $NO_2$ |
| CH | N | CH | $CCF_3$ | —CN |

The present disclosure also includes Tables 2 through 240 below. Each of Tables 2 through 240 lists multiple compounds that are within the scope of Formula (1), similar to Table 1. More specifically, each of Tables 2 through 240 lists the same combinations of $A_1$, $A_2$, $A_3$, $A_4$ and X as the combinations listed in Table 1, but the combination of $R_1$, $R_2$, $X_2$, $X_3$, $X_4$, $X_5$ and Y in each of Tables 2 through 240 differs from that in Table 1. Therefore, only the combinations of $R_1$, $R_2$, $X_2$, $X_3$, $X_4$, $X_5$ and Y in the respective Tables are indicated below, and the indication of the variations of the combination of $A_1$, $A_2$, $A_3$, $A_4$ and X in each Table is omitted since the variations are the same as those listed in Table 1.

In Table 1, the combination of $R_1$, $R_2$, $X_2$, $X_3$, $X_4$, $X_5$ and Y is such that "$R_1$ is $CH_3$, $R_2$ is $CF_3$, $X_2$ is F, $X_3$ is H, $X_4$ is F, $X_5$ is I, and Y is single bond". The combination of $R_1$, $R_2$, $X_2$, $X_3$, $X_4$, $X_5$ and Y in Table 2 is such that "$R_1$ is H, $R_2$ is $CF_3$, $X_2$ is F, $X_3$ is H, $X_4$ is F, $X_5$ is I, and Y is single bond", as indicated below. Thus, the first entry in Table 2 specifically discloses compound 2-fluoro-3-(4-fluorobenzamido)-N-(2-iodo-4-(perfluoropropan-2-yl)-6-(trifluoromethyl)phenyl)benzamide, which is a compound in which $A_1$ is CH, $A_2$ is CH, $A_3$ is CH, $A_4$ is CH, X is F, $R_1$ is H, $R_2$ is $CF_3$, $X_2$ is F, $X_3$ is H, $X_4$ is F, $X_5$ is I, and Y is single bond. Note that the first entry in Table 1 indicates "$A_1$ is CH, $A_2$ is CH, $A_3$ is CH, $A_4$ is CH, X is F". The compound specified in the second and subsequent entries in Table 2 can also be identified in the same manner, and the compounds listed in Tables 3 through 240 can also be identified in the same manner, taking into account the combination of $R_1$, $R_2$, $X_2$, $X_3$, $X_4$, $X_5$ and Y for each Table.

| Tables | Combination of $R_1$, $R_2$, $X_2$, $X_3$, $X_4$, $X_5$ and Y in Each Table |
|---|---|
| 2 | $R_1$ is H, $R_2$ is $CF_3$, $X_2$ is F, $X_3$ is H, $X_4$ is F, $X_5$ is I, and Y is single bond |
| 3 | $R_1$ is $CH_3$, $R_2$ is $CF_3$, $X_2$ is F, $X_3$ is H, $X_4$ is F, $X_5$ is Br and Y is single bond |
| 4 | $R_1$ is H, $R_2$ is $CF_3$, $X_2$ is F, $X_3$ is H, $X_4$ is F, $X_5$ is Br and Y is single bond |
| 5 | $R_1$ is $CH_3$, $R_2$ is $CF_3$, $X_2$ is F, $X_3$ is H, $X_4$ is F, $X_5$ is I and Y is O |
| 6 | $R_1$ is H, $R_2$ is $CF_3$, $X_2$ is F, $X_3$ is H, $X_4$ is F, $X_5$ is I and Y is O |
| 7 | $R_1$ is $CH_3$, $R_2$ is $CF_3$, $X_2$ is F, $X_3$ is H, $X_4$ is F, $X_5$ is Br and Y is O |
| 8 | $R_1$ is H, $R_2$ is $CF_3$, $X_2$ is F, $X_3$ is H, $X_4$ is F, $X_5$ is Br and Y is O |
| 9 | $R_1$ is $CH_3$, $R_2$ is $CF_3$, $X_2$ is F, $X_3$ is H, $X_4$ is F, $X_5$ is I and Y is S |
| 10 | $R_1$ is H, $R_2$ is $CF_3$, $X_2$ is F, $X_3$ is H, $X_4$ is F, $X_5$ is I and Y is S |
| 11 | $R_1$ is $CH_3$, $R_2$ is $CF_3$, $X_2$ is F, $X_3$ is H, $X_4$ is F, $X_5$ is Br and Y is S |
| 12 | $R_1$ is H, $R_2$ is $CF_3$, $X_2$ is F, $X_3$ is H, $X_4$ is F, $X_5$ is Br and Y is S |
| 13 | $R_1$ is $CH_3$, $R_2$ is $CF_3$, $X_2$ is F, $X_3$ is H, $X_4$ is F, $X_5$ is I and Y is SO |
| 14 | $R_1$ is H, $R_2$ is $CF_3$, $X_2$ is F, $X_3$ is H, $X_4$ is F, $X_5$ is I and Y is SO |
| 15 | $R_1$ is $CH_3$, $R_2$ is $CF_3$, $X_2$ is F, $X_3$ is H, $X_4$ is F, $X_5$ is Br and Y is SO |
| 16 | $R_1$ is H, $R_2$ is $CF_3$, $X_2$ is F, $X_3$ is H, $X_4$ is F, $X_5$ is Br and Y is SO |
| 17 | $R_1$ is $CH_3$, $R_2$ is $CF_3$, $X_2$ is F, $X_3$ is H, $X_4$ is F, $X_5$ is I and Y is $SO_2$ |
| 18 | $R_1$ is H, $R_2$ is $CF_3$, $X_2$ is F, $X_3$ is H, $X_4$ is F, $X_5$ is I and Y is $SO_2$ |
| 19 | $R_1$ is $CH_3$, $R_2$ is $CF_3$, $X_2$ is F, $X_3$ is H, $X_4$ is F, $X_5$ is Br and Y is $SO_2$ |
| 20 | $R_1$ is H, $R_2$ is $CF_3$, $X_2$ is F, $X_3$ is H, $X_4$ is F, $X_5$ is Br and Y is $SO_2$ |

-continued

| Tables | Combination of $R_1$, $R_2$, $X_2$, $X_3$, $X_4$, $X_5$ and Y in Each Table |
|---|---|
| 21 | $R_1$ is $CH_3$, $R_2$ is $CF_3$, $X_2$ is F, $X_3$ is H, $X_4$ is H, $X_5$ is I, and Y is single bond |
| 22 | $R_1$ is H, $R_2$ is $CF_3$, $X_2$ is F, $X_3$ is H, $X_4$ is H, $X_5$ is I, and Y is single bond |
| 23 | $R_1$ is $CH_3$, $R_2$ is $CF_3$, $X_2$ is F, $X_3$ is H, $X_4$ is H, $X_5$ is Br and Y is single bond |
| 24 | $R_1$ is H, $R_2$ is $CF_3$, $X_2$ is F, $X_3$ is H, $X_4$ is H, $X_5$ is Br and Y is single bond |
| 25 | $R_1$ is $CH_3$, $R_2$ is $CF_3$, $X_2$ is F, $X_3$ is H, $X_4$ is H, $X_5$ is I and Y is O |
| 26 | $R_1$ is H, $R_2$ is $CF_3$, $X_2$ is F, $X_3$ is H, $X_4$ is H $X_5$ is I and Y is O |
| 27 | $R_1$ is $CH_3$, $R_2$ is $CF_3$, $X_2$ is F, $X_3$ is H, $X_4$ is H, $X_5$ is Br and Y is O |
| 28 | $R_1$ is H, $R_2$ is $CF_3$, $X_2$ is F, $X_3$ is H, $X_4$ is H, $X_5$ is Br and Y is O |
| 29 | $R_1$ is $CH_3$, $R_2$ is $CF_3$, $X_2$ is F, $X_3$ is H, $X_4$ is H, $X_5$ is I and Y is S |
| 30 | $R_1$ is H, $R_2$ is $CF_3$, $X_2$ is F, $X_3$ is H, $X_4$ is H, $X_5$ is I and Y is S |
| 31 | $R_1$ is $CH_3$, $R_2$ is $CF_3$, $X_2$ is F, $X_3$ is H, $X_4$ is H, $X_5$ is Br and Y is S |
| 32 | $R_1$ is H, $R_2$ is $CF_3$, $X_2$ is F, $X_3$ is H, $X_4$ is H, $X_5$ is Br and Y is S |
| 33 | $R_1$ is $CH_3$, $R_2$ is $CF_3$, $X_2$ is F, $X_3$ is H, $X_4$ is H, $X_5$ is I and Y is SO |
| 34 | $R_1$ is H, $R_2$ is $CF_3$, $X_2$ is F, $X_3$ is H, $X_4$ is H, $X_5$ is I and Y is SO |
| 35 | $R_1$ is $CH_3$, $R_2$ is $CF_3$, $X_2$ is F, $X_3$ is H, $X_4$ is H, $X_5$ is Br and Y is SO |
| 36 | $R_1$ is H, $R_2$ is $CF_3$, $X_2$ is F, $X_3$ is H, $X_4$ is H, $X_5$ is Br and Y is SO |
| 37 | $R_1$ is $CH_3$, $R_2$ is $CF_3$, $X_2$ is F, $X_3$ is H, $X_4$ is H, $X_5$ is I and Y is $SO_2$ |
| 38 | $R_1$ is H, $R_2$ is $CF_3$, $X_2$ is F, $X_3$ is H, $X_4$ is H, $X_5$ is I and Y is $SO_2$ |
| 39 | $R_1$ is $CH_3$, $R_2$ is $CF_3$, $X_2$ is F, $X_3$ is H, $X_4$ is H, $X_5$ is Br and Y is $SO_2$ |
| 40 | $R_1$ is H, $R_2$ is $CF_3$, $X_2$ is F, $X_3$ is H, $X_4$ is H, $X_5$ is Br and Y is $SO_2$ |
| 41 | $R_1$ is $CH_3$, $R_2$ is $CF_2CF_3$, $X_2$ is F, $X_3$ is H, $X_4$ is F, $X_5$ is I, and Y is single bond |
| 42 | $R_1$ is H, $R_2$ is $CF_2CF_3$, $X_2$ is F, $X_3$ is H, $X_4$ is F, $X_5$ is I, and Y is single bond |
| 43 | $R_1$ is $CH_3$, $R_2$ is $CF_2CF_3$, $X_2$ is F, $X_3$ is H, $X_4$ is F, $X_5$ is Br and Y is single bond |
| 44 | $R_1$ is H, $R_2$ is $CF_2CF_3$, $X_2$ is F, $X_3$ is H, $X_4$ is F, $X_5$ is Br and Y is single bond |
| 45 | $R_1$ is $CH_3$, $R_2$ is $CF_2CF_3$, $X_2$ is F, $X_3$ is H, $X_4$ is F, $X_5$ is I and Y is O |
| 46 | $R_1$ is H, $R_2$ is $CF_2CF_3$, $X_2$ is F, $X_3$ is H, $X_4$ is F, $X_5$ is I and Y is O |
| 47 | $R_1$ is $CH_3$, $R_2$ is $CF_2CF_3$, $X_2$ is F, $X_3$ is H, $X_4$ is F, $X_5$ is Br and Y is O |
| 48 | $R_1$ is H, $R_2$ is $CF_2CF_3$, $X_2$ is F, $X_3$ is H, $X_4$ is F, $X_5$ is Br and Y is O |
| 49 | $R_1$ is $CH_3$, $R_2$ is $CF_2CF_3$, $X_2$ is F, $X_3$ is H, $X_4$ is F, $X_5$ is I and Y is S |
| 50 | $R_1$ is H, $R_2$ is $CF_2CF_3$, $X_2$ is F, $X_3$ is H, $X_4$ is F, $X_5$ is I and Y is S |
| 51 | R, is $CH_3$, $R_2$ is $CF_2CF_3$, $X_2$ is F, $X_3$ is H, $X_4$ is F, $X_5$ is Br and Y is S |
| 52 | $R_1$ is H, $R_2$ is $CF_2CF_3$, $X_2$ is F, $X_3$ is H, $X_4$. is F, $X_5$ is Br and Y is S |
| 53 | $R_1$ is $CH_3$, $R_2$ is $CF_2CF_3$, $X_2$ is F, $X_3$ is H, $X_4$ is F, $X_5$ is I and Y is SO |
| 54 | $R_1$ is H, $R_2$ is $CF_2CF_3$, $X_2$ is F, $X_3$ is H, $X_4$ is F, $X_5$ is I and Y is SO |
| 55 | $R_1$ is $CH_3$, $R_2$ is $CF_2CF_3$, $X_2$ is F, $X_3$ is H, $X_4$ is F, $X_5$ is Br and Y is SO |
| 56 | $R_1$ is H, $R_2$ is $CF_2CF_3$, $X_2$ is F, $X_3$ is H, $X_4$ is F, $X_5$ is Br and Y is SO |
| 57 | $R_1$ is $CH_3$, $R_2$ is $CF_2CF_3$, $X_2$ is F, $X_3$ is H, $X_4$ is F, $X_5$ is I and Y is $SO_2$ |
| 58 | $R_1$ is H, $R_2$ is $CF_2CF_3$, $X_2$ is F, $X_3$ is H, $X_4$ is F, $X_5$ is I and Y is $SO_2$ |
| 59 | $R_1$ is $CH_3$, $R_2$ is $CF_2CF_3$, $X_2$ is F, $X_3$ is H, $X_4$ is F, $X_5$ is Br and Y is $SO_2$ |
| 60 | $R_1$ is H, $R_2$ is $CF_2CF_3$, $X_2$ is F, $X_3$ is H, $X_4$ is F, $X_5$ is Br and Y is $SO_2$ |
| 61 | $R_1$ is $CH_3$, $R_2$ is $CF_2CF_3$, $X_2$ is F, $X_3$ is H, $X_4$ is H, $X_5$ is I, and Y is single bond |
| 62 | $R_1$ is H, $R_2$ is $CF_2CF_3$, $X_2$ is F, $X_3$ is H, $X_4$ is H, $X_5$ is I, and Y is single bond |
| 63 | $R_1$ is $CH_3$, $R_2$ is $CF_2CF_3$, $X_2$ is F, $X_3$ is H, $X_4$ is H, $X_5$ is Br and Y is single bond |
| 64 | $R_1$ is H, $R_2$ is $CF_2CF_3$, $X_2$ is F, $X_3$ is H, $X_4$ is H, $X_5$ is Br and Y is single bond |
| 65 | $R_1$ is $CH_3$, $R_2$ is $CF_2CF_3$, $X_2$ is F, $X_3$ is H, $X_4$ is H, $X_5$ is I and Y is O |
| 66 | $R_1$ is H, $R_2$ is $CF_2CF_3$, $X_2$ is F, $X_3$ is H, $X_4$ is H $X_5$ is I and Y is O |
| 67 | $R_1$ is $CH_3$, $R_2$ is $CF_2CF_3$, $X_2$ is F, $X_3$ is H, $X_4$ is H, $X_5$ is Br and Y is O |
| 68 | $R_1$ is H, $R_2$ is $CF_2CF_3$, $X_2$ is F, $X_3$ is H, $X_4$ is H, $X_5$ is Br and Y is O |
| 69 | $R_1$ is $CH_3$, $R_2$ is $CF_2CF_3$, $X_2$ is F, $X_3$ is H, $X_4$ is H, $X_5$ is I and Y is S |
| 70 | $R_1$ is H, $R_2$ is $CF_2CF_3$, $X_2$ is F, $X_3$ is H, $X_4$ is H, $X_5$ is I and Y is S |
| 71 | $R_1$ is $CH_3$, $R_2$ is $CF_2CF_3$, $X_2$ is F, $X_3$ is H, $X_4$ is H, $X_5$ is Br and Y is S |
| 72 | $R_1$ is H, $R_2$ is $CF_2CF_3$, $X_2$ is F, $X_3$ is H, $X_4$ is H, $X_5$ is Br and Y is S |
| 73 | $R_1$ is $CH_3$, $R_2$ is $CF_2CF_3$, $X_2$ is F, $X_3$ is H, $X_4$ is H, $X_5$ is I and Y is SO |
| 74 | $R_1$ is H, $R_2$ is $CF_2CF_3$, $X_2$ is F, $X_3$ is H, $X_4$ is H, $X_5$ is I and Y is SO |
| 75 | $R_1$ is $CH_3$, $R_2$ is $CF_2CF_3$, $X_2$ is F, $X_3$ is H, $X_4$ is H, $X_5$ is Br and Y is SO |
| 76 | $R_1$ is H, $R_2$ is $CF_2CF_3$, $X_2$ is F, $X_3$ is H, $X_4$ is H, $X_5$ is Br and Y is SO |
| 77 | $R_1$ is $CH_3$, $R_2$ is $CF_2CF_3$, $X_2$ is F, $X_3$ is H, $X_4$ is H, $X_5$ is I and Y is $SO_2$ |
| 78 | $R_1$ is H, $R_2$ is $CF_2CF_3$, $X_2$ is F, $X_3$ is H, $X_4$ is H, $X_5$ is I and Y is $SO_2$ |
| 79 | $R_1$ is $CH_3$, $R_2$ is $CF_2CF_3$, $X_2$ is F, $X_3$ is H, $X_4$ is H, $X_5$ is Br and Y is $SO_2$ |
| 80 | $R_1$ is H, $R_2$ is $CF_2CF_3$, $X_2$ is F, $X_3$ is H, $X_4$ is H, $X_5$ is Br and Y is $SO_2$ |
| 81 | $R_1$ is $CH_3$, $R_2$ is $CF_3$, $X_2$ is H, $X_3$ is F, $X_4$ is F, $X_5$ is I, and Y is single bond |
| 82 | $R_1$ is H, $R_2$ is $CF_3$, $X_2$ is H, $X_3$ is F, $X_4$ is F, $X_5$ is I, and Y is single bond |
| 83 | $R_1$ is $CH_3$, $R_2$ is $CF_3$, $X_2$ is H, $X_3$ is F, $X_4$ is F, $X_5$ is Br and Y is single bond |
| 84 | $R_1$ is H, $R_2$ is $CF_3$, $X_2$ is H, $X_3$ is F, $X_4$ is F, $X_5$ is Br and Y is single bond |
| 85 | $R_1$ is $CH_3$, $R_2$ is $CF_3$, $X_2$ is H, $X_3$ is F, $X_4$ is F, $X_5$ is I and Y is O |
| 86 | $R_1$ is H, $R_2$ is $CF_3$, $X_2$ is H, $X_3$ is F, $X_4$ is F, $X_5$ is I and Y is O |
| 87 | $R_1$ is $CH_3$, $R_2$ is $CF_3$, $X_2$ is H, $X_3$ is F, $X_4$ is F, $X_5$ is Br and Y is O |
| 88 | $R_1$ is H, $R_2$ is $CF_3$, $X_2$ is H, $X_3$ is F, $X_4$ is F, $X_5$ is Br and Y is O |
| 89 | $R_1$ is $CH_3$, $R_2$ is $CF_3$, $X_2$ is H, $X_3$ is F, $X_4$ is F, $X_5$ is I and Y is S |
| 90 | $R_1$ is H, $R_2$ is $CF_3$, $X_2$ is H, $X_3$ is F, $X_4$ is F, $X_5$ is I and Y is S |
| 91 | $R_1$ is $CH_3$, $R_2$ is $CF_3$, $X_2$ is H, $X_3$ is F, $X_4$ is F, $X_5$ is Br and Y is S |
| 92 | $R_1$ is H, $R_2$ is $CF_3$, $X_2$ is H, $X_3$ is F, $X_4$ is F, $X_5$ is Br and Y is S |
| 93 | $R_1$ is $CH_3$, $R_2$ is $CF_3$, $X_2$ is H, $X_3$ is F, $X_4$ is F, $X_5$ is I and Y is SO |
| 94 | $R_1$ is H, $R_2$ is $CF_3$, $X_2$ is H, $X_3$ is F, $X_4$ is F, $X_5$ is I and Y is SO |
| 95 | $R_1$ is $CH_3$, $R_2$ is $CF_3$, $X_2$ is H, $X_3$ is F, $X_4$ is F, $X_5$ is Br and Y is SO |
| 96 | $R_1$ is H, $R_2$ is $CF_3$, $X_2$ is H, $X_3$ is F, $X_4$ is F, $X_5$ is Br and Y is SO |
| 97 | $R_1$ is $CH_3$, $R_2$ is $CF_3$, $X_2$ is H, $X_3$ is F, $X_4$ is F, $X_5$ is I and Y is $SO_2$ |

-continued

| Tables | Combination of $R_1$, $R_2$, $X_2$, $X_3$, $X_4$, $X_5$ and Y in Each Table |
|---|---|
| 98 | $R_1$ is H, $R_2$ is $CF_3$, $X_2$ is H, $X_3$ is F, $X_4$ is F, $X_5$ is I and Y is $SO_2$ |
| 99 | $R_1$ is $CH_3$, $R_2$ is $CF_3$, $X_2$ is H, $X_3$ is F, $X_4$ is F, $X_5$ is Br and Y is $SO_2$ |
| 100 | $R_1$ is H, $R_2$ is $CF_3$, $X_2$ is H, $X_3$ is F, $X_4$ is F, $X_5$ is Br and Y is $SO_2$ |
| 101 | $R_1$ is $CH_3$, $R_2$ is $CF_3$, $X_2$ is H, $X_3$ is F, $X_4$ is H, $X_5$ is I, and Y is single bond |
| 102 | $R_1$ is H, $R_2$ is $CF_3$, $X_2$ is H, $X_3$ is F, $X_4$ is H, $X_5$ is I, and Y is single bond |
| 103 | $R_1$ is $CH_3$, $R_2$ is $CF_3$, $X_2$ is H, $X_3$ is F, $X_4$ is H, $X_5$ is Br and Y is single bond |
| 104 | $R_1$ is H, $R_2$ is $CF_3$, $X_2$ is H, $X_3$ is F, $X_4$ is H, $X_5$ is Br and Y is single bond |
| 105 | $R_1$ is $CH_3$, $R_2$ is $CF_3$, $X_2$ is H, $X_3$ is F, $X_4$ is H, $X_5$ is I and Y is O |
| 106 | $R_1$ is H, $R_2$ is $CF_3$, $X_2$ is H, $X_3$ is F, $X_4$ is H $X_5$ is I and Y is O |
| 107 | $R_1$ is $CH_3$, $R_2$ is $CF_3$ $X_2$ is H, $X_3$ is F, $X_4$ is H, $X_5$ is Br and Y is O |
| 108 | $R_1$ is H, $R_2$ is $CF_3$, $X_2$ is H, $X_3$ is F, $X_4$ is H, $X_5$ is Br and Y is O |
| 109 | $R_1$ is $CH_3$, $R_2$ is $CF_3$, $X_2$ is H, $X_3$ is F, $X_4$ is H, $X_5$ is I and Y is S |
| 110 | $R_1$ is H, $R_2$ is $CF_3$, $X_2$ is H, $X_3$ is F, $X_4$ is H, $X_5$ is I and Y is S |
| 111 | $R_1$ is $CH_3$, $R_2$ is $CF_3$, $X_2$ is H, $X_3$ is F, $X_4$ is H, $X_5$ is Br and Y is S |
| 112 | $R_1$ is H, $R_2$ is $CF_3$, $X_2$ is H, $X_3$ is F, $X_4$ is H, $X_5$ is Br and Y is S |
| 113 | $R_1$ is $CH_3$, $R_2$ is $CF_3$, $X_2$ is H, $X_3$ is F, $X_4$ is H, $X_5$ is I and Y is SO |
| 114 | $R_1$ is H, $R_2$ is $CF_3$, $X_2$ is H, $X_3$ is F, $X_4$ is H, $X_5$ is I and Y is SO |
| 115 | $R_1$ is $CH_3$, $R_2$ is $CF_3$, $X_2$ is H, $X_3$ is F, $X_4$ is H, $X_5$ is Br and Y is SO |
| 116 | $R_1$ is H, $R_2$ is $CF_3$, $X_2$ is H, $X_3$ is F, $X_4$ is H, $X_5$ is Br and Y is SO |
| 117 | $R_1$ is $CH_3$, $R_2$ is $CF_3$, $X_2$ is H, $X_3$ is F, $X_4$ is H, $X_5$ is I and Y is $SO_2$ |
| 118 | $R_1$ is H, $R_2$ is $CF_3$, $X_2$ is H, $X_3$ is F, $X_4$ is H, $X_5$ is I and Y is $SO_2$ |
| 119 | $R_1$ is $CH_3$, $R_2$ is $CF_3$, $X_2$ is H, $X_3$ is F, $X_4$ is H, $X_5$ is Br and Y is $SO_2$ |
| 120 | $R_1$ is H, $R_2$ is $CF_3$, $X_2$ is H, $X_3$ is F, $X_4$ is H, $X_5$ is Br and Y is $SO_2$ |
| 121 | $R_1$ is $CH_3$, $R_2$ is $CF_2CF_3$, $X_2$ is H, $X_3$ is F, $X_4$ is F, $X_5$ is I, and Y is single bond |
| 122 | $R_1$ is H, $R_2$ is $CF_2CF_3$, $X_2$ is H, $X_3$ is F, $X_4$ is F, $X_5$ is I, and Y is single bond |
| 123 | $R_1$ is $CH_3$, $R_2$ is $CF_2CF_3$, $X_2$ is H, $X_3$ is F, $X_4$ is F, $X_5$ is Br and Y is single bond |
| 124 | $R_1$ is H, $R_2$ is $CF_2CF_3$, $X_2$ is H, $X_3$ is F, $X_4$ is F, $X_5$ is Br and Y is single bond |
| 125 | $R_1$ is $CH_3$, $R_2$ is $CF_2CF_3$, $X_2$ is H, $X_3$ is F, $X_4$ is F, $X_5$ is I and Y is O |
| 126 | $R_1$ is H, $R_2$ is $CF_2CF_3$, $X_2$ is H, $X_3$ is F, $X_4$ is F, $X_5$ is I and Y is O |
| 127 | $R_1$ is $CH_3$, $R_2$ is $CF_2CF_3$, $X_2$ is H, $X_3$ is F, $X_4$ is F, $X_5$ is Br and Y is O |
| 128 | $R_1$ is H, $R_2$ is $CF_2CF_3$, $X_2$ is H, $X_3$ is F, $X_4$ is F, $X_5$ is Br and Y is O |
| 129 | $R_1$ is $CH_3$, $R_2$ is $CF_2CF_3$, $X_2$ is H, $X_3$ is F, $X_4$ is F, $X_5$ is I and Y is S |
| 130 | $R_1$ is H, $R_2$ is $CF_2CF_3$, $X_2$ is H, $X_3$ is F, $X_4$ is F, $X_5$ is I and Y is S |
| 131 | $R_1$ is $CH_3$, $R_2$ is $CF_2CF_3$, $X_2$ is H, $X_3$ is F, $X_4$ is F, $X_5$ is Br and Y is S |
| 132 | $R_1$ is H, $R_2$ is $CF_2CF_3$, $X_2$ is H, $X_3$ is F, $X_4$ is F, $X_5$ is Br and Y is S |
| 133 | $R_1$ is $CH_3$, $R_2$ is $CF_2CF_3$, $X_2$ is H, $X_3$ is F, $X_4$ is F, $X_5$ is I and Y is SO |
| 134 | $R_1$ is H, $R_2$ is $CF_2CF_3$, $X_2$ is H, $X_3$ is F, $X_4$ is F, $X_5$ is I and Y is SO |
| 135 | $R_1$ is $CH_3$, $R_2$ is $CF_2CF_3$, $X_2$ is H, $X_3$ is F, $X_4$ is F, $X_5$ is Br and Y is SO |
| 136 | $R_1$ is H, $R_2$ is $CF_2CF_3$, $X_2$ is H, $X_3$ is F, $X_4$ is F, $X_5$ is Br and Y is SO |
| 137 | $R_1$ is $CH_3$, $R_2$ is $CF_2CF_3$, $X_2$ is H, $X_3$ is F, $X_4$ is F, $X_5$ is I and Y is $SO_2$ |
| 138 | $R_1$ is H, $R_2$ is $CF_2CF_3$, $X_2$ is H, $X_3$ is F, $X_4$ is F, $X_5$ is I and Y is $SO_2$ |
| 139 | $R_1$ is $CH_3$, $R_2$ is $CF_2CF_3$, $X_2$ is H, $X_3$ is F, $X_4$ is F, $X_5$ is Br and Y is $SO_2$ |
| 140 | $R_1$ is H, $R_2$ is $CF_2CF_3$, $X_2$ is H, $X_3$ is F, $X_4$ is F, $X_5$ is Br and Y is $SO_2$ |
| 141 | $R_1$ is $CH_3$, $R_2$ is $CF_2CF_3$, $X_2$ is H, $X_3$ is F, $X_4$ is H, $X_5$ is I, and Y is single bond |
| 142 | $R_1$ is H, $R_2$ is $CF_2CF_3$, $X_2$ is H, $X_3$ is F, $X_4$ is H, $X_5$ is I, and Y is single bond |
| 143 | $R_1$ is $CH_3$, $R_2$ is $CF_2CF_3$, $X_2$ is H, $X_3$ is F, $X_4$ is H, $X_5$ is Br and Y is single bond |
| 144 | $R_1$ is H, $R_2$ is $CF_2CF_3$, $X_2$ is H, $X_3$ is F, $X_4$ is H, $X_5$ is Br and Y is single bond |
| 145 | $R_1$ is $CH_3$, $R_2$ is $CF_2CF_3$, $X_2$ is H, $X_3$ is F, $X_4$ is H, $X_5$ is I and Y is O |
| 146 | $R_1$ is H, $R_2$ is $CF_2CF_3$, $X_2$ is H, $X_3$ is F, $X_4$ is H $X_5$ is I and Y is O |
| 147 | $R_1$ is $CH_3$, $R_2$ is $CF_2CF_3$, $X_2$ is H, $X_3$ is F, $X_4$ is H, $X_5$ is Br and Y is O |
| 148 | $R_1$ is H, $R_2$ is $CF_2CF_3$, $X_2$ is H, $X_3$ is F, $X_4$ is H, $X_5$ is Br and Y is O |
| 149 | $R_1$ is $CH_3$, $R_2$ is $CF_2CF_3$, $X_2$ is H, $X_3$ is F, $X_4$ is H, $X_5$ is I and Y is S |
| 150 | $R_1$ is H, $R_2$ is $CF_2CF_3$, $X_2$ is H, $X_3$ is F, $X_4$ is H, $X_5$ is I and Y is S |
| 151 | $R_1$ is $CH_3$, $R_2$ is $CF_2CF_3$, $X_2$ is H, $X_3$ is F, $X_4$ is H, $X_5$ is Br and Y is S |
| 152 | $R_1$ is H, $R_2$ is $CF_2CF_3$, $X_2$ is H, $X_3$ is F, $X_4$ is H, $X_5$ is Br and Y is S |
| 153 | $R_1$ is $CH_3$, $R_2$ is $CF_2CF_3$, $X_2$ is H, $X_3$ is F, $X_4$ is H, $X_5$ is I and Y is SO |
| 154 | $R_1$ is H, $R_2$ is $CF_2CF_3$, $X_2$ is H, $X_3$ is F, $X_4$ is H, $X_5$ is I and Y is SO |
| 155 | $R_1$ is $CH_3$, $R_2$ is $CF_2CF_3$, $X_2$ is H, $X_3$ is F, $X_4$ is H, $X_5$ is Br and Y is SO |
| 156 | $R_1$ is H, $R_2$ is $CF_2CF_3$, $X_2$ is H, $X_3$ is F, $X_4$ is H, $X_5$ is Br and Y is SO |
| 157 | $R_1$ is $CH_3$, $R_2$ is $CF_2CF_3$, $X_2$ is H, $X_3$ is F, $X_4$ is H, $X_5$ is I and Y is $SO_2$ |
| 158 | $R_1$ is H, $R_2$ is $CF_2CF_3$, $X_2$ is H, $X_3$ is F, $X_4$ is H, $X_5$ is I and Y is $SO_2$ |
| 159 | $R_1$ is $CH_3$, $R_2$ is $CF_2CF_3$, $X_2$ is H, $X_3$ is F, $X_4$ is H, $X_5$ is Br and Y is $SO_2$ |
| 160 | $R_1$ is H, $R_2$ is $CF_2CF_3$, $X_2$ is H, $X_3$ is F, $X_4$ is H, $X_5$ is Br and Y is $SO_2$ |
| 161 | $R_1$ is $CH_3$, $R_2$ is $CF_3$, $X_2$ is H, $X_3$ is H, $X_4$ is F, $X_5$ is I, and Y is single bond |
| 162 | $R_1$ is H, $R_2$ is $CF_3$, $X_2$ is H, $X_3$ is H, $X_4$ is F, $X_5$ is I, and Y is single bond |
| 163 | $R_1$ is $CH_3$, $R_2$ is $CF_3$, $X_2$ is H, $X_3$ is H, $X_4$ is F, $X_5$ is Br and Y is single bond |
| 164 | $R_1$ is H, $R_2$ is $CF_3$, $X_2$ is H, $X_3$ is H, $X_4$ is F, $X_5$ is Br and Y is single bond |
| 165 | $R_1$ is $CH_3$, $R_2$ is $CF_3$, $X_2$ is H, $X_3$ is H, $X_4$ is F, $X_5$ is I and Y is O |
| 166 | $R_1$ is H, $R_2$ is $CF_3$, $X_2$ is H, $X_3$ is H, $X_4$ is F, $X_5$ is I and Y is O |
| 167 | $R_1$ is $CH_3$, $R_2$ is $CF_3$, $X_2$ is H, $X_3$ is H, $X_4$ is F, $X_5$ is Br and Y is O |
| 168 | $R_1$ is H, $R_2$ is $CF_3$, $X_2$ is H, $X_3$ is H, $X_4$ is F, $X_5$ is Br and Y is O |
| 169 | $R_1$ is $CH_3$, $R_2$ is $CF_3$, $X_2$ is H, $X_3$ is H, $X_4$ is F, $X_5$ is I and Y is S |
| 170 | $R_1$ is H, $R_2$ is $CF_3$, $X_2$ is H, $X_3$ is H, $X_4$ is F, $X_5$ is I and Y is S |
| 171 | $R_1$ is $CH_3$, $R_2$ is $CF_3$, $X_2$ is H, $X_3$ is H, $X_4$ is F, $X_5$ is Br and Y is S |
| 172 | $R_1$ is H, $R_2$ is $CF_3$, $X_2$ is H, $X_3$ is H, $X_4$ is F, $X_5$ is Br and Y is S |
| 173 | $R_1$ is $CH_3$, $R_2$ is $CF_3$, $X_2$ is H, $X_3$ is H, $X_4$ is F, $X_5$ is I and Y is SO |
| 174 | $R_1$ is H, $R_2$ is $CF_3$, $X_2$ is H, $X_3$ is H, $X_4$ is F, $X_5$ is I and Y is SO |

-continued

| Tables | Combination of $R_1$, $R_2$, $X_2$, $X_3$, $X_4$, $X_5$ and Y in Each Table |
|---|---|
| 175 | $R_1$ is $CH_3$, $R_2$ is $CF_3$, $X_2$ is H, $X_3$ is H, $X_4$ is F, $X_5$ is Br and Y is SO |
| 176 | $R_1$ is H, $R_2$ is $CF_3$, $X_2$ is H, $X_3$ is H, $X_4$ is F, $X_5$ is Br and Y is SO |
| 177 | $R_1$ is $CH_3$, $R_2$ is $CF_3$, $X_2$ is H, $X_3$ is H, $X_4$ is F, $X_5$ is I and Y is $SO_2$ |
| 178 | $R_1$ is H, $R_2$ is $CF_3$, $X_2$ is H, $X_3$ is H, $X_4$ is F, $X_5$ is I and Y is $SO_2$ |
| 179 | $R_1$ is $CH_3$, $R_2$ is $CF_3$, $X_2$ is H, $X_3$ is H, $X_4$ is F, $X_5$ is Br and Y is $SO_2$ |
| 180 | $R_1$ is H, $R_2$ is $CF_3$, $X_2$ is H, $X_3$ is H, $X_4$ is F, $X_5$ is Br and Y is $SO_2$ |
| 181 | $R_1$ is $CH_3$, $R_2$ is $CF_3$, $X_2$ is H, $X_3$ is H, $X_4$ is H, $X_5$ is I, and Y is single bond |
| 182 | $R_1$ is H, $R_2$ is $CF_3$, $X_2$ is H, $X_3$ is H, $X_4$ is H, $X_5$ is I, and Y is single bond |
| 183 | $R_1$ is $CH_3$, $R_2$ is $CF_3$, $X_2$ is H, $X_3$ is H, $X_4$ is H, $X_5$ is Br and Y is single bond |
| 184 | $R_1$ is H, $R_2$ is $CF_3$, $X_2$ is H, $X_3$ is H, $X_4$ is H, $X_5$ is Br and Y is single bond |
| 185 | $R_1$ is $CH_3$, $R_2$ is $CF_3$, $X_2$ is H, $X_3$ is H, $X_4$ is H, $X_5$ is I and Y is O |
| 186 | $R_1$ is H, $R_2$ is $CF_3$, $X_2$ is H, $X_3$ is H, $X_4$ is H $X_5$ is I and Y is O |
| 187 | $R_1$ is $CH_3$, $R_2$ is $CF_3$ $X_2$ is H, $X_3$ is H, $X_4$ is H, $X_5$ is Br and Y is O |
| 188 | $R_1$ is H, $R_2$ is $CF_3$, $X_2$ is H, $X_3$ is H, $X_4$ is H, $X_5$ is Br and Y is O |
| 189 | $R_1$ is $CH_3$, $R_2$ is $CF_3$, $X_2$ is H, $X_3$ is H, $X_4$ is H, $X_5$ is I and Y is S |
| 190 | $R_1$ is H, $R_2$ is $CF_3$, $X_2$ is H, $X_3$ is H, $X_4$ is H, $X_5$ is I and Y is S |
| 191 | $R_1$ is $CH_3$, $R_2$ is $CF_3$, $X_2$ is H, $X_3$ is H, $X_4$ is H, $X_5$ is Br and Y is S |
| 192 | $R_1$ is H, $R_2$ is $CF_3$, $X_2$ is H, $X_3$ is H, $X_4$ is H, $X_5$ is Br and Y is S |
| 193 | $R_1$ is $CH_3$, $R_2$ is $CF_3$, $X_2$ is H, $X_3$ is H, $X_4$ is H, $X_5$ is I and Y is SO |
| 194 | $R_1$ is H, $R_2$ is $CF_3$, $X_2$ is H, $X_3$ is H, $X_4$ is H, $X_5$ is I and Y is SO |
| 195 | $R_1$ is $CH_3$, $R_2$ is $CF_3$, $X_2$ is H, $X_3$ is H, $X_4$ is H, $X_5$ is Br and Y is SO |
| 196 | $R_1$ is H, $R_2$ is $CF_3$, $X_2$ is H, $X_3$ is H, $X_4$ is H, $X_5$ is Br and Y is SO |
| 197 | $R_1$ is $CH_3$, $R_2$ is $CF_3$, $X_2$ is H, $X_3$ is H, $X_4$ is H, $X_5$ is I and Y is $SO_2$ |
| 198 | $R_1$ is H, $R_2$ is $CF_3$, $X_2$ is H, $X_3$ is H, $X_4$ is H, $X_5$ is I and Y is $SO_2$ |
| 199 | $R_1$ is $CH_3$, $R_2$ is $CF_3$, $X_2$ is H, $X_3$ is H, $X_4$ is H, $X_5$ is Br and Y is $SO_2$ |
| 200 | $R_1$ is H, $R_2$ is $CF_3$, $X_2$ is H, $X_3$ is H, $X_4$ is H, $X_5$ is Br and Y is $SO_2$ |
| 201 | $R_1$ is $CH_3$, $R_2$ is $CF_2CF_3$, $X_2$ is H, $X_3$ is H, $X_4$ is F, $X_5$ is I, and Y is single bond |
| 202 | $R_1$ is H, $R_2$ is $CF_2CF_3$, $X_2$ is H, $X_3$ is H, $X_4$ is F, $X_5$ is I, and Y is single bond |
| 203 | $R_1$ is $CH_3$, $R_2$ is $CF_2CF_3$, $X_2$ is H, $X_3$ is H, $X_4$ is F, $X_5$ is Br and Y is single bond |
| 204 | $R_1$ is H, $R_2$ is $CF_2CF_3$, $X_2$ is H, $X_3$ is H, $X_4$ is F, $X_5$ is Br and Y is single bond |
| 205 | $R_1$ is $CH_3$, $R_2$ is $CF_2CF_3$, $X_2$ is H, $X_3$ is H, $X_4$ is F, $X_5$ is I and Y is O |
| 206 | $R_1$ is H, $R_2$ is $CF_2CF_3$, $X_2$ is H, $X_3$ is H, $X_4$ is F, $X_5$ is I and Y is O |
| 207 | $R_1$ is $CH_3$, $R_2$ is $CF_2CF_3$, $X_2$ is H, $X_3$ is H, $X_4$ is F, $X_5$ is Br and Y is O |
| 208 | $R_1$ is H, $R_2$ is $CF_2CF_3$, $X_2$ is H, $X_3$ is H, $X_4$ is F, $X_5$ is Br and Y is O |
| 209 | $R_1$ is $CH_3$, $R_2$ is $CF_2CF_3$, $X_2$ is H, $X_3$ is H, $X_4$ is F, $X_5$ is I and Y is S |
| 210 | $R_1$ is H, $R_2$ is $CF_2CF_3$, $X_2$ is H, $X_3$ is H, $X_4$ is F, $X_5$ is I and Y is S |
| 211 | $R_1$ is $CH_3$, $R_2$ is $CF_2CF_3$, $X_2$ is H, $X_3$ is H, $X_4$ is F, $X_5$ is Br and Y is S |
| 212 | $R_1$ is H, $R_2$ is $CF_2CF_3$, $X_2$ is H, $X_3$ is H, $X_4$ is F, $X_5$ is Br and Y is S |
| 213 | $R_1$ is $CH_3$, $R_2$ is $CF_2CF_3$, $X_2$ is H, $X_3$ is H, $X_4$ is F, $X_5$ is I and Y is SO |
| 214 | $R_1$ is H, $R_2$ is $CF_2CF_3$, $X_2$ is H, $X_3$ is F, $X_4$ is F, $X_5$ is I and Y is SO |
| 215 | $R_1$ is $CH_3$, $R_2$ is $CF_2CF_3$, $X_2$ is H, $X_3$ is H, $X_4$ is F, $X_5$ is Br and Y is SO |
| 216 | $R_1$ is H, $R_2$ is $CF_2CF_3$, $X_2$ is H, $X_3$ is H, $X_4$ is F, $X_5$ is Br and Y is SO |
| 217 | $R_1$ is $CH_3$, $R_2$ is $CF_2CF_3$, $X_2$ is H, $X_3$ is H, $X_4$ is F, $X_5$ is I and Y is $SO_2$ |
| 218 | $R_1$ is H, $R_2$ is $CF_2CF_3$, $X_2$ is H, $X_3$ is H, $X_4$ is F, $X_5$ is I and Y is $SO_2$ |
| 219 | $R_1$ is $CH_3$, $R_2$ is $CF_2CF_3$, $X_2$ is H, $X_3$ is H, $X_4$ is F, $X_5$ is Br and Y is $SO_2$ |
| 220 | $R_1$ is H, $R_2$ is $CF_2CF_3$, $X_2$ is H, $X_3$ is H, $X_4$ is F, $X_5$ is Br and Y is $SO_2$ |
| 221 | $R_1$ is $CH_3$, $R_2$ is $CF_2CF_3$, $X_2$ is H, $X_3$ is H, $X_4$ is H, $X_5$ is I, and Y is single bond |
| 222 | R1 is H, $R_2$ is $CF_2CF_3$, $X_2$ is H, $X_3$ is H, $X_4$ is H, $X_5$ is I, and Y is single bond |
| 223 | $R_1$ is $CH_3$, $R_2$ is $CF_2CF_3$, $X_2$ is H, $X_3$ is H, $X_4$ is H, $X_5$ is Br and Y is single bond |
| 224 | $R_1$ is H, $R_2$ is $CF_2CF_3$, $X_2$ is H, $X_3$ is H, $X_4$ is H, $X_5$ is Br and Y is single bond |
| 225 | $R_1$ is $CH_3$, $R_2$ is $CF_2CF_3$, $X_2$ is H, $X_3$ is H, $X_4$ is H, $X_5$ is I and Y is O |
| 226 | $R_1$ is H, $R_2$ is $CF_2CF_3$, $X_2$ is H, $X_3$ is H, $X_4$ is H $X_5$ is I and Y is O |
| 227 | $R_1$ is $CH_3$, $R_2$ is $CF_2CF_3$, $X_2$ is H, $X_3$ is H, $X_4$ is H, $X_5$ is Br and Y is O |
| 228 | $R_1$ is H, $R_2$ is $CF_2CF_3$, $X_2$ is H, $X_3$ is H, $X_4$ is H, $X_5$ is Br and Y is O |
| 229 | $R_1$ is $CH_3$, $R_2$ is $CF_2CF_3$, $X_2$ is H, $X_3$ is H, $X_4$ is H, $X_5$ is I and Y is S |
| 230 | $R_1$ is H, $R_2$ is $CF_2CF_3$, $X_2$ is H, $X_3$ is H, $X_4$ is H, $X_5$ is I and Y is S |
| 231 | $R_1$ is $CH_3$, $R_2$ is $CF_2CF_3$, $X_2$ is H, $X_3$ is H, $X_4$ is H, $X_5$ is Br and Y is S |
| 232 | $R_1$ is H, $R_2$ is $CF_2CF_3$, $X_2$ is H, $X_3$ is H, $X_4$ is H, $X_5$ is Br and Y is S |
| 233 | $R_1$ is $CH_3$, $R_2$ is $CF_2CF_3$, $X_2$ is H, $X_3$ is H, $X_4$ is H, $X_5$ is I and Y is SO |
| 234 | $R_1$ is H, $R_2$ is $CF_2CF_3$, $X_2$ is H, $X_3$ is H, $X_4$ is H, $X_5$ is I and Y is SO |
| 235 | $R_1$ is $CH_3$, $R_2$ is $CF_2CF_3$, $X_2$ is H, $X_3$ is H, $X_4$ is H, $X_5$ is Br and Y is SO |
| 236 | $R_1$ is H, $R_2$ is $CF_2CF_3$, $X_2$ is H, $X_3$ is H, $X_4$ is H, $X_5$ is Br and Y is SO |
| 237 | $R_1$ is $CH_3$, $R_2$ is $CF_2CF_3$, $X_2$ is H, $X_3$ is H, $X_4$ is H, $X_5$ is I and Y is $SO_2$ |
| 238 | $R_1$ is H, $R_2$ is $CF_2CF_3$, $X_2$ is H, $X_3$ is H, $X_4$ is H, $X_5$ is I and Y is $SO_2$ |
| 239 | $R_1$ is $CH_3$, $R_2$ is $CF_2CF_3$, $X_2$ is H, $X_3$ is H, $X_4$ is H, $X_5$ is Br and Y is $SO_2$ |
| 240 | $R_1$ is H, $R_2$ is $CF_2CF_3$, $X_2$ is H, $X_3$ is H, $X_4$ is H, $X_5$ is Br and Y is $SO_2$ |

Preferred examples of compounds represented by Formula (1) that can be used in the present invention includes the compounds shown in the following Table 241.

TABLE 241

| Compound | Structure |
| --- | --- |
| 1 | 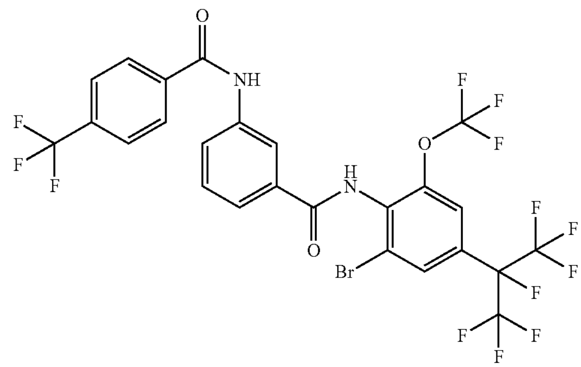 [SMILES: O=C(Nc1cccc(C(=O)Nc2c(Br)cc(C(F)(C(F)(F)F)C(F)(F)F)cc2OC(F)(F)F)c1)c1ccc(C(F)(F)F)cc1] |
| 2 | 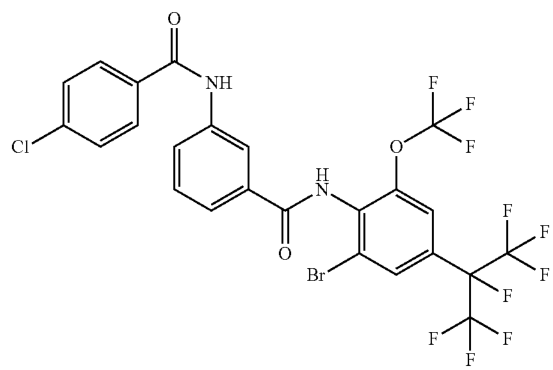 [SMILES: O=C(Nc1cccc(C(=O)Nc2c(Br)cc(C(F)(C(F)(F)F)C(F)(F)F)cc2OC(F)(F)F)c1)c1ccc(Cl)cc1] |
| 3 | 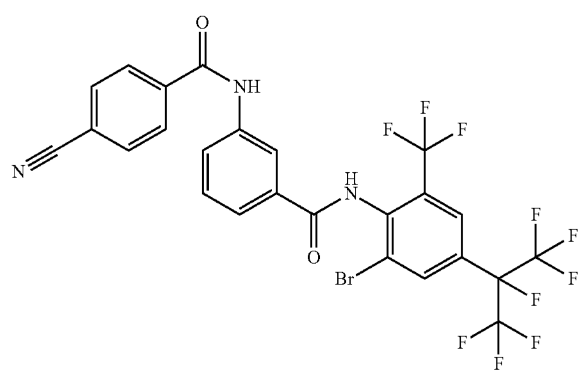 [SMILES: N#Cc1ccc(C(=O)Nc2cccc(C(=O)Nc3c(Br)cc(C(F)(C(F)(F)F)C(F)(F)F)cc3C(F)(F)F)c2)cc1] |
| 4 | 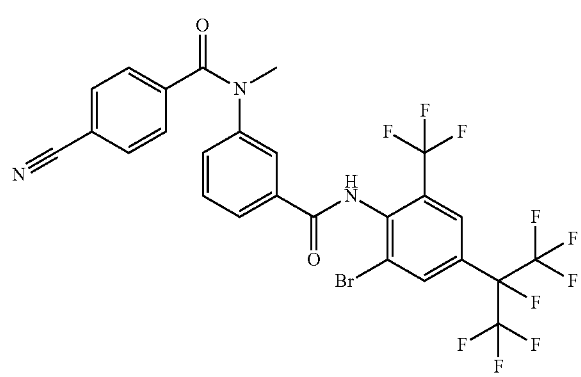 [SMILES: CN(C(=O)c1ccc(C#N)cc1)c1cccc(C(=O)Nc2c(Br)cc(C(F)(C(F)(F)F)C(F)(F)F)cc2C(F)(F)F)c1] |

TABLE 241-continued
| Compound | Structure |
|---|---|
| 5 | 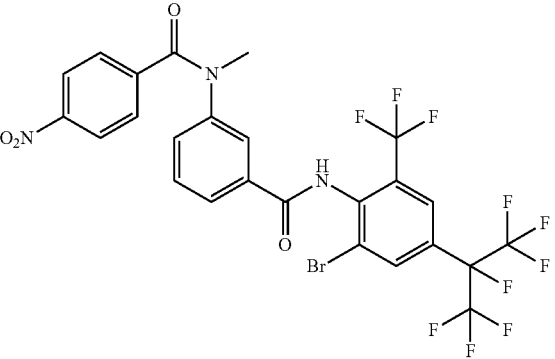 [SMILES: CN(C(=O)c1ccc([N+](=O)[O-])cc1)c1cccc(C(=O)Nc2c(Br)cc(C(F)(C(F)(F)F)C(F)(F)F)cc2C(F)(F)F)c1] |
| 6 | 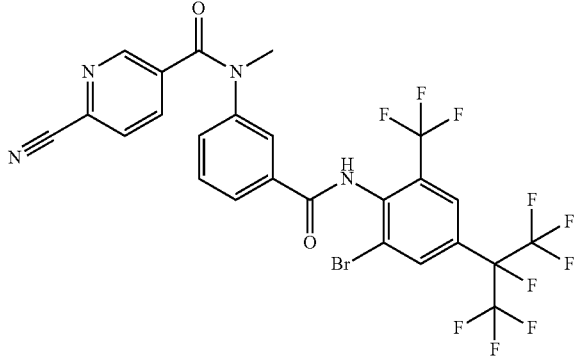 |
| 7 | 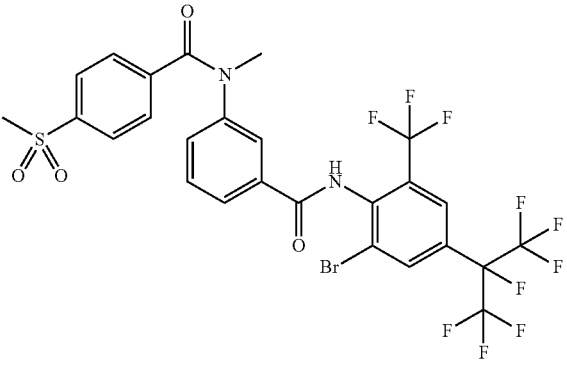 [SMILES: CN(C(=O)c1ccc(S(C)(=O)=O)cc1)c1cccc(C(=O)Nc2c(Br)cc(C(F)(C(F)(F)F)C(F)(F)F)cc2C(F)(F)F)c1] |
| 8 | 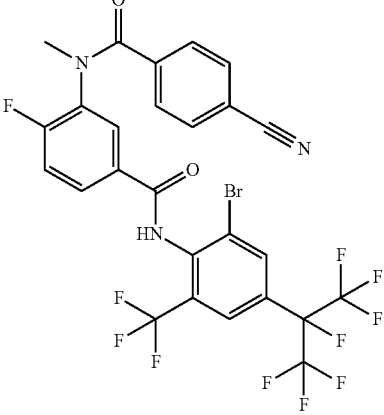 |

TABLE 241-continued

| Compound | Structure |
|---|---|
| 9 | 4-cyano-benzamide linked via NH to a pyridine-carboxamide, N-H to 2-bromo-6-(trifluoromethoxy)-4-(perfluoroethyl... |

| Compound | Structure |
|---|---|
| 9 | *(structure image)* |
| 19 | *(structure image)* |
| 20 | *(structure image)* |
| 21 | *(structure image)* |

TABLE 241-continued

| Compound | Structure |
|---|---|
| 22 | 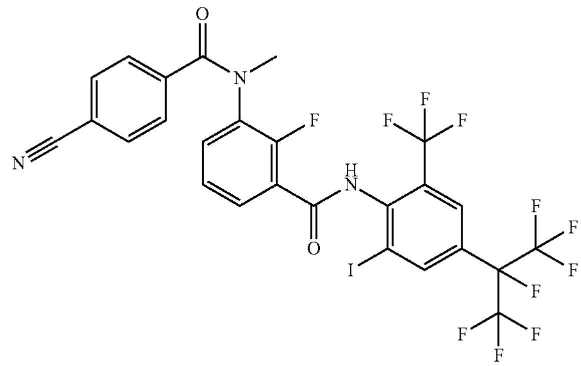 [SMILES: CN(C(=O)c1ccc(C#N)cc1)c1cccc(C(=O)Nc2c(I)cc(C(F)(C(F)(F)F)C(F)(F)F)cc2C(F)(F)F)c1F] |
| 23 | 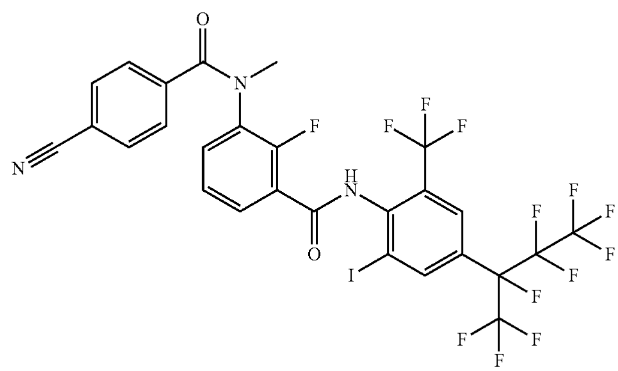 [SMILES: CN(C(=O)c1ccc(C#N)cc1)c1cccc(C(=O)Nc2c(I)cc(C(F)(C(F)(F)F)C(F)(F)C(F)(F)F)cc2C(F)(F)F)c1F] |
| 24 | 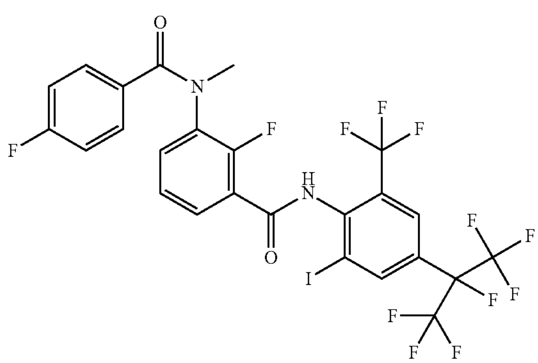 [SMILES: CN(C(=O)c1ccc(F)cc1)c1cccc(C(=O)Nc2c(I)cc(C(F)(C(F)(F)F)C(F)(F)F)cc2C(F)(F)F)c1F] |
| 25 | 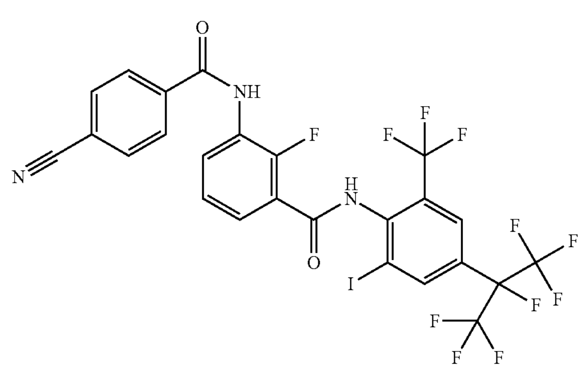 [SMILES: N#Cc1ccc(C(=O)Nc2cccc(C(=O)Nc3c(I)cc(C(F)(C(F)(F)F)C(F)(F)F)cc3C(F)(F)F)c2F)cc1] |

TABLE 241-continued

| Compound | Structure |
| --- | --- |
| 26 | *(structure)* |
| 27 | *(structure)* |
| 37 | *(structure)* |
| 38 | *(structure)* |

TABLE 241-continued

| Compound | Structure |
| --- | --- |
| 39 | 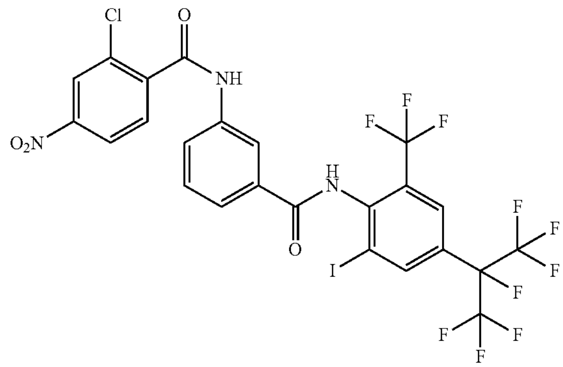 [SMILES: O=C(Nc1c(I)cc(C(F)(C(F)(F)F)C(F)(F)F)cc1C(F)(F)F)c1cccc(NC(=O)c2ccc([N+](=O)[O-])cc2Cl)c1] |
| 40 | 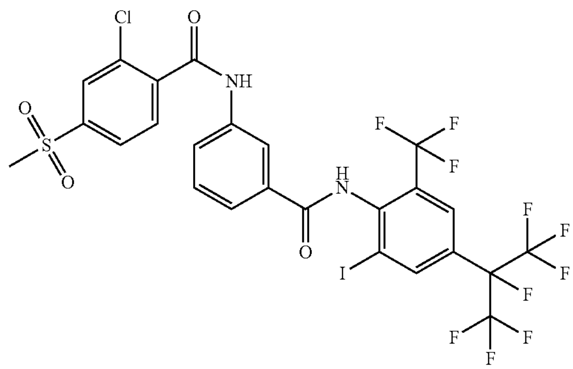 [SMILES: CS(=O)(=O)c1ccc(C(=O)Nc2cccc(C(=O)Nc3c(I)cc(C(F)(C(F)(F)F)C(F)(F)F)cc3C(F)(F)F)c2)c(Cl)c1] |
| 41 | 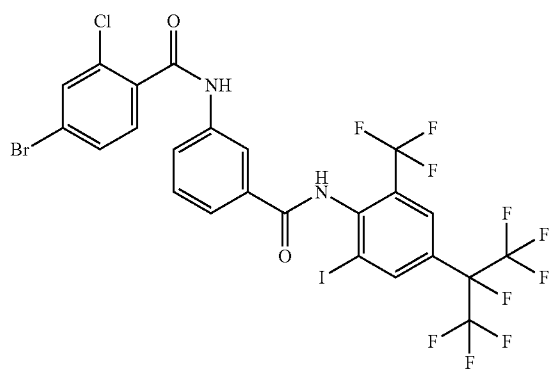 [SMILES: O=C(Nc1c(I)cc(C(F)(C(F)(F)F)C(F)(F)F)cc1C(F)(F)F)c1cccc(NC(=O)c2ccc(Br)cc2Cl)c1] |
| 42 | 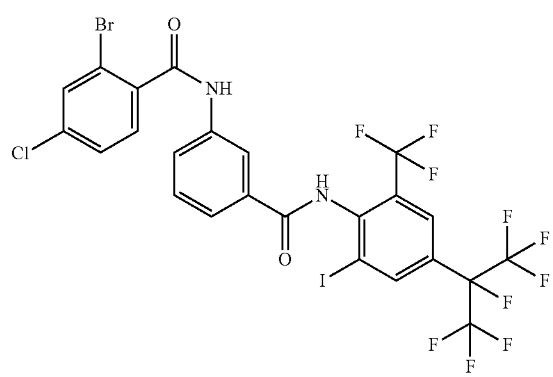 [SMILES: O=C(Nc1c(I)cc(C(F)(C(F)(F)F)C(F)(F)F)cc1C(F)(F)F)c1cccc(NC(=O)c2ccc(Cl)cc2Br)c1] |

TABLE 241-continued
| Compound | Structure |
|---|---|
| 43 | 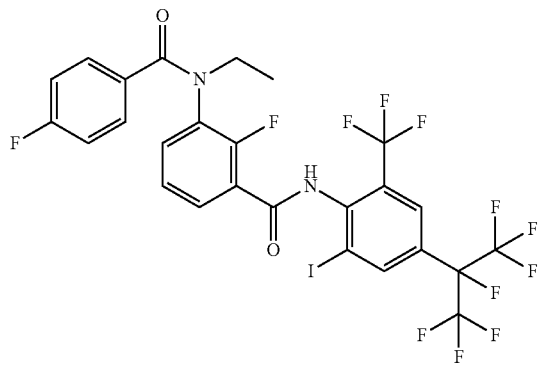 [SMILES: CCN(C(=O)c1ccc(F)cc1)c1cccc(C(=O)Nc2c(I)cc(C(F)(C(F)(F)F)C(F)(F)F)cc2C(F)(F)F)c1F] |
| 44 | 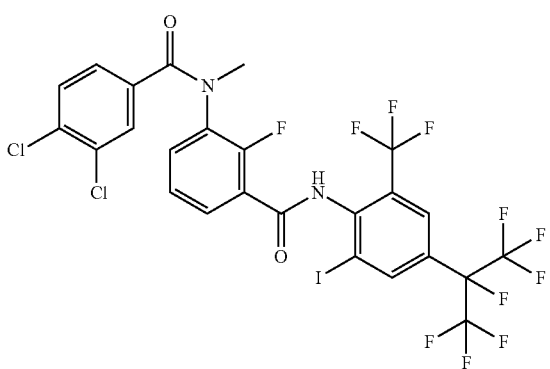 [SMILES: CN(C(=O)c1ccc(Cl)c(Cl)c1)c1cccc(C(=O)Nc2c(I)cc(C(F)(C(F)(F)F)C(F)(F)F)cc2C(F)(F)F)c1F] |
| 45 | 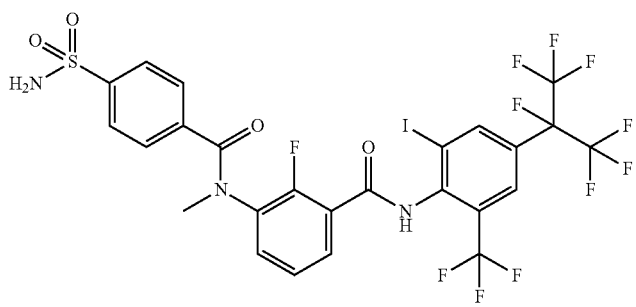 [SMILES: CN(C(=O)c1ccc(S(N)(=O)=O)cc1)c1cccc(C(=O)Nc2c(I)cc(C(F)(C(F)(F)F)C(F)(F)F)cc2C(F)(F)F)c1F] |
| 55 | 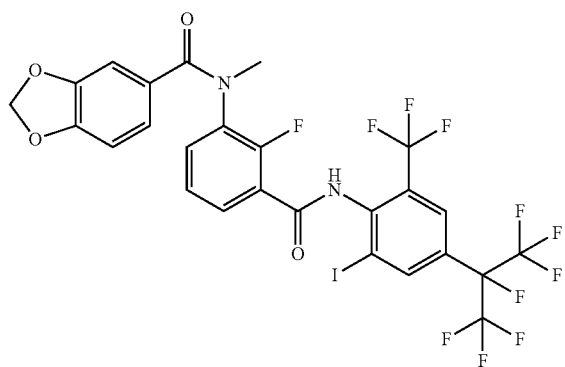 [SMILES: CN(C(=O)c1ccc2c(c1)OCO2)c1cccc(C(=O)Nc2c(I)cc(C(F)(C(F)(F)F)C(F)(F)F)cc2C(F)(F)F)c1F] |

TABLE 241-continued
| Compound | Structure |
|---|---|
| 56 | 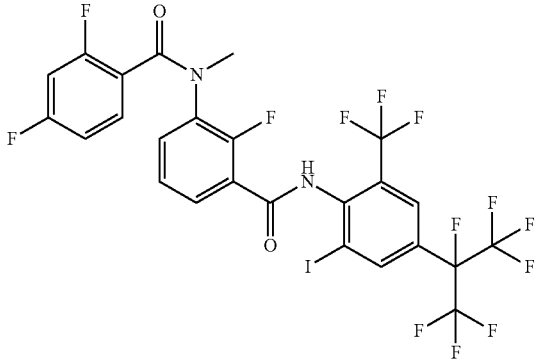 [SMILES: CN(C(=O)c1ccc(F)cc1F)c1cccc(C(=O)Nc2c(I)cc(C(F)(C(F)(F)F)C(F)(F)F)cc2C(F)(F)F)c1F] |
| 57 | 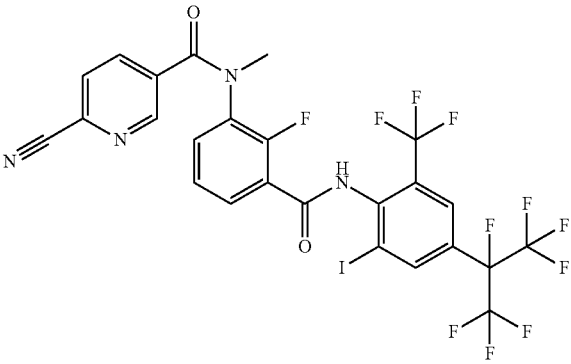 [SMILES: CN(C(=O)c1ccc(C#N)nc1)c1cccc(C(=O)Nc2c(I)cc(C(F)(C(F)(F)F)C(F)(F)F)cc2C(F)(F)F)c1F] |
| 58 | 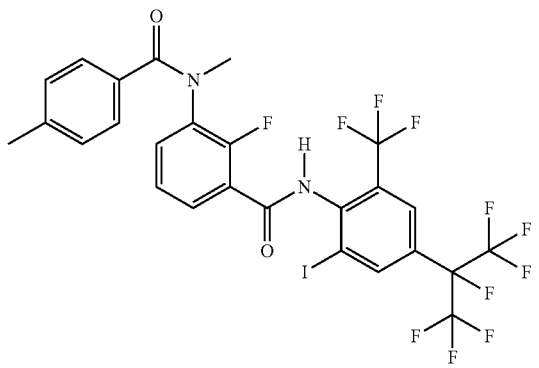 [SMILES: Cc1ccc(C(=O)N(C)c2cccc(C(=O)Nc3c(I)cc(C(F)(C(F)(F)F)C(F)(F)F)cc3C(F)(F)F)c2F)cc1] |
| 59 | 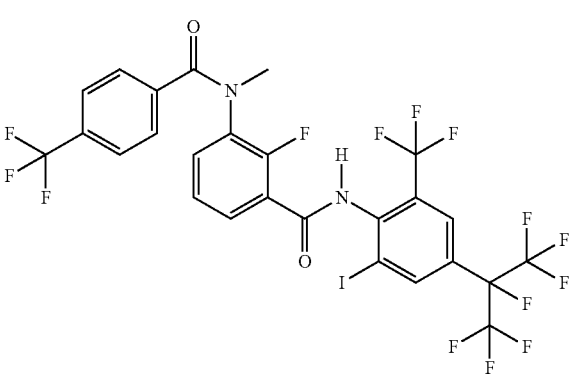 [SMILES: CN(C(=O)c1ccc(C(F)(F)F)cc1)c1cccc(C(=O)Nc2c(I)cc(C(F)(C(F)(F)F)C(F)(F)F)cc2C(F)(F)F)c1F] |

TABLE 241-continued
| Compound | Structure |
|---|---|
| 60 | 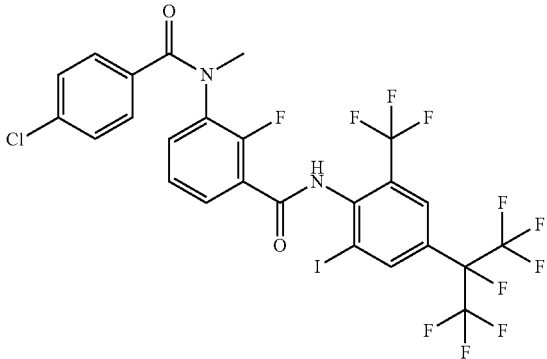 [SMILES: CN(C(=O)c1ccc(Cl)cc1)c1cccc(C(=O)Nc2c(I)cc(C(F)(C(F)(F)F)C(F)(F)F)cc2C(F)(F)F)c1F] |
| 61 | 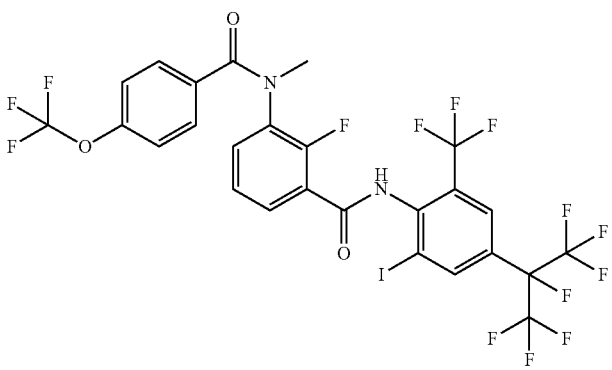 [SMILES: CN(C(=O)c1ccc(OC(F)(F)F)cc1)c1cccc(C(=O)Nc2c(I)cc(C(F)(C(F)(F)F)C(F)(F)F)cc2C(F)(F)F)c1F] |
| 62 | 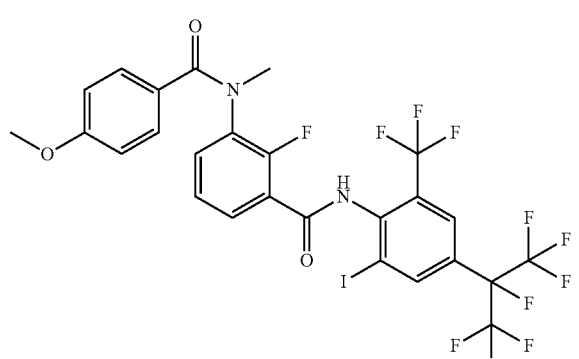 |
| 63 | 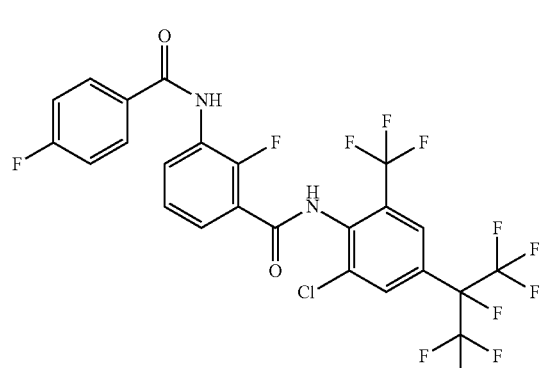 |

TABLE 241-continued
| Compound | Structure |
|---|---|
| 73 | 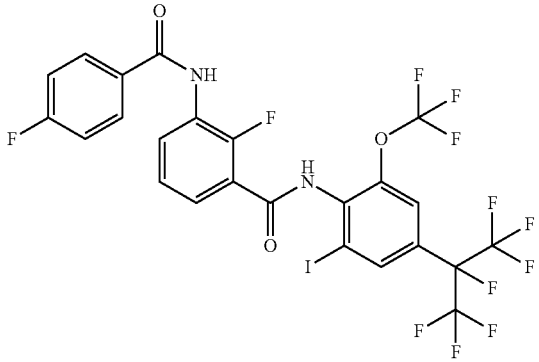 [SMILES: O=C(Nc1cccc(C(=O)Nc2c(I)cc(C(F)(C(F)(F)F)C(F)(F)F)cc2OC(F)(F)F)c1F)c1ccc(F)cc1] |
| 74 | 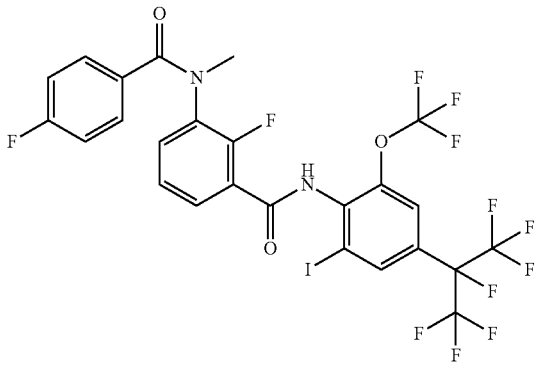 [SMILES: CN(C(=O)c1ccc(F)cc1)c1cccc(C(=O)Nc2c(I)cc(C(F)(C(F)(F)F)C(F)(F)F)cc2OC(F)(F)F)c1F] |
| 75 | 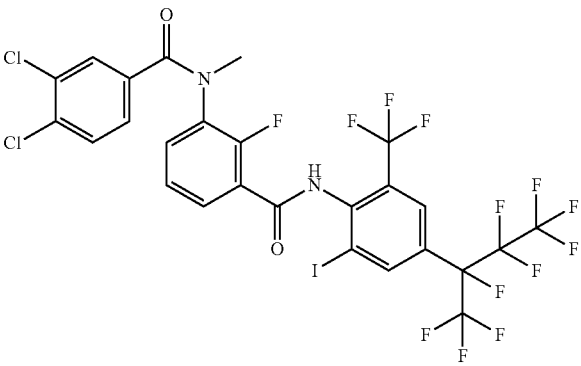 [SMILES: CN(C(=O)c1ccc(Cl)c(Cl)c1)c1cccc(C(=O)Nc2c(I)cc(C(F)(C(F)(F)F)C(F)(F)C(F)(F)F)cc2C(F)(F)F)c1F] |
| 76 | 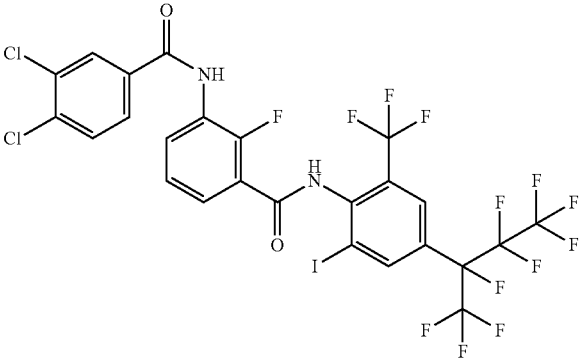 [SMILES: O=C(Nc1cccc(C(=O)Nc2c(I)cc(C(F)(C(F)(F)F)C(F)(F)C(F)(F)F)cc2C(F)(F)F)c1F)c1ccc(Cl)c(Cl)c1] |

TABLE 241-continued
| Compound | Structure |
|---|---|
| 77 | 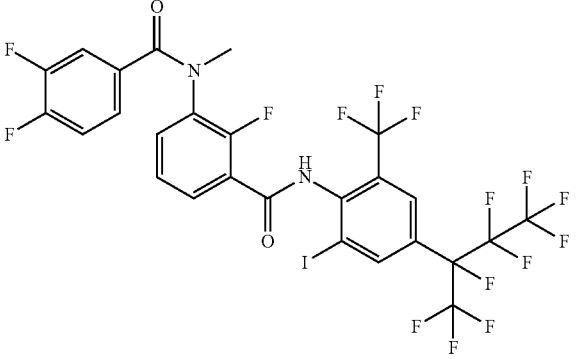 [SMILES: CN(C(=O)c1ccc(F)c(F)c1)c1cccc(C(=O)Nc2c(I)cc(C(F)(C(F)(F)F)C(F)(F)C(F)(F)F)cc2C(F)(F)F)c1F] |
| 78 | 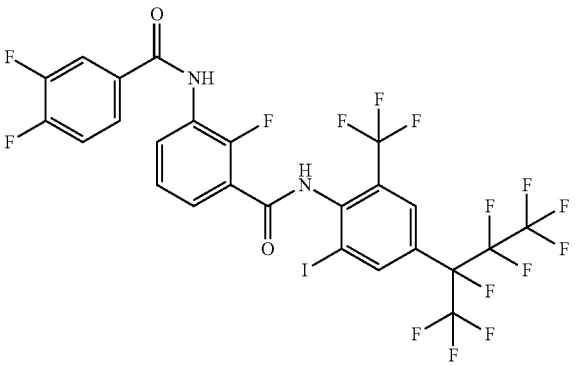 [SMILES: O=C(Nc1cccc(C(=O)Nc2c(I)cc(C(F)(C(F)(F)F)C(F)(F)C(F)(F)F)cc2C(F)(F)F)c1F)c1ccc(F)c(F)c1] |
| 79 | 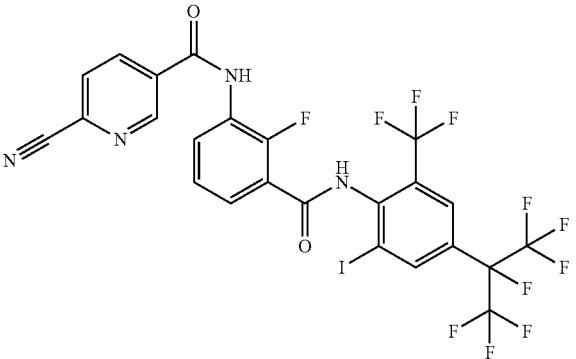 [SMILES: N#Cc1ccc(C(=O)Nc2cccc(C(=O)Nc3c(I)cc(C(F)(C(F)(F)F)C(F)(F)F)cc3C(F)(F)F)c2F)cn1] |
| 80 | 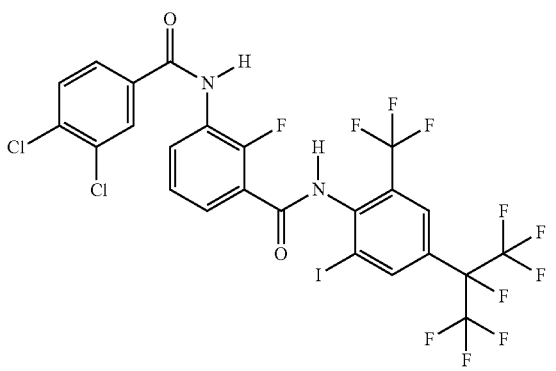 [SMILES: O=C(Nc1cccc(C(=O)Nc2c(I)cc(C(F)(C(F)(F)F)C(F)(F)F)cc2C(F)(F)F)c1F)c1ccc(Cl)c(Cl)c1] |

TABLE 241-continued
| Compound | Structure |
|---|---|
| 81 | 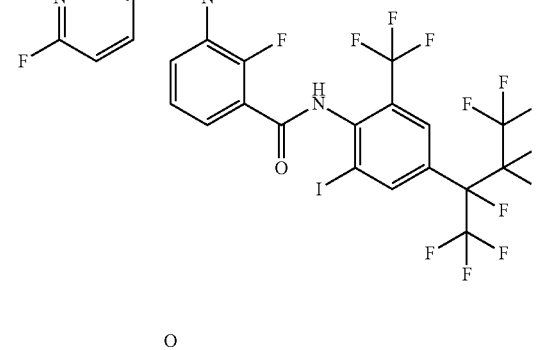 |
| 91 | 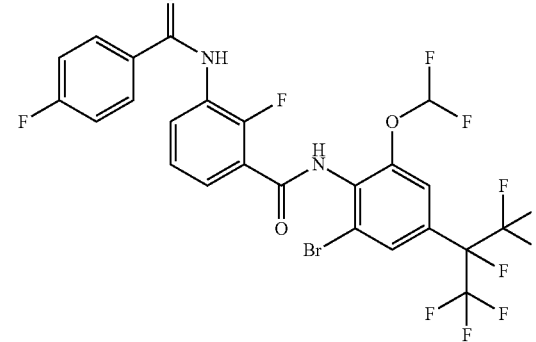 |
| 92 | 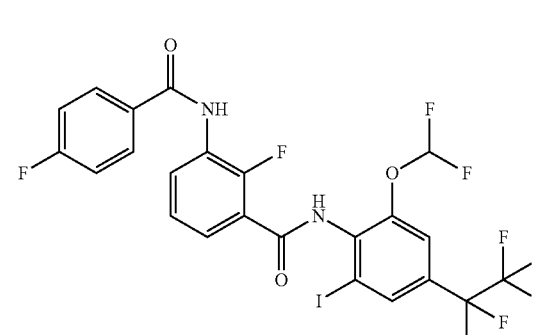 |
| 93 | 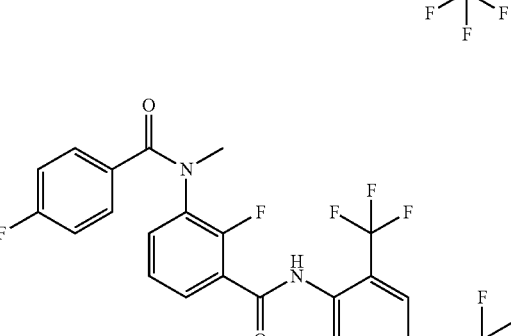 |

TABLE 241-continued

| Compound | Structure |
|---|---|
| 94 | 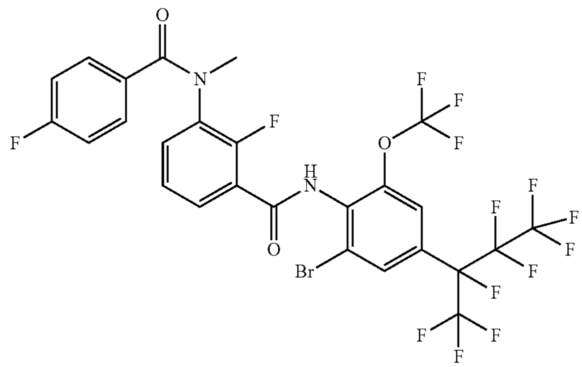 [SMILES: CN(C(=O)c1ccc(F)cc1)c1cccc(C(=O)Nc2c(Br)cc(C(F)(C(F)(F)F)C(F)(F)C(F)(F)F)cc2OC(F)(F)F)c1F] |
| 95 | 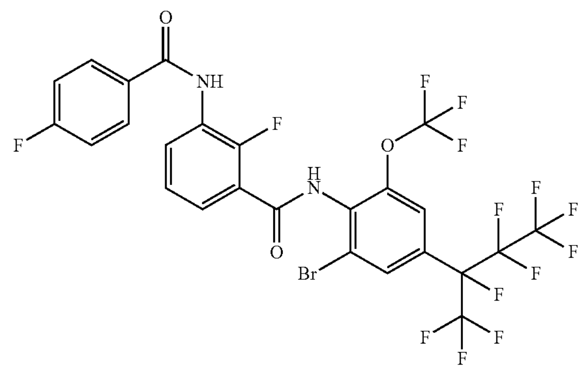 [SMILES: O=C(Nc1cccc(C(=O)Nc2c(Br)cc(C(F)(C(F)(F)F)C(F)(F)C(F)(F)F)cc2OC(F)(F)F)c1F)c1ccc(F)cc1] |
| 96 | 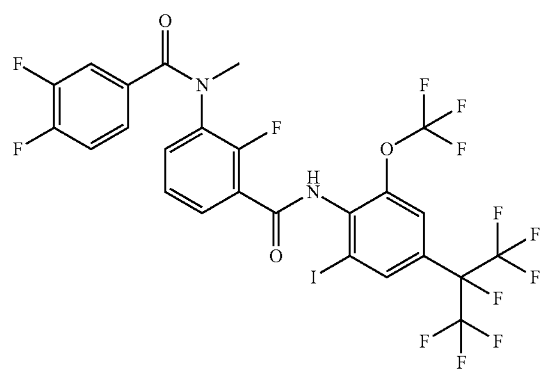 [SMILES: CN(C(=O)c1ccc(F)c(F)c1)c1cccc(C(=O)Nc2c(I)cc(C(F)(C(F)(F)F)C(F)(F)F)cc2OC(F)(F)F)c1F] |
| 97 | 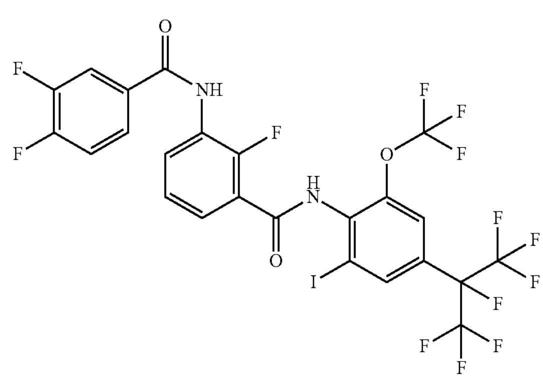 [SMILES: O=C(Nc1cccc(C(=O)Nc2c(I)cc(C(F)(C(F)(F)F)C(F)(F)F)cc2OC(F)(F)F)c1F)c1ccc(F)c(F)c1] |

TABLE 241-continued

| Compound | Structure |
| --- | --- |
| 98 | 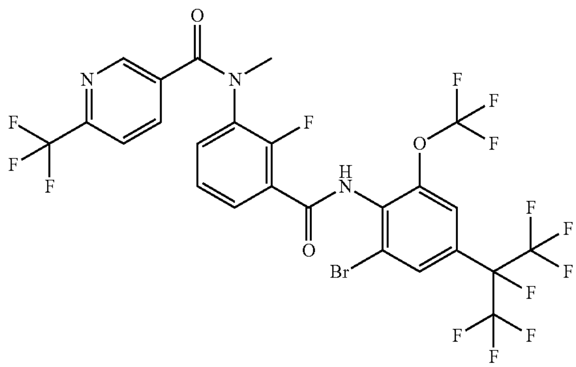 [SMILES: CN(C(=O)c1ccc(C(F)(F)F)nc1)c1cccc(C(=O)Nc2c(Br)cc(C(F)(C(F)(F)F)C(F)(F)F)cc2OC(F)(F)F)c1F] |
| 99 | 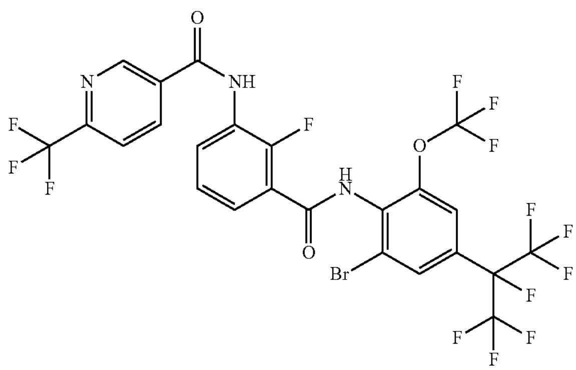 [SMILES: O=C(Nc1cccc(C(=O)Nc2c(Br)cc(C(F)(C(F)(F)F)C(F)(F)F)cc2OC(F)(F)F)c1F)c1ccc(C(F)(F)F)nc1] |
| 109 | 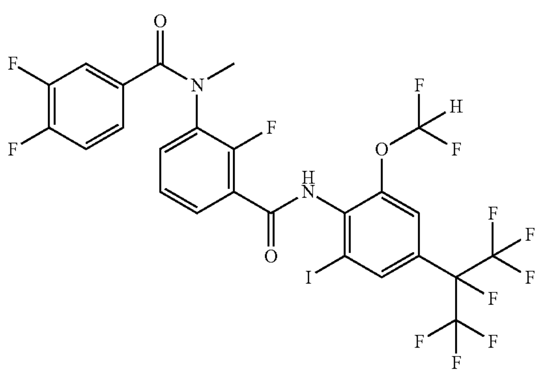 |
| 110 | 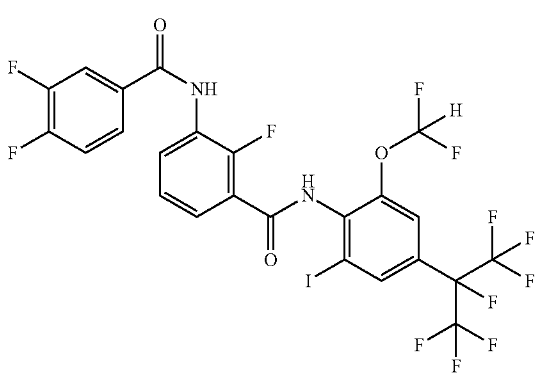 |

TABLE 241-continued

| Compound | Structure |
|---|---|
| 111 | 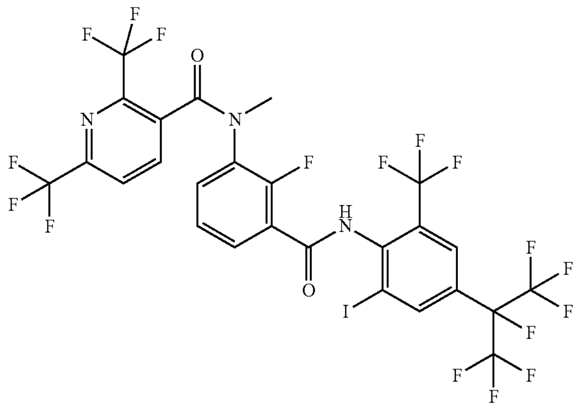 [SMILES: CN(C(=O)c1ccc(C(F)(F)F)nc1C(F)(F)F)c1cccc(C(=O)Nc2c(I)cc(C(F)(C(F)(F)F)C(F)(F)F)cc2C(F)(F)F)c1F] |
| 112 | 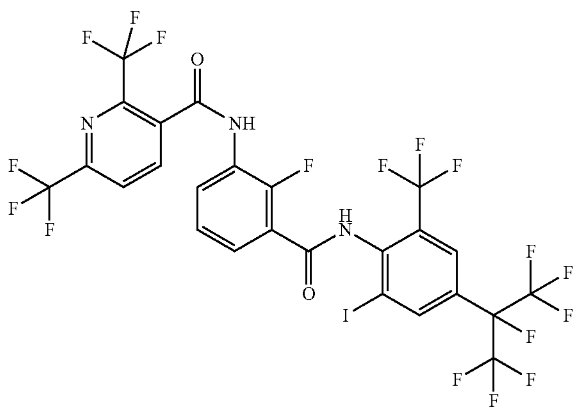 [SMILES: O=C(Nc1cccc(C(=O)Nc2c(I)cc(C(F)(C(F)(F)F)C(F)(F)F)cc2C(F)(F)F)c1F)c1ccc(C(F)(F)F)nc1C(F)(F)F] |
| 113 | 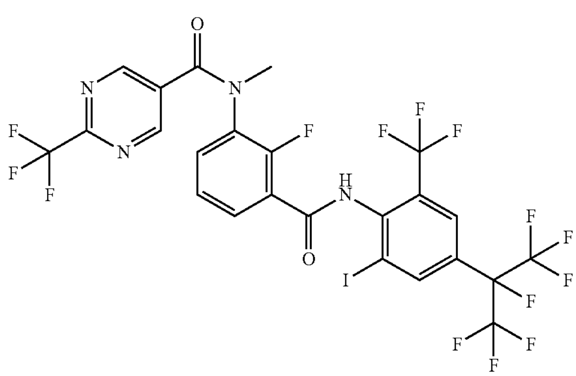 [SMILES: CN(C(=O)c1cnc(C(F)(F)F)nc1)c1cccc(C(=O)Nc2c(I)cc(C(F)(C(F)(F)F)C(F)(F)F)cc2C(F)(F)F)c1F] |
| 114 | 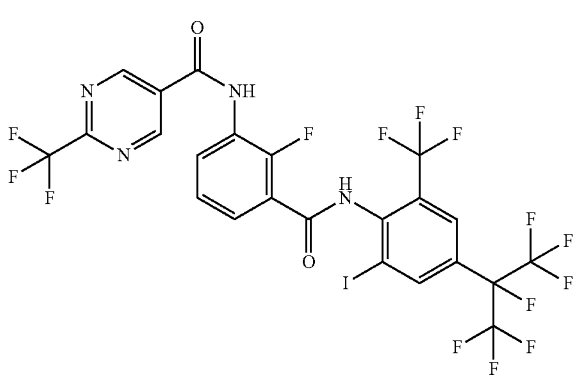 [SMILES: O=C(Nc1cccc(C(=O)Nc2c(I)cc(C(F)(C(F)(F)F)C(F)(F)F)cc2C(F)(F)F)c1F)c1cnc(C(F)(F)F)nc1] |

TABLE 241-continued

| Compound | Structure |
|---|---|
| 115 | 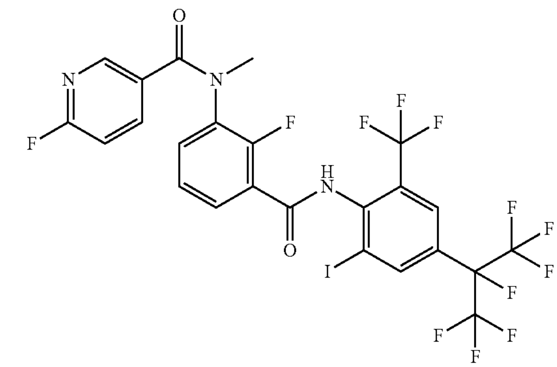 [SMILES: CN(C(=O)c1ccc(F)nc1)c1cccc(C(=O)Nc2c(I)cc(C(F)(C(F)(F)F)C(F)(F)F)cc2C(F)(F)F)c1F] |
| 116 | 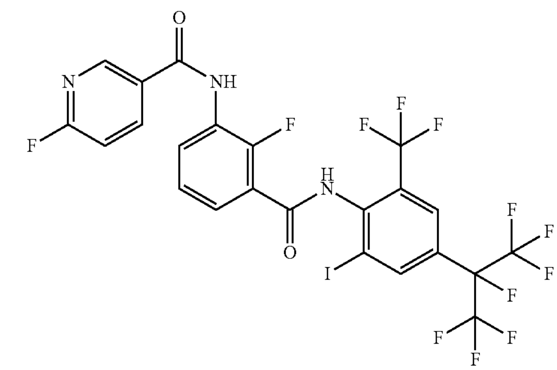 [SMILES: O=C(Nc1cccc(C(=O)Nc2c(I)cc(C(F)(C(F)(F)F)C(F)(F)F)cc2C(F)(F)F)c1F)c1ccc(F)nc1] |
| 117 | 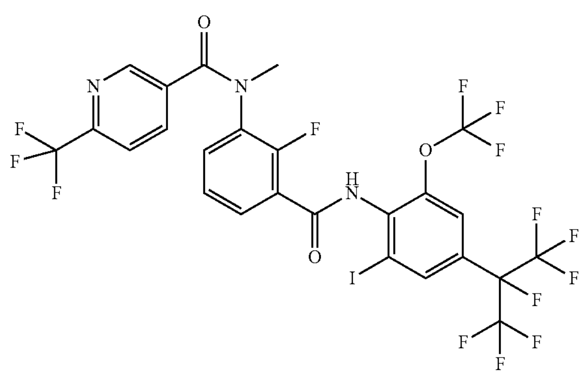 [SMILES: CN(C(=O)c1ccc(C(F)(F)F)nc1)c1cccc(C(=O)Nc2c(I)cc(C(F)(C(F)(F)F)C(F)(F)F)cc2OC(F)(F)F)c1F] |
| 10 | 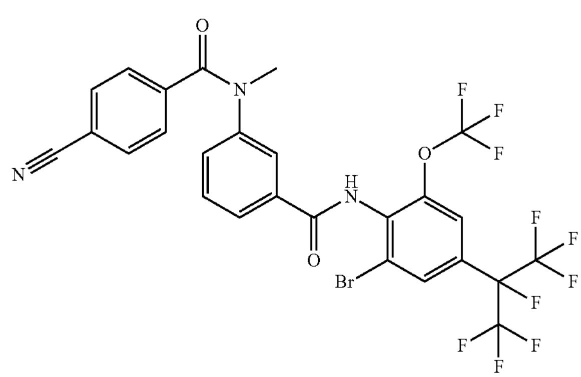 [SMILES: CN(C(=O)c1ccc(C#N)cc1)c1cccc(C(=O)Nc2c(Br)cc(C(F)(C(F)(F)F)C(F)(F)F)cc2OC(F)(F)F)c1] |

TABLE 241-continued

| Compound | Structure |
|---|---|
| 11 | 4-nitrobenzamide linked via NH to 3-position of benzamide; benzamide N—H connected to 2-bromo-6-(trifluoromethoxy)-4-(perfluoroethyl)phenyl |
| 12 | 4-fluorobenzamide linked via NH to 3-position of benzamide; benzamide N—H connected to 2-bromo-6-(trifluoromethoxy)-4-(perfluoroethyl)phenyl |
| 13 | 4-cyanobenzamide linked via NH to 3-position of 2-fluorobenzamide; benzamide N—H connected to 2-bromo-6-(trifluoromethoxy)-4-(perfluoroethyl)phenyl |
| 14 | 4-cyano-2-fluoro-N-methylbenzamide linked to 3-position of benzamide; benzamide N—H connected to 2-bromo-4,6-bis(perfluoroethyl)phenyl |

TABLE 241-continued
| Compound | Structure |
|---|---|
| 15 | 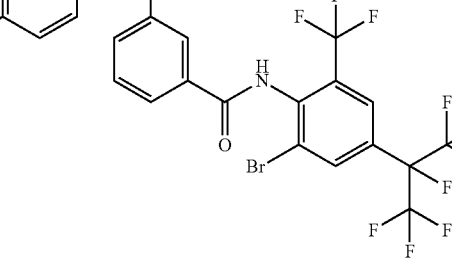 |
| 16 | 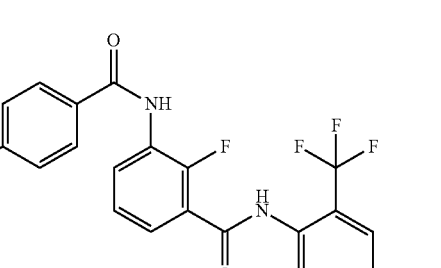 |
| 17 | 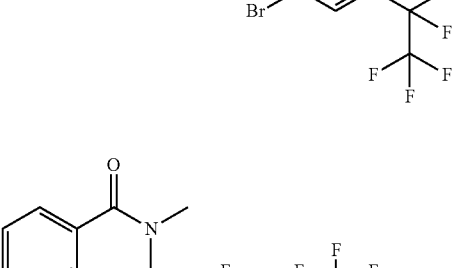 |
| 18 | 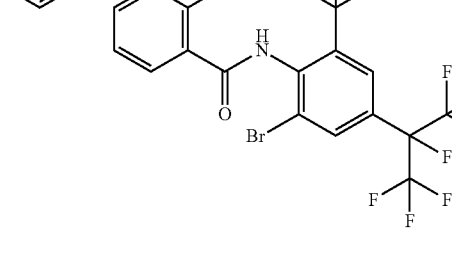 |

TABLE 241-continued

| Compound | Structure |
|---|---|
| 28 | 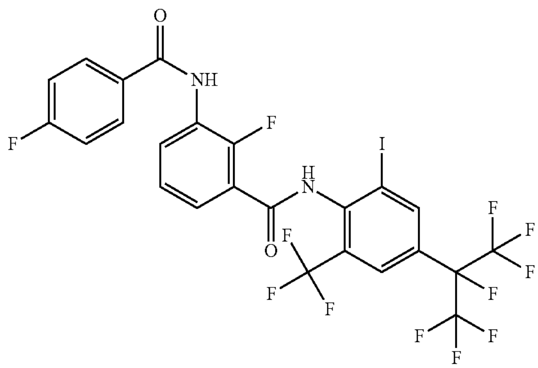 [SMILES: O=C(Nc1cccc(C(=O)Nc2c(I)cc(C(F)(C(F)(F)F)C(F)(F)F)cc2C(F)(F)F)c1F)c1ccc(F)cc1] |
| 29 | 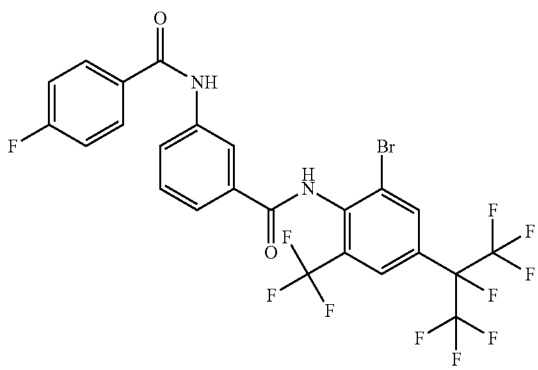 [SMILES: O=C(Nc1cccc(C(=O)Nc2c(Br)cc(C(F)(C(F)(F)F)C(F)(F)F)cc2C(F)(F)F)c1)c1ccc(F)cc1] |
| 30 | 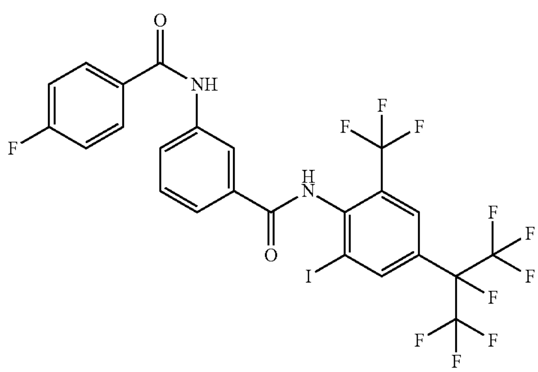 [SMILES: O=C(Nc1cccc(C(=O)Nc2c(I)cc(C(F)(C(F)(F)F)C(F)(F)F)cc2C(F)(F)F)c1)c1ccc(F)cc1] |
| 31 | 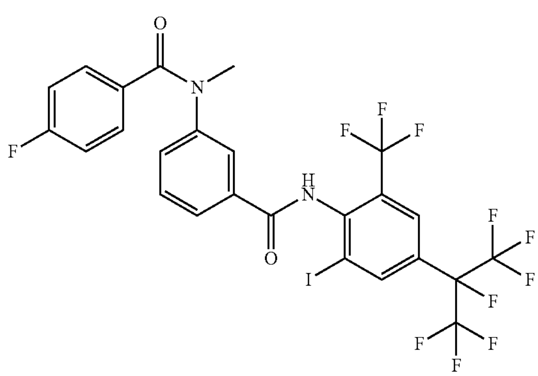 [SMILES: CN(C(=O)c1ccc(F)cc1)c1cccc(C(=O)Nc2c(I)cc(C(F)(C(F)(F)F)C(F)(F)F)cc2C(F)(F)F)c1] |

TABLE 241-continued

| Compound | Structure |
|---|---|
| 32 | 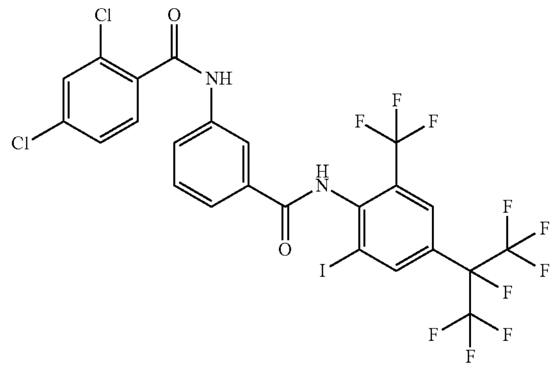 [SMILES: O=C(Nc1c(I)cc(C(F)(C(F)(F)F)C(F)(F)F)cc1C(F)(F)F)c1cccc(NC(=O)c2ccc(Cl)cc2Cl)c1] |
| 33 | 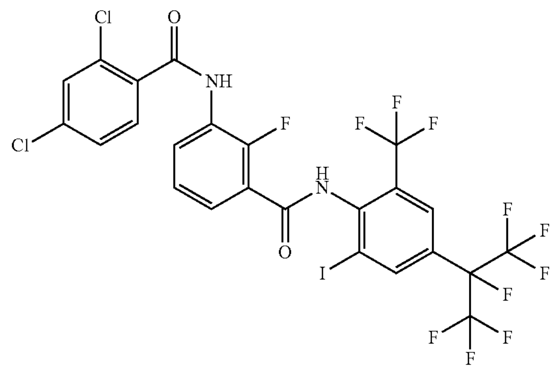 [SMILES: O=C(Nc1cccc(C(=O)Nc2c(I)cc(C(F)(C(F)(F)F)C(F)(F)F)cc2C(F)(F)F)c1F)c1ccc(Cl)cc1Cl] |
| 34 | 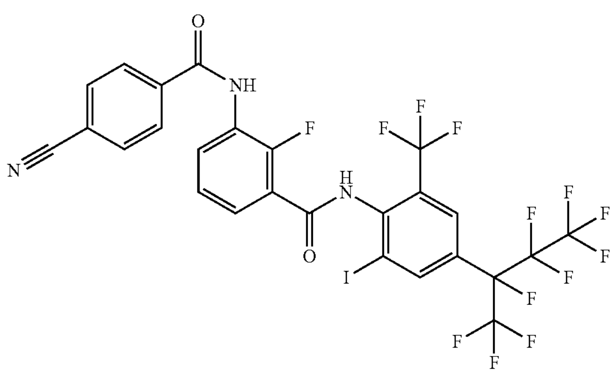 [SMILES: N#Cc1ccc(C(=O)Nc2cccc(C(=O)Nc3c(I)cc(C(F)(C(F)(F)F)C(F)(F)C(F)(F)F)cc3C(F)(F)F)c2F)cc1] |
| 35 | 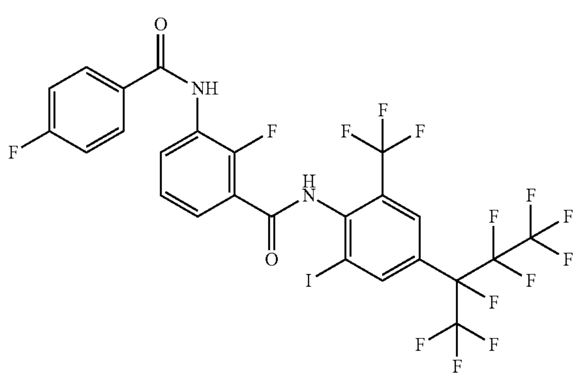 [SMILES: O=C(Nc1cccc(C(=O)Nc2c(I)cc(C(F)(C(F)(F)F)C(F)(F)C(F)(F)F)cc2C(F)(F)F)c1F)c1ccc(F)cc1] |

TABLE 241-continued

| Compound | Structure |
| --- | --- |
| 36 | 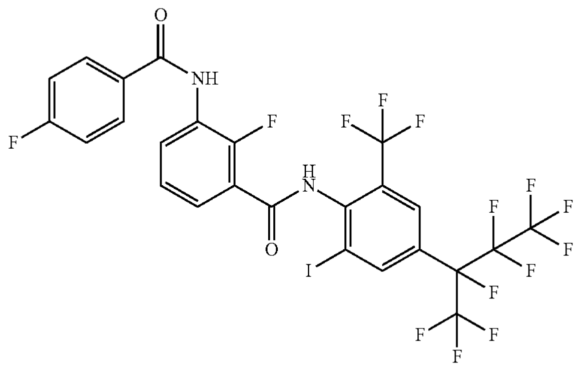 [SMILES: O=C(Nc1cccc(C(=O)Nc2c(I)cc(C(F)(C(F)(F)F)C(F)(F)C(F)(F)F)cc2C(F)(F)F)c1F)c1ccc(F)cc1] |
| 46 | 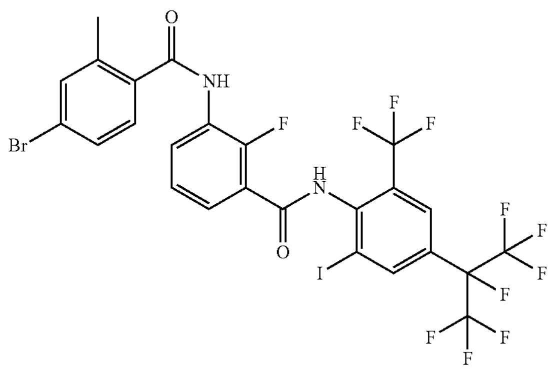 [SMILES: Cc1cc(Br)ccc1C(=O)Nc1cccc(C(=O)Nc2c(I)cc(C(F)(C(F)(F)F)C(F)(F)F)cc2C(F)(F)F)c1F] |
| 47 | 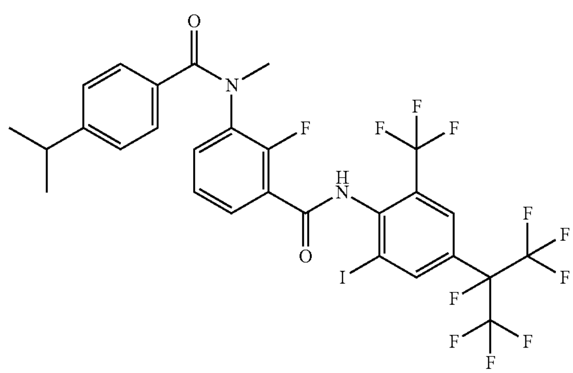 [SMILES: CC(C)c1ccc(C(=O)N(C)c2cccc(C(=O)Nc3c(I)cc(C(F)(C(F)(F)F)C(F)(F)F)cc3C(F)(F)F)c2F)cc1] |
| 48 | 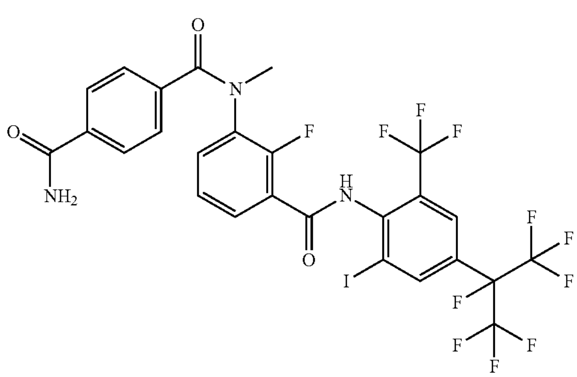 [SMILES: CN(C(=O)c1ccc(C(N)=O)cc1)c1cccc(C(=O)Nc2c(I)cc(C(F)(C(F)(F)F)C(F)(F)F)cc2C(F)(F)F)c1F] |

TABLE 241-continued

| Compound | Structure |
| --- | --- |
| 49 | 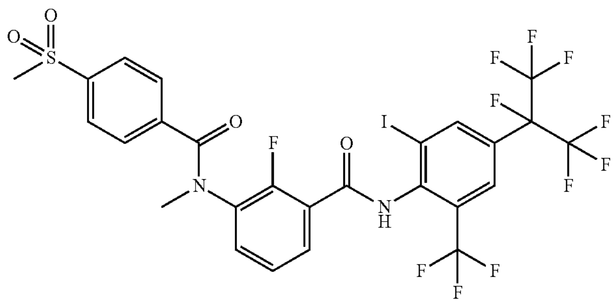 [SMILES: CN(C(=O)c1ccc(S(C)(=O)=O)cc1)c1cccc(C(=O)Nc2c(I)cc(C(F)(C(F)(F)F)C(F)(F)F)cc2C(F)(F)F)c1F] |
| 50 | 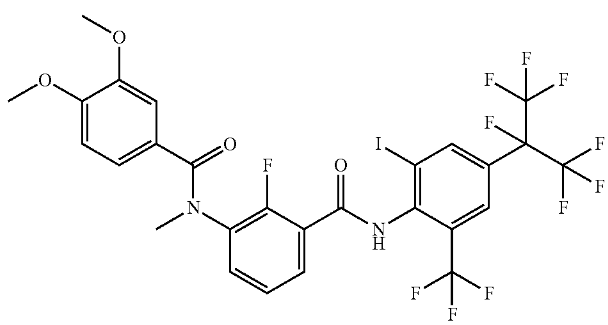 [SMILES: COc1ccc(C(=O)N(C)c2cccc(C(=O)Nc3c(I)cc(C(F)(C(F)(F)F)C(F)(F)F)cc3C(F)(F)F)c2F)cc1OC] |
| 51 | 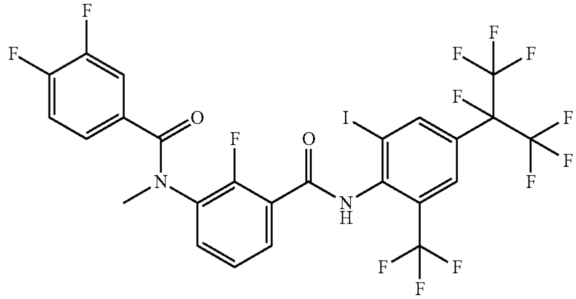 [SMILES: CN(C(=O)c1ccc(F)c(F)c1)c1cccc(C(=O)Nc2c(I)cc(C(F)(C(F)(F)F)C(F)(F)F)cc2C(F)(F)F)c1F] |
| 52 | 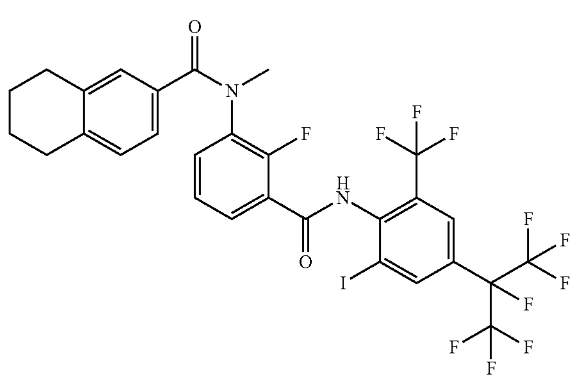 [SMILES: CN(C(=O)c1ccc2c(c1)CCCC2)c1cccc(C(=O)Nc2c(I)cc(C(F)(C(F)(F)F)C(F)(F)F)cc2C(F)(F)F)c1F] |

TABLE 241-continued
| Compound | Structure |
|---|---|
| 53 | 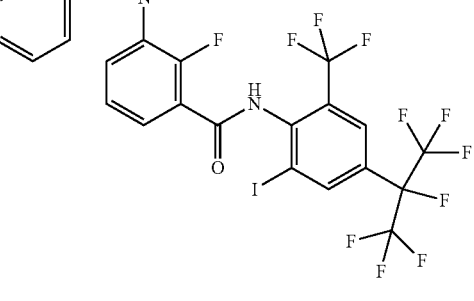 |
| 54 | 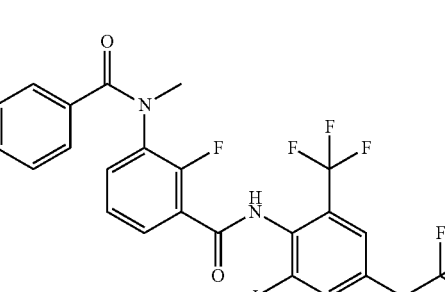 |
| 64 | 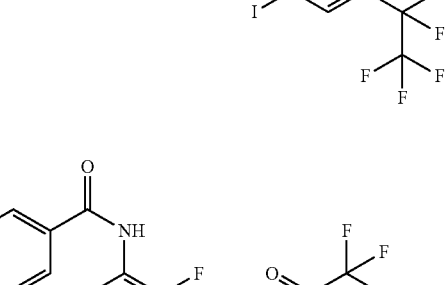 |
| 65 | 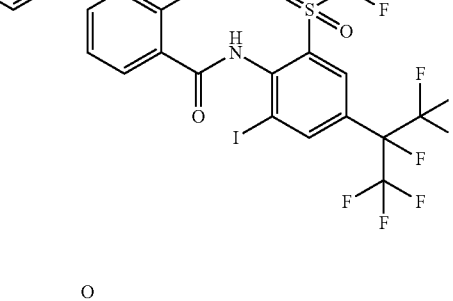 |

TABLE 241-continued

| Compound | Structure |
|---|---|
| 66 | *(chemical structure)* |
| 67 | *(chemical structure)* |
| 68 | *(chemical structure)* |

TABLE 241-continued
| Compound | Structure |
|---|---|
| 69 | 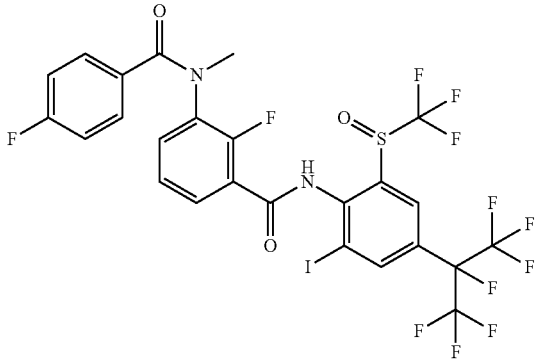 [SMILES: CN(C(=O)c1ccc(F)cc1)c1cccc(C(=O)Nc2c(I)cc(C(F)(C(F)(F)F)C(F)(F)F)cc2S(=O)C(F)(F)F)c1F] |
| 70 | 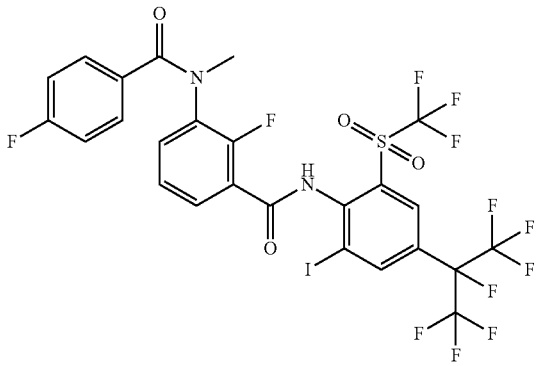 [SMILES: CN(C(=O)c1ccc(F)cc1)c1cccc(C(=O)Nc2c(I)cc(C(F)(C(F)(F)F)C(F)(F)F)cc2S(=O)(=O)C(F)(F)F)c1F] |
| 71 | 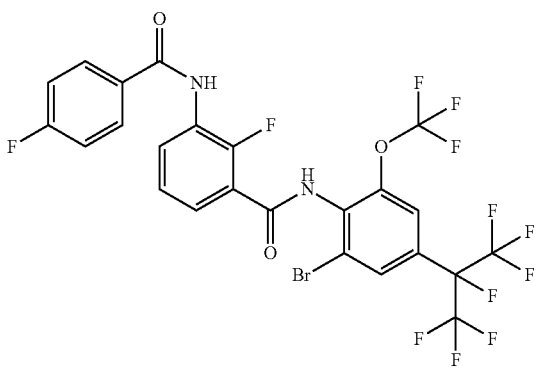 [SMILES: O=C(Nc1cccc(C(=O)Nc2c(Br)cc(C(F)(C(F)(F)F)C(F)(F)F)cc2OC(F)(F)F)c1F)c1ccc(F)cc1] |
| 72 | 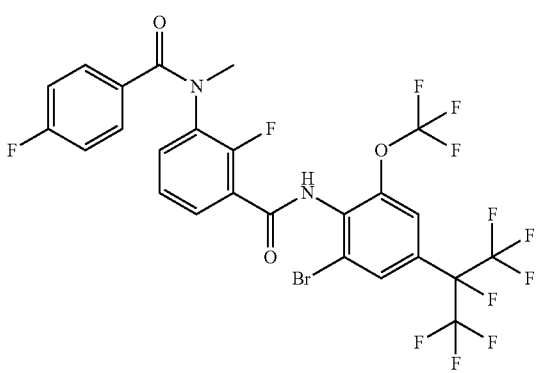 [SMILES: CN(C(=O)c1ccc(F)cc1)c1cccc(C(=O)Nc2c(Br)cc(C(F)(C(F)(F)F)C(F)(F)F)cc2OC(F)(F)F)c1F] |

TABLE 241-continued

| Compound | Structure |
|---|---|
| 82 | 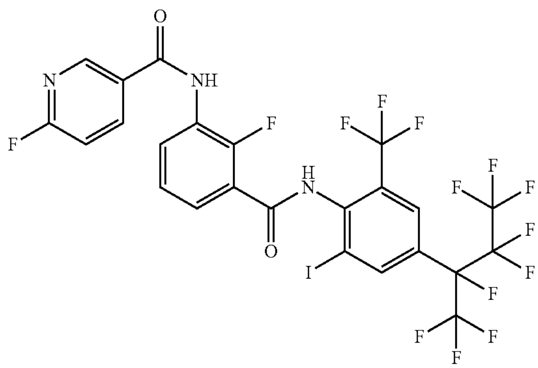 [SMILES: O=C(Nc1cccc(C(=O)Nc2c(I)cc(C(F)(C(F)(F)F)C(F)(F)C(F)(F)F)cc2C(F)(F)F)c1F)c1ccc(F)nc1] |
| 83 | 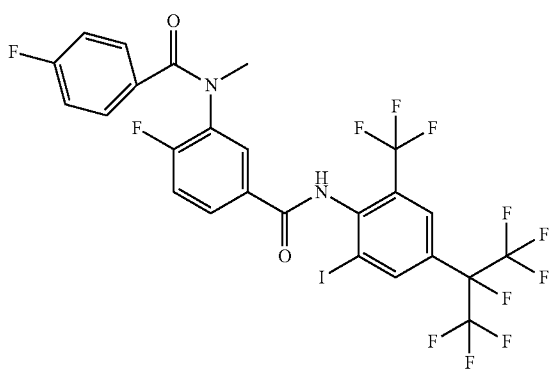 [SMILES: CN(C(=O)c1ccc(F)cc1)c1cc(C(=O)Nc2c(I)cc(C(F)(C(F)(F)F)C(F)(F)F)cc2C(F)(F)F)ccc1F] |
| 84 | 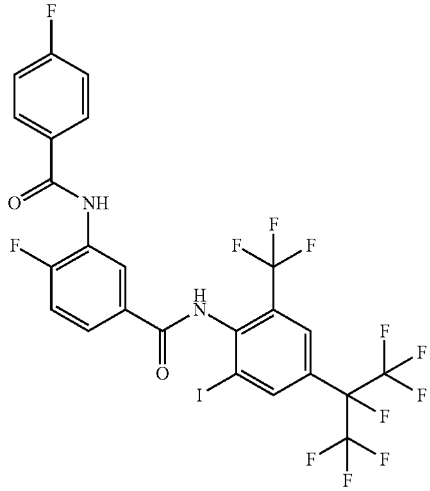 [SMILES: O=C(Nc1cc(C(=O)Nc2c(I)cc(C(F)(C(F)(F)F)C(F)(F)F)cc2C(F)(F)F)ccc1F)c1ccc(F)cc1] |

TABLE 241-continued

| Compound | Structure |
|---|---|
| 85 | 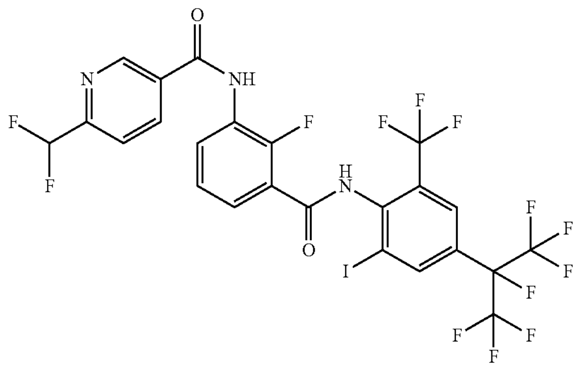 [SMILES: O=C(Nc1cccc(C(=O)Nc2c(I)cc(C(F)(C(F)(F)F)C(F)(F)F)cc2C(F)(F)F)c1F)c1ccc(C(F)F)nc1] |
| 86 | 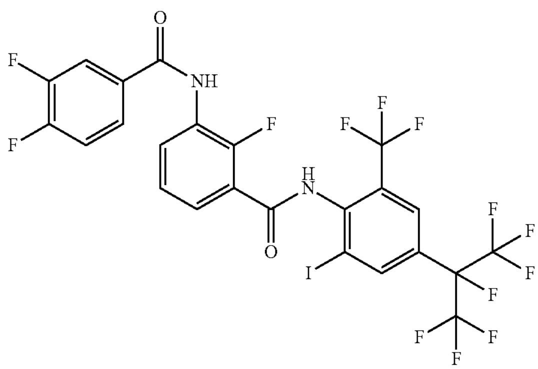 [SMILES: O=C(Nc1cccc(C(=O)Nc2c(I)cc(C(F)(C(F)(F)F)C(F)(F)F)cc2C(F)(F)F)c1F)c1ccc(F)c(F)c1] |
| 87 | 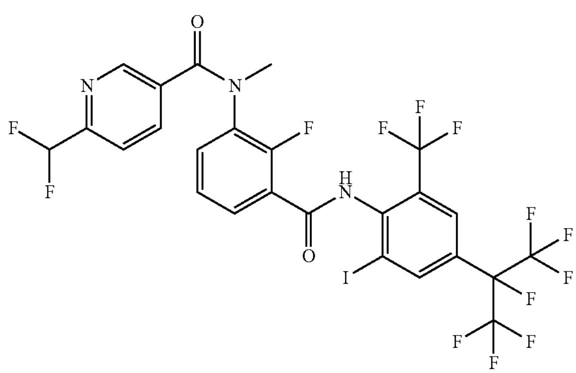 [SMILES: CN(C(=O)c1ccc(C(F)F)nc1)c1cccc(C(=O)Nc2c(I)cc(C(F)(C(F)(F)F)C(F)(F)F)cc2C(F)(F)F)c1F] |
| 88 | 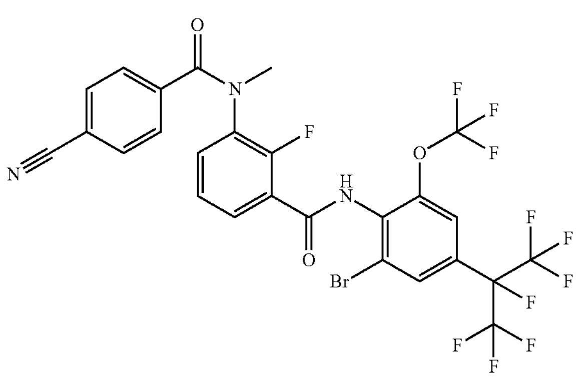 [SMILES: CN(C(=O)c1ccc(C#N)cc1)c1cccc(C(=O)Nc2c(Br)cc(C(F)(C(F)(F)F)C(F)(F)F)cc2OC(F)(F)F)c1F] |

TABLE 241-continued

| Compound | Structure |
|---|---|
| 89 | 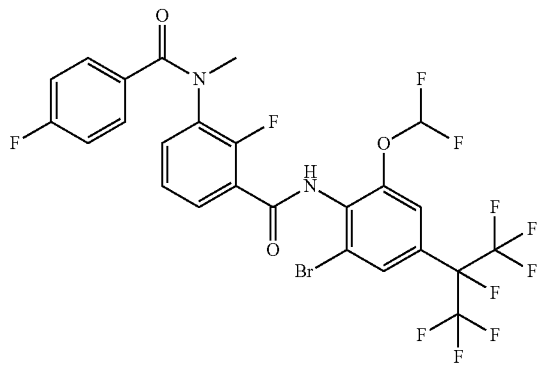 [SMILES: CN(C(=O)c1ccc(F)cc1)c1cccc(C(=O)Nc2c(Br)cc(C(F)(C(F)(F)F)C(F)(F)F)cc2OC(F)F)c1F] |
| 90 | 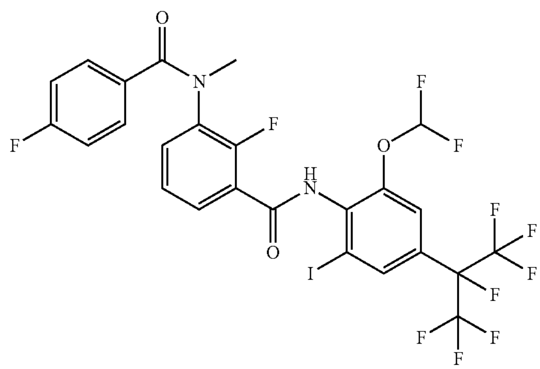 [SMILES: CN(C(=O)c1ccc(F)cc1)c1cccc(C(=O)Nc2c(I)cc(C(F)(C(F)(F)F)C(F)(F)F)cc2OC(F)F)c1F] |
| 100 | 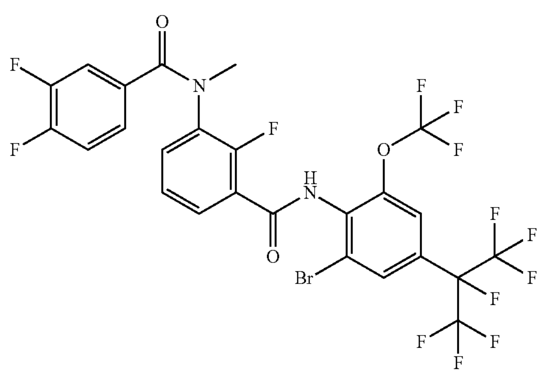 |
| 101 | 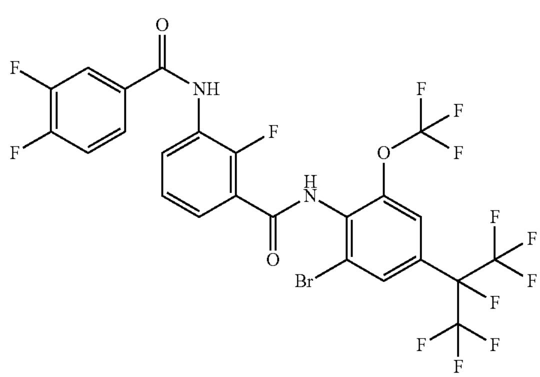 [SMILES: O=C(Nc1cccc(C(=O)Nc2c(Br)cc(C(F)(C(F)(F)F)C(F)(F)F)cc2OC(F)(F)F)c1F)c1ccc(F)c(F)c1] |

TABLE 241-continued

| Compound | Structure |
|---|---|
| 102 | (structure) |
| 103 | (structure) |
| 104 | (structure) |
| 105 | (structure) |

TABLE 241-continued

| Compound | Structure |
|---|---|
| 106 | 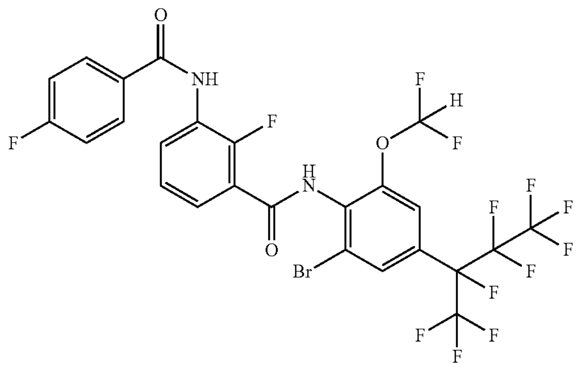 [SMILES: O=C(Nc1cccc(C(=O)Nc2c(Br)cc(C(F)(C(F)(F)F)C(F)(F)C(F)(F)F)cc2OC(F)F)c1F)c1ccc(F)cc1] |
| 107 | 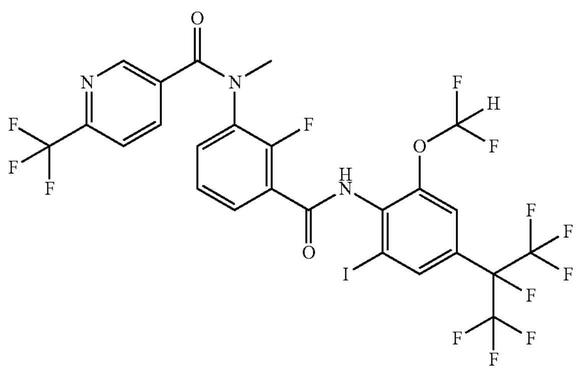 [SMILES: CN(C(=O)c1ccc(C(F)(F)F)nc1)c1cccc(C(=O)Nc2c(I)cc(C(F)(C(F)(F)F)C(F)(F)F)cc2OC(F)F)c1F] |
| 108 | 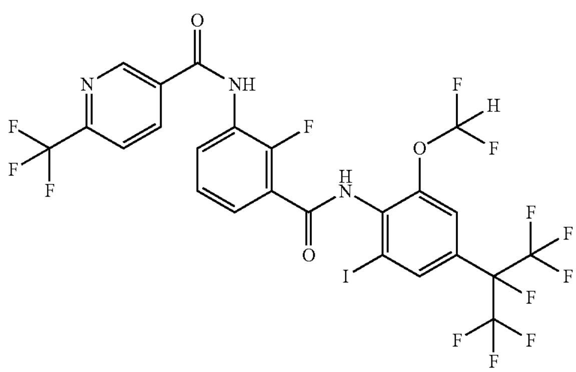 |
| 118 | 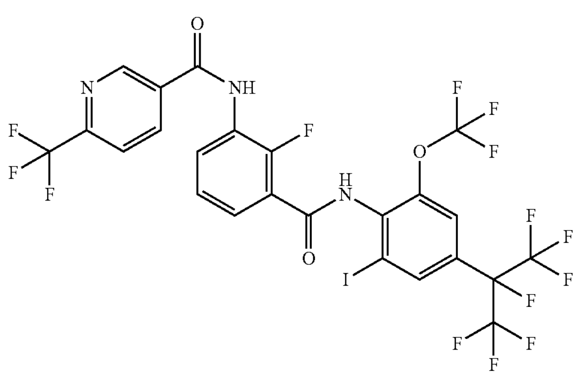 [SMILES: O=C(Nc1cccc(C(=O)Nc2c(I)cc(C(F)(C(F)(F)F)C(F)(F)F)cc2OC(F)(F)F)c1F)c1ccc(C(F)(F)F)nc1] |

TABLE 241-continued

| Compound | Structure |
|---|---|
| 119 | (structure shown) |

Particularly preferred compounds represented by Formula (1) for use according to the present invention include the following compounds:

2-fluoro-3-(4-fluoro-N-methylbenzamido)-N-(2-iodo-4-(perfluoropropan-2-yl)-6-(trifluoromethyl)phenyl)benzamide 2-fluoro-3-(4-fluorobenzamido)-N-(2-iodo-4-(perfluoropropan-2-yl)-6-(trifluoromethyl)phenyl)benzamide.

N-(2-fluoro-3-((2-iodo-4-(perfluoropropan-2-yl)-6-(trifluoromethyl)phenyl)carbamoyl)phenyl)-6-(trifluoromethyl) nicotinamide, N-(2-fluoro-3-((2-iodo-4-(perfluoropropan-2-yl)-6-(trifluoromethyl)phenyl)carbamoyl)phenyl)-N-methyl-6-(trifluoromethyl)nicotinamide, 6-fluoro-N-(2-fluoro-3-((2-iodo-4-(perfluoropropan-2-yl)-6-(trifluoromethyl)phenyl)carbamoyl)phenyl)nicotinamide, 6-fluoro-N-(2-fluoro-3-((2-iodo-4-(perfluoropropan-2-yl)-6-(trifluoromethyl)phenyl)carbamoyl)phenyl)-N-methylnicotinamide, 2-fluoro-3-(4-fluoro-N-methylbenzamido)-N-(2-iodo-4-(perfluoropropan-2-yl)-6-((trifluoromethyl)sulfonyl)phenyl)benzamide, 2-fluoro-3-(4-fluorobenzamido)-N-(2-iodo-4-(perfluoropropan-2-yl)-6-((trifluoromethyl)sulfonyl)phenyl)benzamide.

The compound represented by Formula (1) may be in the form of a solid, or in the form of a solvate, in particular a hydrate. The compound in the form of a solvate, particularly hydrate, is also embraced by the invention.

Compounds represented by Formula (1) can be prepared using methods known in the art, see e.g. WO 2005/073165, WO 2010/018714, WO 2011/093415 as well as WO2010/013567 and WO 2010/018857. Exemplary synthesis methods will be detailed in Examples 1 to 9.

In the animal health field, i.e. in the field of veterinary medicine, the compound represented by Formula (1) is active against animal parasites, in particular ectoparasites or endoparasites. The term endoparasite includes in particular helminths and protozoae, such as coccidia. Ectoparasites are typically and preferably arthropods, in particular insects or acarids. Due to the toxicity of the compound represented by Formula (1) against animal parasites, the compound represented by Formula (1) may be used to control the animal parasites. In particular, the compound represented by Formula (1) has a prolonged effect with respect to control of ectoparasites, as demonstrated in the working examples described later. The prolonged effect may provide, for example, at least 50% reduction (more preferably at least 60% reduction, still more preferably at least 70% reduction, further more preferably at least 80%, and particularly preferably at least 90%) in the number of live pests compared to an untreated control for, for example, at least 16 days (more preferably at least 23 days, and still more preferably at least 30 days). The test employed for determining the prolonged effect may be conducted by reference to Test Examples E and F described later.

In the field of veterinary medicine, the compound represented by Formula (1) has properties suitable for controlling parasites which occur in animal breeding and animal husbandry in livestock, breeding, zoo, laboratory, experimental and domestic animals, and the compound represented by Formula (1) has low toxicity against warm blooded animals. They are active against all or specific stages of development of the parasites.

According to an embodiment, a prolonned ectoparasite-controlling agent for an animal represented by Formula (1) is provided. In other words, the compound represented by Formula (1) can suitably be used as a prologned ectoparasite-controlling agent for an animal. The prolonged ectoparasite-controlling agent may have a chemical structure in which: each of $A_1$ and $A_3$ independently represents a C—$X_1$ group; $A_2$ represent a nitrogen atom or a C—$X_1$ group; $A_4$ represents a C—$X_1$ group; $R_1$ represents a hydrogen atom or a $C_1$-$C_4$ alkyl group; $R_2$ represents a trifluoromethyl group: X represents halogen atom or a $C_1$-$C_4$ haloalkyl group; $X_1$ represents a hydrogen atom; each of $X_2$ and $X_4$ represents a fluorine atom; $X_3$ represents a hydrogen atom; $X_5$ represents a bromine atom or an iodine atom; and Y represents a single bond or a sulfonyl group. The prolonged ectoparasite-controlling agent may be systemically applied, and the application may be performed via at least one of an oral route, a parenteral route, or a dermal route.

According to another embodiment, a preparation for systemic application for use in prolonged control of an ectoparasite on an animal is provided, the preparation including the compound represented by Formula (1). The preparation may be for at least one of oral use, parenteral use or dermal use. The preparation may be a single-dose preparation. In the present disclosure, the term "preparation" and the term "formulation" are used substantially interchangeably.

According to another embodiment, a method for prolonged control of an ectoparasite on an animal is provided, the method including systemically applying the compound represented by Formula (1). According to another embodiment, use of the compound represented by Formula (1) for preparing a medicament for prolonged control of an ectoparasite on an animal is provided, in which the medicament is applied systemically to the animal. According to still another embodiment, use of the compound represented by Formula (1) for prolonged control of an ectoparasite on an animal is provided, in which the medicament is applied systemically to the animal.

Agricultural livestock that may be treated with the compound represented by Formula (1) to control parasites include, for example, mammals, such as, sheep, goats, horses, donkeys, camels, buffaloes, rabbits, reindeers, fallow deers, and in particular cattle and pigs; or poultry, such as turkeys, ducks, geese, and in particular chickens; or fish or crustaceans, e.g. in aquaculture; or, as the case may be, insects such as bees.

Domestic animals that may be treated with the compound represented by Formula (1) to control parasites include, for example, mammals, such as hamsters, guinea pigs, rats, mice, chinchillas, ferrets or in particular dogs, cats; cage birds; reptiles; amphibians or aquarium fish.

According to an embodiment, the compound represented by Formula (1) is administered to a mammal. According to another embodiment, the compound represented by Formula (1) is administered to a bird, for example a cage bird or in particular poultry.

By using the compound represented by Formula (1) to control animal parasites, it is possible to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling", as used herein with regard to the animal health field, means reduction of the incidence of the respective parasite in an animal infected with such parasites to innocuous levels. More specifically, "controlling", as used herein, means efficacy in killing the respective parasite, inhibiting its growth, or inhibiting its proliferation.

Exemplary arthropods that may be controlled using the compound represented by Formula (1) include, without any limitation:

from the order of the Anoplurida, for example, *Haematopinus* spp., *Linognathus* spp., *Pediculus* spp., *Phtirus* spp., *Solenopotes* spp.;
from the order of the Mallophagida and the suborders Amblycerina and Ischnocerina, for example *Bovicola* spp., *Damalina* spp., *Felicola* spp., *Lepikentron* spp., *Menopon* spp., *Trichodectes* spp., *Trimenopon* spp., *Trinoton* spp., and *Werneckiella* spp.;
from the order of the Diptera and the suborders Nematocerina and Brachycerina, for example *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., and *Wohlfahrtia* spp.
from the order of the Siphonapterida, for example *Ceratophyllus* spp.; *Ctenocephalides* spp., *Pulex* spp., *Tunga* spp., *Xenopsylla* spp.;
from the order of the Heteropterida, for example *Cimex* spp., *Panstrongylus* spp., *Rhodnius* spp., and *Triatoma* spp.; as well as
nuisance and hygiene pests from the order of the Blattarida.

Further, exemplary arthropods that may be controlled using the compound represented by Formula (1) include the following acari, without any limitation:

from the subclass of the Acari (Acarina) and the order of the Metastigmata, for example, from the family of argasidae like *Argas* spp., *Ornithodorus* spp., *Otobius* spp., from the family of Ixodidae like *Amblyomma* spp., *Dermacentor* spp., *Haemaphysalis* spp., *Hyalomma* spp., *Ixodes* spp., *Rhipicephalus* (*Boophilus*) spp, *Rhipicephalus* spp. (the original genus of multi host ticks); from the order of mesostigmata like *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (Prostigmata), for example *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of the Acaridida (Astigmata), for example *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., and *Tyrophagus* spp.

Exemplary parasitic protozoa that may be controlled using the compound represented by Formula (1) include, without any limitation:

Mastigophora (*Flagellata*) such as:
Metamonada: from the order Diplomonadida, for example, *Giardia* spp. and *Spironucleus* spp.,
Parabasala: from the order Trichomonadida, for example, *Histomonas* spp., *Pentatrichomonas* spp., *Tetratrichomonas* spp., *Trichomonas* spp., and *Tritrichomonas* spp., and
Euglenozoa: from the order Trypanosomatida, for example, *Leishmania* spp. and *Trypanosoma* spp.;
Sarcomastigophora (Rhizopoda), such as Entamoebidae, for example, *Entamoeba* spp., Centramoebidae, for example, *Acanthamoeba* sp., and Euamoebidae, e.g. *Hartmanella* sp.;
Alveolata such as Apicomplexa (Sporozoa): e.g.
*Cryptosporidium* spp.,
from the order Eimeriida, for example, *Besnoitia* spp., *Cystoisospora* spp., *Eimeria* spp., *Hammondia* spp., *Isospora* spp., *Neospora* spp., *Sarcocystis* spp., and *Toxoplasma* spp.,
from the order Adeleida e.g. *Hepatozoon* spp., *Klossiella* spp.; from the order Haemosporida e.g. *Leucocytozoon* spp., *Plasmodium* spp.,
from the order Piroplasmida e.g. *Babesia* spp., *Ciliophora* spp., *Echinozoon* spp., *Theileria* spp.; from the order Vesibuliferida e.g. *Balantidium* spp., and *Buxtonella* spp., and
*Microspora* such as *Encephalitozoon* spp., *Enterocytozoon* spp., *Globidium* spp., *Nosema* spp., and furthermore, e.g. *Myxozoa* spp.

Helminths pathogenic for humans or animals that may be controlled using the compound represented by Formula (1) include, for example, acanthocephala, nematodes, pentastoma and platyhelmintha (e.g. monogenea, cestodes and trematodes). Exemplary helminths that may be controlled using the compound represented by Formula (1) include, without any limitation:

Monogenea: e.g.: *Dactylogyrus* spp., *Gyrodactylus* spp., *Microbothrium* spp., *Polystoma* spp., *Troglocephalus* spp.;

Cestodes, including:
from the order of the Pseudophyllidea, for example, *Bothridium* spp., *Diphyllobothrium* spp., *Diplogonoporus* spp., *Ichthyobothrium* spp., *Ligula* spp., *Schistocephalus* spp., and *Spirometra* spp.,
from the order of the Cyclophyllida, for example, *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., and *Thysanosoma* spp.;

Trematodes, including:
from the class of the Digenea, for example, *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., and *Typhlocoelum* spp.;

Nematodes, including:
from the order of the Trichinellida, for example, *Capillaria* spp., *Eucoleus* spp., *Paracapillaria* spp., *Trichinella* spp., *Trichomosoides* spp., *Trichuris* spp.,
from the order of the Tylenchida, for example, *Micronema* spp., *Parastrongyloides* spp., *Strongyloides* spp.,
from the order of the Rhabditina, for example, *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.
from the order of the Spirurida, for example, *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acantocephala, including:
from the order of the Oligacanthorhynchida, for example, *Macracanthorhynchus* spp., and *Prosthenorchis* spp.,
from the order of the Moniliformida, for example, *Moniliformis* spp.,
from the order of the Polymorphida, for example, *Filicollis* spp.,
from the order of the Echinorhynchida, for example, *Acanthocephalus* spp., *Echinorhynchus* spp., *Leptorhynchoides* spp.; and Pentastoma, including:
from the order of the Porocephalida, for example. *Linguatula* spp.

In the veterinary field and in animal keeping, the administration of the compound represented by Formula (1) is carried out by methods generally known in the art, such as enterally, parenterally, dermally or nasally, in the form of suitable preparations. Administration can be carried out prophylactically, methaphylactically or therapeutically. Administration may be performed systemically.

Thus, according to one embodiment of the present invention, a compound represented by Formula (1) for use as a medicament is provided. According to another embodiment, a compound represented by Formula (1) for use as an anti-endoparasitical agent is provided. According to another embodiment, a compound represented by Formula (1) for use as a anthelmintic agent, more particularly for use as a nematicidal agent, a platyhelminthicidal agent, an acanthocephalicidal agent, or a pentastomicidal agent, is provided. According to another embodiment, a compound represented by Formula (1) for use as an antiprotozoal agent is provided. According to another embodiment, a compound represented by Formula (1) for use as an anti-ectoparasitical agent, particularly an arthropodicidal agent, more particularly an insecticidal agent or acaricidal agent, is provided.

According to a further embodiment, a veterinary formulation is provided which includes an effective amount of at least one compound represented by Formula (1) and at least one of a pharmaceutically acceptable excipient (e.g. a solid or liquid diluent), a pharmaceutically acceptable auxiliary (e.g. a surfactant). In particular, a veterinary formulation including an effective amount of at least one compound represented by Formula (1) and a pharmaceutically acceptable excipient and/or pharmaceutically acceptable auxiliary which is normally used in veterinary formulations is provided.

According to another embodiment, a method for preparing a veterinary formulation as described herein is provided, the method including a step of mixing at least one compound represented by Formula (1) with at least one of a pharmaceutically acceptable excipient or a pharmaceutically acceptable auxiliary. The at least one of a pharmaceutically acceptable excipient or a pharmaceutically acceptable auxiliary may be selected from those normally used in veterinary formulations.

According to another embodiment, a veterinary formulation including a compound represented by Formula (1), which works as at least one of an ectoparasiticidal formulation or an endoparasiticidal formulation, is provided. The veterinary formulation may work as at least one selected from the group of anthelmintic, antiprotozoal, and arthropodicidal formulations, and more specifically at least one selected from the group of nematicidal, platyhelminthicidal, acanthocephalicidal, pentastomicidal, insecticidal, and acaricidal formulations, depending on embodiments as well as their methods for preparation.

According to another embodiment, a method for treatment of a parasitic infection, in particular an infection by a parasite selected from the group of ectoparasites and endoparasites, is provided which includes applying an effective amount of a compound represented by Formula (1) to an animal, in particular a non-human animal, in need thereof.

According to another embodiment, a method for treatment of a parasitic infection, in particular an infection by a parasite selected from the group of ectoparasites and endoparasites, is provided which includes applying the veterinary formulation as defined herein to an animal, in particular a non-human animal, in need thereof.

According to another embodiment, use of a compound represented by Formula (1) in the treatment of a parasitic infection, in particular an infection by a parasite selected from the group of ectoparasites and endoparasites, in an animal, in particular a non-human animal is provided.

In the present context of the animal health or veterinary field, the scope of the term "treatment" encompasses prophylactic treatment, metaphylactic treatment as well as therapeutical treatment.

In another embodiment, the present invention provides a pharmaceutical combination ("combination" sometimes also referred to as "mixture"), in particular a veterinary combination, which comprises:

one or more compounds represented by Formula (1) as defined supra, and one or more further active ingredients, in particular one or more endo- and/or ectoparasiticides.

The term "combination" in the present invention is used as known to persons skilled in the art, it being possible for said combination to be a fixed combination, a non-fixed combination or a kit-of-parts.

A "fixed combination" in the present invention is used as known to persons skilled in the art. The fixed composition is, for example, a combination wherein one or more compounds represented by Formula (1) of the present invention, and one or more further active ingredients are present together in one unit dosage or in one single entity. One example of a "fixed combination" is a pharmaceutical composition wherein a compound represented by Formula (1) and a further active ingredient are present in admixture for simultaneous administration, such as in a formulation. Another example of a "fixed combination" is a pharmaceutical combination wherein a compound represented by Formula (1) and a further active ingredient are present in one unit without being in admixture.

A non-fixed combination or "kit-of-parts" in the present invention is used as known to persons skilled in the art. The non-fixed combination is, for example, a combination wherein one or more compounds represented by Formula (1) and one or more further active ingredients are present in more than one unit. One example of a non-fixed combination or kit-of-parts is a combination wherein a compound represented by Formula (1) and a further active ingredient are present separately. The components of the non-fixed combination or kit-of-parts may be administered separately, sequentially, simultaneously, concurrently or chronologically staggered.

The compound represented by Formula (1) may be administered as the sole pharmaceutical agent or in combination with one or more other pharmaceutically active ingredients where the combination causes no unacceptable adverse effects. The present invention also covers such pharmaceutical combinations. For example, the compound represented by Formula (1) may be combined with known ectoparasiticides and/or endoparasiticides.

The other or further active ingredients specified herein by their common names are known and described, for example, in the Pesticide Manual ("The Pesticide Manual" 16th Ed., British Crop Protection Council 2012) or can be searched in the internet (e.g. http://www.alanwood.net/pesticides); also Mehlhorn et al Encyclopaedic Reference of Parasitology 4th edition (ISBN 978-3-662-43978-4) may be mentioned. The classification is based on the current IRAC Mode of Action Classification Scheme at the time of filing of this patent application.

Examples of insecticides, acaricides and nematicides, including ectoparasiticides and/or endoparasiticides, that may be used in the present invention include the following chemicals, without limitation:

(1) Acetylcholinesterase (AChE) inhibitors, such as carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as cyclodiene-organochlorines, for example chlordane and endosulfan or phenylpyrazoles (fiproles), for example ethiprole and fipronil.

(3) Sodium channel modulators, such as pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as spinosyns, e.g. spinetoram and spinosad.

(6) Glutamate-gated chloride channel (GluCl) allosteric modulators, such as avermectins/milbemycins, for example abamectin, emamectin benzoate, lepimectin and milbemectin.

(7) Juvenile hormone mimics, such as juvenile hormone analogues, e.g. hydroprene, kinoprene and methoprene or fenoxycarb or pyriproxyfen.

(9) Modulators of Chordotonal Organs, such as, for example pymetrozine or flonicamid.

(10) Mite growth inhibitors, such as, for example clofentezine, hexythiazox and diflovidazin or etoxazole.

(12) Inhibitors of mitochondrial ATP synthase, such as, ATP disruptors such as diafenthiuron or organotin compounds, for example azocyclotin, cyhexatin and fenbutatin oxide or propargite or tetradifon.

(13) Uncouplers of oxidative phosphorylation via disruption of the proton gradient, such as chlorfenapyr, DNOC and sulfluramid.

(14) Nicotinic acetylcholine receptor channel blockers, such as bensultap, cartap hydrochloride, thiocylam, and thiosultap-sodium.

(15) Inhibitors of chitin biosynthesis, type 0, such as bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as cyromazine.

(18) Ecdysone receptor agonists, such as chromafenozide, halofenozide, methoxyfenozide and tebufenozide.

(19) Octopamine receptor agonists, such as amitraz.

(20) Mitochondrial complex III electron transport inhibitors, such as hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as tetronic and tetramic acid derivatives, e.g. spirodiclofen, spiromesifen and spirotetramat.

(25) Mitochondrial complex II electron transport inhibitors, such as beta-ketonitrile derivatives, e.g. cyenopyrafen and cyflumetofen and carboxanilides, such as pyflubumide.

(28) Ryanodine receptor modulators, such as diamides, e.g. chlorantraniliprole, cyantraniliprole and flubendiamide.

Further examples include: further active ingredients such as Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tioxazafen, Thiofluoximate, Triflumezopyrim and iodomethane; furthermore preparations based on Bacillus firmus (I-1582, BioNeem, Votivo), and also the following compounds: 1-{2-fluoro-4-methyl-5-[(2,2,2-trifluoroethyl) sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro [indol-3,4'-piperidin]-1(2H)-yl}(2-chloropyridin-4-yl) methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)-N-[3-chloro-1-(3-pyridinyl)-1H-pyrazol-4-yl]-N-ethyl-3-[(3,3,3-trifluoropropyl)sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-azabicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8) and N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9).

Further Examples Include:

active ingredients with unknown or non-specific mode of action, e.g., fentrifanil, fenoxacrim, cycloprene, chlorobenzilate, chlordimeform, flubenzimine, dicyclanil, amidoflumet, quinomethionate, triarathene, clothiazoben, tetrasul, potassium oleate, petroleum, metoxadiazone, gossyplure, flutenzin, bromopropylate, cryolite;

active ingredients from other classes, e.g. butacarb, dimetilan, cloethocarb, phosphocarb, pirimiphos (-ethyl), parathion (-ethyl), methacrifos, isopropyl o-salicylate, trichlorfon, sulprofos, propaphos, sebufos, pyridathion, prothoate, dichlofenthion, demeton-S-methylsulphone, isazofos, cyanofenphos, dialifos, carbophenothion, autathiofos, aromfenvinfos (-methyl), azinphos (-ethyl), chlorpyrifos (-ethyl), fosmethilan, iodofenphos, dioxabenzofos, formothion, fonofos, flupyrazofos, fensulfothion, etrimfos;

organochlorines, e.g. camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-), metofluthrin, profluthrin, flufenprox, flubrocythrinate, fubfenprox, fenfluthrin, protrifenbute, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated carbonhydrogen compounds (HCHs);

neonicotinoids, e.g. nithiazine;

dicloromezotiaz, triflumezopyrim; and macrocyclic lactones, e.g. nemadectin, ivermectin, latidectin, moxidectin, selamectin, eprinomectin, doramectin, emamectin benzoate; milbemycin oxime;

triprene, epofenonane, diofenolan.

Further Examples Include:

biologicals, hormones or pheromones, for example natural products, e.g. thuringiensin, codlemone or neem components;

dinitrophenols, e.g. dinocap, dinobuton, binapacryl;

benzoylureas, e.g. fluazuron, penfluron;

amidine derivatives, e.g. chlormebuform, cymiazole, demiditraz; and bee hive varroa acaricides, for example organic acids, e.g. formic acid, oxalic acid.

Preferred insecticides and acaricides for use in animal health include, without limitation:

effectors at arthropod ligand gated chloride channels, such as chlordane, heptachlor, endoculfan, Dieldrin, bromocyclen, toxaphene, lindane, fipronil, pyriprole, sisapronil, afoxolaner, fluralaner, sarolaner, lotilaner, fluxametamide, broflanilide, avermectin, doramectin, eprinomectin, ivermectin, milbemycin, moxidectin, and selamectin;

modulators of arthropod octopaminergic receptors, such as amitraz, BTS27271, cymiazole, and demiditraz;

effectors at arthropod voltage-gated sodium channels, such as DDT, methoxychlor, metaflumizone, indoxacarb, cinerin I, cinerin II, jasmolin I, jasmolin II, pyrethrin I, pyrethrin II, allethrin, alphacypermethrin, bioallethrin, betacyfluthrin, cyfluthrin, cyhalothrin, cypermethrin, deltamethrin, etofenprox, fenvalerate, flucythrinate, flumethrin, halfenprox, permethrin, phenothrin, resmethrin, tau-fluvalinate, and tetramethrin;

effectors at arthropod nicotinic cholinergic synapses (acetylcholine esterase, acetylcholine receptors), such as bromoprypylate, bendiocarb, carbaryl, methomyl, promacyl, propoxur, azamethiphos, chlorfenvinphos, chlorpyrifos, coumaphos, cythioate, diazinon, diclorvos, dicrotophos, dimethoate, ethion, famphur, fenitrothion, fenthion, heptenophos, malathion, naled, phosmet, phoxim, phtalofos, propetamphos, temephos, tetrachlorvinphos, trichlorfon, imidacloprid, nitenpyram, dinotefuran, spinosad, and spinetoram; and effectors on arthropod development processes, such as cyromazine, dicyclanil, diflubenzuron, fluazuron, lufenuron, triflumuron, fenoxycarb, hydroprene, methoprene, pyriproxyfen, fenoxycarb, hydroprene, S-methoprene, and pyriproxyfen.

Exemplary active ingredients from the group of endoparasiticides, as mixing partners, include, without limitation, anthelmintically active compounds and antiprotozoal active compounds.

Anthelmintically active compounds, include, without limitation, the following nematicidally, trematicidally and/or cestocidally active compounds:

from the class of macrocyclic lactones, for example, eprinomectin, abamectin, nemadectin, moxidectin, doramectin, selamectin, lepimectin, latidectin, milbemectin, ivermectin, emamectin, and milbemycin;

from the class of benzimidazoles and probenzimidazoles, for example, oxibendazole, mebendazole, triclabendazole, thiophanate, parbendazole, oxfendazole, netobimin, fenbendazole, febantel, thiabendazole, cyclobendazole, cambendazole, albendazole-sulphoxide, albendazole, and flubendazole;

from the class of depsipeptides, preferably cyclic depsipetides, in particular 24-membered cyclic depsipeptides, for example, emodepside, and PF1022A;

from the class of tetrahydropyrimidines, for example, morantel, pyrantel, and oxantel;

from the class of imidazothiazoles, for example, butamisole, levamisole, and tetramisole;

from the class of aminophenylamidines, for example, amidantel, deacylated amidantel (dAMD), and tribendimidine;

from the class of aminoacetonitriles, for example, monepantel;

from the class of paraherquamides, for example, paraherquamide and derquantel;

from the class of salicylanilides, for example, tribromsalan, bromoxanide, brotianide, clioxanide, closantel, niclosamide, oxyclozanide, and rafoxanide;

from the class of substituted phenols, for example, nitroxynil, bithionol, disophenol, hexachlorophene, niclofolan, and meniclopholan;

from the class of organophosphates, for example, trichlorfon, naphthalofos, dichlorvos/DDVP, crufomate, coumaphos, and haloxon;

from the class of piperazinones/quinolines, for example, praziquantel and epsiprantel;

from the class of piperazines, for example, piperazine and hydroxyzine;

from the class of tetracyclines, for example, tetracyclin, chlorotetracycline, doxycyclin, oxytetracyclin, and rolitetracyclin; and from diverse other classes, for example, bunamidine, niridazole, resorantel, omphalotin, oltipraz, nitroscanate, nitroxynile, oxamniquine, mirasan, miracil, lucanthone, hycanthone, hetolin, emetine, diethylcarbamazine, dichlorophen, diamfenetide, clonazepam, bephenium, amoscanate, and clorsulon.

Antiprotozoal active compounds, include, without limitation, the following active compounds:

from the class of triazines, for example, diclazuril, ponazuril, letrazuril, and toltrazuril;

from the class of polyether ionophore, for example, monensin, salinomycin, maduramicin, and narasin;

from the class of macrocyclic lactones, for example, milbemycin and erythromycin; from the class of quinolones, for example, enrofloxacin and pradofloxacin; from the class of quinines, for example, chloroquine;

from the class of pyrimidines, for example, pyrimethamine;

from the class of sulfonamides, for example, sulfaquinoxaline, trimethoprim, and sulfaclozin;

from the class of thiamines, for example, amprolium;

from the class of lincosamides, for example, clindamycin;

from the class of carbanilides, for example, imidocarb;

from the class of nitrofuranes, for example, nifurtimox;

from the class of quinazolinone alkaloids, for example, halofuginon;

from diverse other classes, for example, oxamniquin, paromomycin;

from the class of vaccines or antigenes from microorganisms, for example, *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis*, and *Dictyocaulus viviparus*. Each named mixing partner may form a salt with a suitable base or acid if its functional group enable the formation of the salt.

The compound represented by Formula (1) may also be used in vector control. For the purpose of the present invention, a vector is an arthropod, in particular an insect or arachnid, capable of transmitting pathogens such as viruses, worms, single-cell organisms and bacteria from a reservoir (plant, animal, human, etc.) to a host. The pathogens can be transmitted either mechanically (for example trachoma by non-stinging flies) to a host, or by injection (for example malaria parasites by mosquitoes) into a host.

Examples of vectors and the diseases or pathogens they transmit are:
1) Mosquitoes
   *Anopheles*: malaria, filariasis;
   *Culex*: Japanese encephalitis, other viral diseases, filariasis, transmission of other worms;
   *Aedes*: yellow fever, dengue fever, other viral diseases, filariasis;
   Simuliidae: transmission of worms, in particular *Onchocerca volvulus;*
   Psychodidae: transmission of leishmaniasis
2) Lice: skin infections, epidemic typhus;
3) Fleas: plague, endemic typhus, cestodes;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia burgdorferi* sensu lato., *Borrelia duttoni*, tick-borne encephalitis, Q fever (*Coxiella burnetii*), babesioses (*Babesia canis canis*), ehrlichiosis.

Further examples of vectors in the sense of the present invention are insects and arachnids such as mosquitoes, in particular of the genera *Aedes, Anopheles*, for example *A. gambiae, A. arabiensis, A. funestus, A. dirus* (malaria) and *Culex*, psychodids such as *Phlebotomus, Lutzomyia*, lice, fleas, flies, mites and ticks capable of transmitting pathogens to animals and/or humans.

Vector control is also possible if the compound represented by Formula (1) is resistance-breaking. The compound represented by Formula (1) is suitable for use in the prevention of diseases and/or pathogens transmitted by vectors. Thus, a further aspect of the present invention is the use of a compound represented by Formula (1) for vector control in the field of animal health. Yet a further aspect of the present invention is the use of a compound represented by Formula (1) for vector control in the field of human health.

The compound represented by Formula (1) as an active ingredient can be used for controlling various pests which give damage to paddy rices, fruit trees, vegetables, other crops and flowers and ornamental plants in agricultural, horticultural or stored grain products, or sanitary pests. Examples of organisms that can be controlled by the compound represented by Formula (1) also include vermin such as eelworm. Further, the compound represented by Formula (1) has a strong insecticidal effect against Lepidoptera such as cotton caterpillar (*Diaphania indica*), oriental tea tortrix (*Homona magnanima*), cabbage webworm (*Hellulla undalis*), summer fruit tortrix (*Adoxophyes orana fasciata*), smaller tea tortrix (*Adoxophyes honmai*), apple tortrix (*Archips fuscocupreanus*), peach fruit moth (*Carposina niponensis*), Manchurian fruit moth (*Grapholita inopinata*), oriental fruit moth (*Grapholita molesta*), soybean pod borer (*Leguminivora glycinivorella*), mulberry leafroller (*Olethreutes mori*), citrus leafminer (*Phyllocnistis citrella*), tomato leafminer (*Tuta absoluta*), persimmon fruit moth (*Stathmopoda masinissa*), tea leafroller (*Caloptilia theivora, Caloptilia zachrysa*), apple-leafminer (*Phyllonorycter ringoniella*), pear barkminer (*Spulerrina astaurota*), small citrus dog (*Papilio xuthus*), common cabbage worm (*Pieris rapae crucivora*), tobacco budworm (*Heliothis virescens*), cotton bollworm (*Helicoverpa armigera*), codling moth (*Cydia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tobacco moth (*Ephestia elutella*), mulberry pyralid (*Glyphodes pyloalis*), paddy borer (*Scirpophaga incertulas*), rice skipper (*Parnara guttata*), rice armyworm (*Pseudaletia separata*), pink borer (*Sesamia inferens*), cabbage armyworm (*Mamestra brassicae*), common cutworm (*Spodoptera litura*), beet armyworm (*Spodoptera exigua*), black cutworm (*Agrotis ipsilon*), turnip moth (*Agrotis segetum*), beet semi-looper (*Autographa nigrisigna*), cabbage looper (*Trichoplusia ni*); Hemiptera such as aster leafhopper (*Macrosteles fascifrons*), green rice leafhopper (*Nephotettix cincticeps*), grape leafhopper (*Arboridia apicalis*), tea green leafhopper (*Empoasca onukii*), brown rice planthopper (*Nilaparvata lugens*), small brown planthopper (*Laodelphax striatellus*), whitebacked rice planthopper (*Sogatella furcifera*), citrus psylla (*Diaphorina citri*), grape whitefly (*Aleurolobus taonabae*), silverleaf whitefly (*Bermisia argentifolii*), sweetpotato whitefly (*Bemisia tabaci*), greenhouse whitefly (*Trialeurodes vaporariorum*), turnip aphid (*Lipaphis erysimi*), cotton aphid (*Aphis gossypii*), apple aphid (*Aphis Citricola*), green peach aphid (*Myzus persicae*), Indian wax scale (*Ceroplastes ceriferus*), Comstock mealybug (*Pseudococcus Comstocki*), Japanease mealybug (*Planococcus kraunhiae*), cottony citrus scale (*Pulvinaria aurantii*), camphor scale (*Pseudaonidia duplex*), san Jose scale (*Comstockaspis perniciosa*), arrowhead scale (*Unaspis yanonensis*), brownwinged green bug (*Plautia Stali*), brown marmorated stink bug (*Halyomorpha mista*), sorghum plant bug (*Stenotus rubrovittatus*), rice leaf bug (*Trigonotylus caelestialium*); Coleoptera such as soybean beetle (*Anomala rufocuprea*), Japanese beetle (*Popillia japonica*), cigarette beetle (*Lasioderma serricorne*), powderpost beetle (*Lyctusbrunneus*), twenty-eight-spotted ladybird (*Epilachna vigintioctopunctata*), adzuki bean weevil (*Callosobruchus chinensis*), vegetable weevil (*Listroderes costirostris*), maize weevil (*Sitophilus zeamais*), boll weevil (*Anthonomus grandis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica* sp.), wireworm (*Agriotes* sp.), yellowspotted longicorn beetle (*Psacothea hilaris*), whitespotted longicorn beetle (*Anoplophora malasiaca*); Diptera such as melon fly (*Dacus(Bactrocera) dorsalis*), rice leafminer (*Agromyza oryzae*), onion maggot (*Delia antiqua*), seedcorn maggot (*Delia platura*), soybean pod gall midge (*Asphondylia* sp.), house fly (*Musca domestica*), garden pea leafminer (*Chromatomyia horticola*), legume leafminer (*Liriomyza trifolii*), bryony leafminer (*Liriomyza bryoniae*), Mosquitos (e.g. *Anopheles gambiae, Anopheles arabiensis, Anopheles funestus, Anophelesmelas, Anopheles minimus, Anopheles dirus, Anopheles stephensi, Anopheles sinensis, Anopheles albimanus, Culex pipiens molestus, Culex pipiens pipiens, Culex pipiens pallens, Culex quinquefasciatus, Culex restuans, Culex tarsalis, Culex modestus, Culex tritaeniorhynchus, Aedes aegypti, Aedes albopictus, Aedes japonicas, Aedes vexans*); Hymenoptera such as cabbage sawfly (*Athalia japonica*), turnip sawfly (*Athalia rosae ruficornis*), apple argid sawfly (*Arge mali*), large rose sawfly (*Arge pagana*), oriental chestnut gall wasp (*Dryocosmus kuriphilus*), wood ant (*Formica japonica*); Acarina such as broad mite (*Polyphagotarsonemus latus*), cyclamen mite (*Steneotarsonemus pallidus*), fungus mite (*Tarsonemus waitei*), straw itch mite (*Pyemotes ventricosus*), blue oat mite (*Penthaleus major*), citrus flat mite (*Brevipalpus lewisi*), privet mite (*Brevipalpus obovatus*), pineapple flat mite (*Dolichotetranychus floridanus*), persimmon false spider mite (*Tenuipalpus zhizhilashviliae*), flat mite (*Brevipalpus phoenicis*), Tuckerellid mite (*Tuckerella pavoniformis*), clover mite (*Bryobia praetiosa*), apricot spider mite (*Eotetranychus boreus*), sugi spider mite (*Oligonychus hondoensis*), citrus red mite (*Panonychus citri*), European red mite (*Panonychus ulmi*), carmine spider mite (*Tetranychus cinnabarinus*), tea red spider mite (*Tetranychus kanzawai*), two-spotted spider mite (*Tetranychus urticae*), hawthorn spider mite (*Tetranychus viennensis*), pink tea rust mite (*Acaphylla theae*), tulip bulb mite (*Aceria tulipae*), pink citrus rust mite (*Aculops pelekassi*), apple rust mite (*Aculus schlechtendali*), ribbed tea mite (*Calacarus carinatus*), grape leaf rust mite (*Calepitrimerus vitis*), pear rust mite (*Epitrimerus pyri*), Japanese pear rust mite (*Eriophyes chibaensis*), flour mite (*Acarus siro*), brown legged grain mite (*Aleuroglyphus ovatus*), bulb mite (*Rhizoglyphus robini*), mould mite (*Tyrophagus putrescentiae*), tropical rat mite (*Ornithonyssus bacoti*), scrub typhus mite (*Leptotrombidium akamushi*), mite (*Leptotrombidium scutellaris*), chigger mite (*Leptotrombidium pallidum*); Nematoda such as coffee root-lesion nematode (*Pratylenchus coffeae*), root-lesion nematode (*Pratylenchus* sp.), potato cyst nematode (*Globodera rostochiensis*), white potato cyst nematode (*Globodera pallida*), cyst nematodes (*Heterodera* sp.), root-knot nematode (*Meloidogyne* sp.), citrus nematode (*Tylemchulus semipenetrans*), Aphelenchus avenae chrysanthemum foliar nematode (*Aphelenchoides ritzemabosi*), rice white-tip nematode (*Aphelenchoides besseyi*); Thysanoptera such as melon thrips (*Thrips palmi*), western flower thrips (*Frankliniella oceidentalis*), yellow tea thrips (*Scirtothrips dorsalis*), honeysuckle thrips (*Thrips flavus*), onion thrips (*Thrips tabaci*); Isoptera such as drywood termite (*Cryptotermes domesticus*), Formosan subterranean termite (*Coptotermes formosanus*), Japanese subterranean termite (*Reticulitermes speratus*), fungus-growing termite (*Odontotermes formosanus*); Orthoptera such as German cockroach (*Blattella germanica*), American cockroach (*Periplaneta americana*), rice grasshopper (*Oxya yezoensis*) and the like.

The compound represented by Formula (1) as an active ingredient have notable insecticidal effect against the above-described pests that damage various lowland crops, upland crops, fruit trees, vegetables, other crops and horticultural products. Thus, the insecticidal effect of the invention can be obtained by treating the paddy field water, plant stems and leaves, or soil of the crops of lowland, upland, fruit trees, vegetables, other crops, and flowers and ornamental plants, during the seasons expected of the appearance of such pests, or before or at the point of pest appearance.

According to an embodiment, a horticultural or agricultural insecticide containing the compound represented by Formula (1) as an active ingredient is provided. According to another embodiment, a method of protecting a crop from a harmful organism is provided, the method including treating a crop or a soil for the crop with an effective amount of the compound represented by Formula (1).

According to an embodiment, a composition including the compound represented by Formula (1) mixed with an inert carrier, and optionally with an auxiliary agent is provided. According to another embodiment, a mixture including the compound represented by Formula (1) combined with at least one other insecticide and/or fungicide is provided.

The compound represented by Formula (1) is in general used in appropriate formulation forms according to the use, prepared by conventional methods for preparation of agricultural and horticultural chemicals. That is, the compound represented by Formula (1) may be used in suitable formulations, such as a suspension, an emulsion, a liquid formulation, a water-dispersible powder, a granule, a dust formulation, a tablet or the like, prepared by blending the compound with at least one of a suitable inert carrier or an auxiliary agent, if necessary, in an appropriate proportion, followed by dissolution, separation, suspension, mixing, impregnation, adsorption or adhesion of the ingredients.

The inert carrier that can be used in the invention may be a solid or a liquid, and examples thereof include, in particular, soybean powders, grain powders, wood powders, bark powders, coarse powders, tobacco powders, walnut shell powders, brans, cellulose powders, residues from plant extraction, synthetic polymers such as pulverized synthetic resins, clays (for example, kaolin, bentonite, acidic white clay), talc (for examples, talc, pyrophyllite, etc.), silica (for examples, diatomite, sand, mica, white carbon (hydrous silica powders, hydrous silica powders called synthetic high dispersity silicic acids, there are also products containing calcium silicate as main component)), activated carbon, sulfur powder, pumice, calcined diatomaceous powders, pulverized bricks, fly ash, sand, inorganic mineral powders such as calcium carbonate and calcium phosphate, chemical fertilizers such as ammonium sulfate, ammonium phosphate, ammonium nitrate, urea and ammonium chloride, and a compost, which are used singly or in mixture of two or more thereof.

Examples of materials that can be used as an inert carrier in the form of a liquid include those having the function as solvent, as well as those not having the function as solvent but still capable of dispersing the active ingredient compound under an aid of an auxiliary agent. Examples of the inert carrier include: water, alcohols (e.g., methanol, ethanol, isopropanol, butanol, ethylene glycol, etc.), ketones (e.g., acetone, methyl ethyl ketone, methyl isobutyl ketone, diisobutylketone, cyclohexanone, etc.), ethers (e.g., diethyl ether, dioxane, cellosolve, diisopropyl ether, tetrahydrofuran, etc.), aliphatic hydrocarbons (e.g., kerosene, mineral oil, etc.), aromatic hydrocarbons (e.g., benzene, toluene, xylene, solvent naphtha, alkyl naphthalene, etc.), halogenated hydrocarbons (e.g., dichloromethane, chloroform, tetrachlorocarbon, chlorobenzene, etc.), esters (e.g., ethyl acetate, butyl acetate, ethyl propionate, diisobutyl phthalate, dibutyl phthalate, dioctyl phthalate, etc.), amides (e.g., dimethyl formamide, diethyl formamide, dimethyl acetamide, etc.), and nitriles (e.g., acetonitrile, etc.), which are used singly or in mixture of two or more thereof.

Examples of the auxiliary agent include the following auxiliary agents, which are used singly or in combination of two or more of them depending on the purpose; however, it is also possible not to use any auxiliary agent.

For the purpose of emulsification, dispersion, solubilization and/or wetting of the active ingredient compound, surfactants may be used. Examples of surfactants include polyoxyethylene alkyl ethers, polyoxyethylene alkyl aryl ethers, polyoxyethylene higher fatty acid esters, polyoxyethylene resin acid esters, polyoxyethylene sorbitan monolaurate, polyoxyethylene sorbitan monooleates, alkyl aryl sulfonate, naphthalene sulfonate, lignin sulfonate, and higher alcohol sulfonate esters.

Examples of auxiliary agents that may be used for the purpose of dispersion stabilization, adhesion and/or binding of the active ingredient compound include casein, gelatin, starch, methyl cellulose, carboxymethyl cellulose, gum Arabic, polyvinyl alcohol, pine root oil, corn oil, bentonite, xanthan gum, and lignin sulfonate salts.

Examples of auxiliary agents that may be used for the purpose of improving the flowability of solid products include wax, stearic acid salts, and phosphoric alkyl esters. An auxiliary agent such as a naphthalene sulfonate condensation product or a condensed phosphate salt may be used as a suspending agent in suspensions. An antifoaming agent such as silicone oils can be also used as an auxiliary agent.

In addition, the compound represented by Formula (1) is stable against light, heat, oxidation and the like, but if desired, more stable compositions may be obtained by adding a stabilizer. Examples of the stabilizer include antioxidants, UV absorbents, phenol derivatives such as BHT (2, 6-di-t-butyl-4-methyl phenol), BHA (butylhydroxy anisole), bisphenol derivatives, and aryl amines such as phenyl-α-naphthyl amine, phenyl-β-naphthyl amine, condensation product of phenetidine and acetone, and benzophenone compounds.

The effective amount of the compound represented by Formula (1) is typically 0.5 to 20% by weight in a dust formulation, 5 to 50% by weight in an emulsion, 10 to 90% by weight in a water-dispersible powder, 0.1 to 20% by weight in a granule, and 10 to 90% by weight in a flowable formulation. Meanwhile, the amount of carrier in the respective formulations is typically 60 to 99% by weight in a dust formulation, 40 to 95% by weight in an emulsion, 10 to 90% by weight in a water-dispersible powder, 80 to 99% by weight in a granule, and 10 to 90% by weight in a flowable formulation. The amount of auxiliary agent, such as those described above, is typically 0.1 to 20% by weight in a dust formulation, 1 to 20% by weight in an emulsion, 0.1 to 20% by weight in a water-dispersible powder, 0.1 to 20% by weight in a granule, and 0.1 to 20% by weight in a flowable formulation.

In order to control various pests, an amount of the compound represented by Formula (1) as an active ingredient that is effective for blight control may be applied, just as it is, or as an adequate dilution with water, or as a suspension, to the crops expected of the appearance of the corresponding pests or to the places where such occurrence is not preferable. The amount of use depends on various factors such as the purpose, the pest to be controlled, the state of plant growth, trend of pest appearance, climate, environmental conditions, formulation, method of use, place of use, timing of use and the like. It is preferable to use the compound represented by Formula (1) as an active ingredient in the concentration of 0.0001 to 5000 ppm, and preferably 0.01 to 1000 ppm. The dose of the compound represented by Formula (1) that can be used in approximately 10 a (acre) is generally in the range of 1 to 300 g of the active ingredient.

The compound represented by Formula (1) as an active ingredient may be used alone in control of various pests in agricultural, horticultural and stored grain products, which damage the rice plants, fruit trees, vegetables, other crops and flowers, or sanitary pests or eelworms. Further, in order to obtain superior control effect with respect to various pests which occur at the same time, the compound represented by Formula (1) may be used in combination with at least one other insecticide and/or fungicide.

With regard to the mixed formulation (mixture) of the invention for controlling a pest, examples of an insecticide, a miticide or a nematicide as a compound which can be combined with the compound represented by Formula (1) include a compound selected from a pyrethroidbased compound, an organo phosphorus-based compound, an oxime-carbamate-based compound, a carbamate-based compound, a neonicotinoid-based compound, a diacylhydrazinebased compound, a benzoyl urea-based compound, a juvenile hormone-based compound, a cyclodiene organic chlorine-based compound, a 2-dimethylaminopropane-1,3-dithiol-based compound, an amidine-based compound, a phenylpyrazole-based compound, an organo tin-based compound, a METI-based compound, a benzylate-based compound, an allylpyrrol-based compound, a dinitrophenol-based compound, an anthranyl-diamide-based compound, an oxadiazine-based compound, a semicarbazone-based compound, a tetronic acid-based compound, a carbamoyl-triazolebased compound, or a tetrazine-based compound. Examples of a fungicide which can be combined with the compound represented by Formula (1) include a strovilurin-based compound, an anilinopyrimidine-based compound, an azole-based compound, an azole-based compound, a dithiocarbamate-based compound, a phenylcarbamate-based compound, an organic chlorine-based compound, a benzimidazole-based compound, a phenylamide-based compound, a sulfenic acid-based compound, a copper-based compound, an isoxazole-based compound, an organo phosphorus-based compound, a N-halogenothioalkyl-based compound, a carboxyanilide-based compound, a morpholine-based compound, an organo tin-based compound, and a cyanopyrrol-based compound. A fumigating agent such as chloropicrin or a natural product compound, for example, nicotine may also be used in combination with the compound represented by Formula (1).

Examples of compounds that may be used in combination with the compound represented by Formula (1) further include compounds other than the above groups. Specific examples include the following compounds:

pyrethroid-based compounds and various isomers thereof, such as acrinathrin, allethrin [(1R)-isomer], bifenthrin, bioallethrin, bioallethrin S-cyclopentenyl isomer, bioresmethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, thetacypermethrin, zeta-cypermethrin, cyphenothrin [(1R)-trans isomer], deltamethrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, methothrin, metofluthrin, permethrin, phenothrin [(1R)-trans-isomer], prallethrin, resmethrin, RU15525 (kadethrin), silafluofen, tefluthrin, tetramethrin, tetramethrin [(1R)-isomer], tralomethrin, transfluthrin, ZXI8901, biopermethrin, furamethrin, profluthrin, flubrocythrinate, and dimefluthrin;

organo phosphorus-based compounds, such as acephate, azamethiphos, azinphos-methyl, azinphos-ethyl, cadusafos, chlorethoxyfos, chlorfenvinphos, chlormephos, chlorpyrifos, chlorpyrifos-methyl, coumaphos, CYAP (cyanophos), demeton-S-methyl, diazinon, ECP (dichlofenthion), DDVP (dichlorvos), dicrotophos, dimethoate, dimethylvinphos, disulfoton (ethylthiometon), EPN (0-ethyl 0-4-nitrophenyl phenylphosphonothioate), ethion, ethoprophos, Famphur, fenamiphos, MEP (fenitrothion), MPP (fenthion), fosthiazate, heptenophos, isofenphos-methyl, Isocarbophos (isopropyl O-methoxyaminothio=phosposphoryl) salicylate), isoxathion, malathion, mecarbam, methamidophos, DMTP (methidathion), mevinphos, monocrotophos, BRP (paled), onmethoate, oxydemeton-methyl, parathions, parathion-methyl, PAP (phenthoate), phorate, phosalone, phosmet, phosphamidon, phoxim, pirimiphos-methyl, profenofos, propetamphos, prothiofos, pyraclofos, pyridaphenthion, quinalphos, Sulfotep, tebupirimfos, temephos, terbufos, thiometon, triazophos, DEP (trichlorfon), vamidothion, Bayer 22/190 (chlorothion), bromfenvinfos, bromophos, bromophos-ethyl butathiofos, carbophenothion. Chlorphoxim, sulprofos, diamidafos, CVMP (tetrachlorvinphos), propaphos, mesulfenfos, dioxabenzofos (salithion), etrimfos, oxydeprofos, formothion, fensulfothion, isazofos, imicyafos (AKD3088), isamidofos, thionazin, and fosthietan;

oxime-carbamate-based compounds such as phosphocarb, alanycarb, butocarboxim, butoxycarboxim, thiodicarb, and Thiofanox;

carbamate-based compounds such as aldicarb, bendiocarb, benfuracarb, NAC (carbaryl), carbofuran, carbosulfan, ethiofencarb, BPMC (fenobucarb), Formetanate, furathiocarb, MIPC (isoprocarb), methiocarb, methomyl, oxamyl, pirimicarb, PHC (propoxur) trimethacarb, XMC (3,5-xylyl methylcarbamate), allyxycarb, aldoxycarb, bufencarb, butacarb, carbanolate, MTMC (metoloarb), MPMC (xylylcarb), fenothiocarb, xylylcarb, and bendiocarb;

neonicotinoid-based compounds such as acetamiprid, clothianidin, dinotefuran, imidacloprid, nitenpyram, thiacloprid, and thiamethoxam;

diacylhydrazine-based compounds such as chromafenozide, halofenozide, methoxyfenozide, and tebufenozide, benzoyl urea-based compounds such as bistrifluron, chlorfluazuron, diflubenzuron, flucycloxuron, flufenoxuron, hexaflumuron, lufenuron, novaluron, noviflumuron, teflubenzuron, and triflumuron;

juvenile hormone-based compounds such as fenoxycarb, hydroprene, kinoprene, methoprene, pyriproxyfen, methoprene, and hydroprene;

cyclodiene organic chlorine-based compounds such as chlordane, endosulfan, lindane (gamma-HCH), and dienochlor;

2-dimethylaminopropane-1,3-dithiol-based compounds such as Cartap hydrochloride and thiocyclam;

amidine-based compounds such as amitraz;

phenylpyrazole-based compounds such as ethiprole, fipronil, and acetoprole;

organo tin-based compounds such as azocyclotin, cyhexatin, and fenbutatin oxide;

mitochondrial electron transport inhibitor (METI)-based compounds such as fenazaquin, fenpyroximate, pyridaben, pylimidifen, tebufenpyrad, or tolfenpyrad;

benzylate-based compounds such as bromopropylate;

allylpyrrol-based compounds such as chlorfenapyl;

dinitrophenol-based compounds such as dinitro-ortho-cresol (DNOC) or binapacryl;

anthranyl-diamide-based compounds such as chlorantraniliprole and cyantraniliprole;

oxadiazine-based compounds such as indoxacarb;

semicarbazone-based compounds such as metaflumizone;

tetronic acid-based compounds such as spirodiclofen, spiromesifen, and spirotetramat;

carbamoyltriazole-based compounds such as triazamate;

tetrazine-based compounds such as diflovidazin;

insecticides, miticides and nematicides, such as abamectin, emamectin benzoate, milbemectin, lepimectin, acequinocyl, azadirachtin, bensultap, Benzoximate, bifenazate, buprofezin, CCA-50439, chinomethionat, clofentezine, cryolite, cyromazine, dazomet, dichlorodiisopropyl ether (DCIP), dichloro-diphenyl-trichloroethane (DDT), diafenthiuron, D-D (1,3-Dichloropropene), dicofol, dicyclanil, dinobuton, dinocap, ENT 8184, etoxazole, flonicamid, fluacrypyrim, flubendiamide, GY-81 (peroxocarbonate), hexythiazox, hydramethylnon, Hydrogen cyanide, methyl iodide, karanjin, MB-599 (verbutin), mercury chloride, metam, methoxychior, methyl isothiocyanate, pentachlorophenol, phosphine, piperonyl butoxide, polynactins, BPPS (propargite), pymetrozine, pyrethrins, pyridalyl, rotenone, S421 (bis(2,3,3,3-tetrachloropropyl)ether), sabadilla, spinosad, spinetoram, sulcofuron-sodium, sulfluramid, tetradifon, thiosultap, Tribufos, aldrin, amidithion, amidothioate, aminocarb, amiton, aramite, athidathion, azothoate, barium polysulphide, Bayer 22408, Bayer 32394, benclothiaz, 5-(1,3-benzodioxole-5-yl)-3-hexylcyclohexa-2-enone, 1,1-bis(4-chlorophenyl)-2-ethoxyethanol, butonate, butopyronoxyl, 2-(2-butoxyethoxy)ethyle thiocyanate, camphechlor, chlorbenside, chlordecone, chlordimeform, chlorfenethol, chlorfenson, isoprothiolane, fluazuron, metaldehyde, phenisobromolate, fluazinam, bialaphos, benomyl, levamisol, pyrifluquinazon, cyflumetofen, amidoflumet, IKA-2005, cyenopyrafen sulfoxaflor, pyrafluprole, pyriprole, tralopyril, flupyrazofos, diofenolan, chlorobenzilate, flufenzine, benzomate, flufenerim, Tripropyl isocyanurate (TPIC), albendazole, oxibendazole, fenbendazole, metam-sodium, 1,3-dichloropropene, flupyradifurone, afidopyropen, flometoquin, pyflubumide, fluensulfone, tetraniliprole, cyclaniliprole, fluxametamide, broflanilide, dicloromezotiaz, triflumezopyrim, fluazaindolizine, tioxazafen and fluhexafon;

strovilurin-based compounds such as azoxystrobin, kresoxym-methyl, trifloxystrobin, metominostrobin, and orysastrobin;

anilinopyrimidine-based compounds such as mepanipyrim, pyrimethanil, and cyprodinil;

azole-based compounds, such as triadimefon, bitertanol, triflumizole, metoconazole, propiconazole, penconazole, flusilazole, myclobutanil, cyproconazole, tebuconazole, hexaconazole, prochloraz, and simeconazole;

quinoxaline-based compounds such as quinomethionate;

dithiocarbamate-based compounds such as maneb, zineb, mancozeb, polycarbamate, and propineb;

phenylcarbamate-based compound such as diethofencarb;

organic chlorine-based compounds such as chlorothalonil and quintozene;

benzimidazole-based compounds, such as benomyl, thiophanate-methyl, and carbendazole;

phenylamide-based compounds, such as metalaxyl, oxadixyl, ofurase, benalaxyl, furalaxyl, and cyprofuram;

sulfenic acid-based compounds such as dichlofluanid;

copper-based compounds such as copper hydroxide and oxine-copper;

isoxazole-based compounds such as hydroxyisoxazole;

organo phosphorus-based compounds such as fosetyl-aluminium and tolclofos-methyl;

N-Halogenothioalkyl-based compounds such as captan, captafol, and folpet;

dicarboxyimide-based compounds such as procymidone, iprodione, and vinchlozolin;

carboxyanilide-based compounds, such as flutolanil, meproniL furamepyr, thifluzamide, boscalid, and penthiopyrad;

morpholine-based compounds such as fenpropimorph and dimethomorph;

organo tin-based compounds such as fenthin hydroxide and fenthin acetate;

cyanopyrrol-based compounds such as fludioxonil and fenpiclonil;

fungicides, such as tricyclazole, pyroquilon, carpropamid, diclocymet, fenoxanil, fthalide, fluazinam, cymoxanil, triforine, pyrifenox, fenarimol, fenpropidin, pencycuron, ferimzone, cyazofamid, iprovalicarb, benthiavalicarb-isopropyl, iminoctadin-albesilate, cyflufenamid, kasugamycin, validamycin, streptomycin, oxolinic-acid, tebufloquin, probenazole, tiadinil, isotianil, tolprocarb, or isofetamid, fenpicoxamid, quinofumelin, pydiflumetofen, dipymetitrone, and pyrazifumid;

fumigating agents, such as chloropicrin, ethylene dibromide (EDB), sulfuryl fluoride, acrylonitrile, bis(2-chloroethyl)ether, 1-bromo-2-chloroethane, 3-bromo-1-chloroprop-1-ene, bromocyclen, carbon disulfide, tetrachloromethane, metham sodium, nemadectin, and aluminium phosphide;

natural compounds, such as *Bacillus thuringiensis* delta-endotoxin, borax, calcium polysulfide, cryolite, cytokinin, nicotine, 2-(octylthio)ethanol, potassium oleate, sodium oleate, machine oil, sulfur, tar oil, anabasine, morantel tartrate, pyrethrum, nicotine sulfate, rape seed oil, soybean lecithin, starch, hydroxypropylstarch, decanoyloctanoylglycerol, propylene glycol fatty acid ester, diatomite, and *Bacillus thuringiensis*; and, furthermore;

a compound represented by the following Formula (A) and a salt thereof.

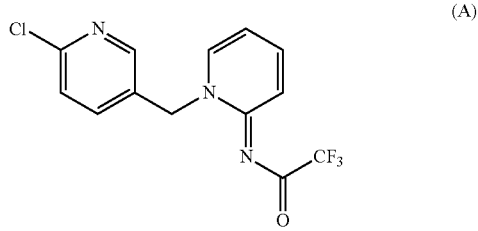 [SMILES: O=C(/N=c1\ccccn1Cc1ccc(Cl)nc1)C(F)(F)F]

(A)

When the compound represented by Formula (1) is used in combination with at least one other insecticide and/or fungicide, a mixed composition of the compound represented by Formula (1) and the other insecticide and/or fungicide may be used; alternatively, the compound represented by Formula (1) and the other insecticide/fungicide may be mixed and used at the time of applying.

With regard to a mixture of the compound represented by Formula (1) and another insecticide and/or fungicide, the mixing ratio of the compound represented by Formula (1) to the other insecticide and/or fungicide is, although not particularly limited, from 0.01:100 to 100:0.01, or from 0.1:100 to 100:0.1, or from 1:100 to 100:1, or from 1:10 to 10:1, or 1:1 (all in terms of weight) when expressed as the compound of the invention:other insecticide and/or fungicide. In addition, any range obtained by replacing the upper limit or the lower limit of any of the above ranges by the upperlimit or the lower limit of another range is also contemplated as a mixing ratio range in the present invention.

In addition to or in place of the above-mentioned insecticide or fungicide, the compound represented by Formula (1) may be mixed with a plant protecting agent, such as a herbicide, a fertilizer, a soil reformer, a plant growth controlling agent or any other material which are expected to provide an additive effect or a synergistic effect, in order to form a multi-purpose composition having high efficacy.

According to another embodiment, a compound represented by the following Formula (2) is provided:

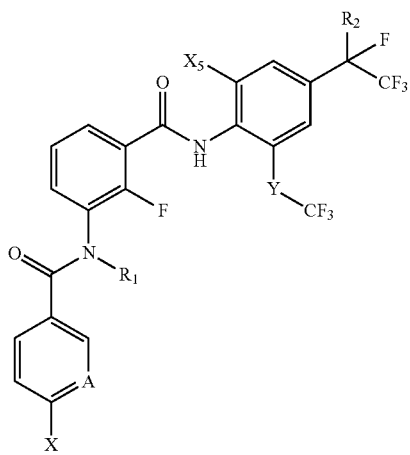

(2)

In Formula (2), $R_1$ represents a hydrogen atom or a $C_1$-$C_4$ alkyl group;

$R_2$ represents a trifluoromethyl group or a pentafluoroethyl group;

X represents a fluorine atom, a difluoromethyl group or a trifluoromethyl group;

$X_5$ represents a bromine atom or iodine atom;

A represents a nitrogen atom or a C—H group; and

Y represents a single bond, O, S, a sulfoxide group or a sulfonyl group when A represents a nitrogen atom, and Y represents S, a sulfoxide group or a sulfonyl group when A represents a C—H group.

The compound represented by Formula (2) is also useful as a prolonged ectoparasite-controlling agent, or as a horticultural or agricultural insecticide, or for protecting a crop from a harmful organism. Therefore, the compound represented by Formula (2) can similarly be used in the compositions, mixtures, formulations, preparations, methods, uses and the like in which the compound represented by Formula (1) is used.

The compound represented by Formula (2) can be prepared with reference to methods known in the art, see e.g. WO 2005/073165, WO 2010/018714, WO 2011/093415 as well as WO2010/013567 and WO 2010/018857. Exemplary synthesis methods will be detailed in Examples 1 to 9.

The compound represented by Formula (2) is preferably selected from the group consisting of N-(2-fluoro-3-((2-iodo-4-(perfluoropropan-2-yl)-6-(trifluoromethyl)phenyl)carbamoyl)phenyl)-6-(trifluoromethyl)nicotinamide, N-(2-fluoro-3-((2-iodo-4-(perfluoropropan-2-yl)-6-(trifluoromethyl)phenyl)carbamoyl)phenyl)-N-methyl-6-(trifluoromethyl)nicotinamide, 6-fluoro-N-(2-fluoro-3-((2-iodo-4-(perfluoropropan-2-yl)-6-(trifluoromethyl)phenyl)carbamoyl)phenyl)nicotinamide, 6-fluoro-N-(2-fluoro-3-((2-iodo-4-(perfluoropropan-2-yl)-6-(trifluoromethyl)phenyl)carbamoyl)phenyl)-N-methylnicotinamide, 2-fluoro-3-(4-fluoro-N-methylbenzamido)-N-(2-iodo-4-(perfluoropropan-2-yl)-6-((trifluoromethyl)sulfonyl)phenyl)benzamide, and 2-fluoro-3-(4-fluorobenzamido)-N-(2-iodo-4-(perfluoropropan-2-yl)-6-((trifluoromethyl)sulfonyl)phenyl)benzamide.

The present invention will be further described in the following examples. However, these examples are not intended to limit the scope of the present application.

EXAMPLES

Example 1: Preparation of N-(2-fluoro-3-((2-iodo-4-(perfluoropropan-2-yl)-6-(trifluoromethyl)phenyl)carbamoyl)phenyl)-6-(trifluoromethyl)nicotinamide (Compound 67)

Step 1-A: Preparation of 4-(perfluoropropan-2-yl)-2-(trifluoromethyl)aniline

A 10 L, five-necked, round-bottomed flask equipped with an internal thermometer, a mechanical stirrer, a dropping funnel, a pH-controller (pH-electrode) and a condenser was charged with 2-aminobenzotrifluoride (98.8%, 450.0 g, 2760.6 mmol), tetrabutylammonium bromide (49.8 g, 154.6 mmol), ethyl acetate (2250.0 g, 25.5 mol), perfluoro-2-iodopropane (1.24 kg, 4.14 mol), and water (900.0 g). Sodium hydrosulfite (89%, 334.2 g, 1.54 mol) in 2.5 wt % $Na_2CO_3$ aq. (1.20 kg, 283.5 mmol) was added dropwisely to the vigorously stirred solution in the flask over 3 hr at 30° C. During the addition of $Na_2S_2O_4$ aq., the pH value of aqueous layer was adjusted to 4.4±0.1 using 18 wt % $Na_2CO_3$ aq. The resulting biphasic mixture was vigorously stirred for 3 hr at 30° C. After completion of the reaction, the two clear phases obtained were separated, and the organic layer was concentrated at 20 mmHg (40° C.) to remove solvents. The resulting residue was washed with 5 wt % $Na_2CO_3$ aq. (1.76 kg, 828.2 mmol) at 90° C. and water (1.62 kg) at 70° C., respectively, and a crude product was obtained as yellow liquid. The crude product was distilled in vacuum (3 mmHg) at 100° C. to give 763.9 g of 4-(perfluoropropan-2-yl)-2-(trifluoromethyl)aniline as yellow liquid (96.5 wt %) (yield 81.1%).

Step 1-B: Preparation of 2-iodo-4-(perfluoropropan-2-yl)-6-(trifluoromethyl)aniline A 3 L four necked, round-bottomed flask equipped with a mechanical stirrer, a thermometer, a reflux condenser and a dropping funnel (500 ml) was charged with 4-(perfluoropropan-2-yl)-2-(trifluoromethyl)aniline (as 100%; 340.0 g, 996.5 mmol), sulfuric acid (98 wt %, 19.9 g, 199.3 mmol) and methanol (1020.0 g). Iodine (99.5%, 151.8 g, 597.9 mmol) was added to the mixture at 20° C., and the resulting mixture was heated to 60° C. 50% Ammonium peroxodisulfate aq. (301.6 g, 647.7 mmol) was added dropwisely to the solution over 0.5 hr at 60° C. The resulting mixture was stirred at 60° C. for 5 hr. After completion of the reaction, excess amount of iodine was reduced by 10 wt % $Na_2SO_3$ aq. (208.4 g, 165.3 mmol). Then, water (1020.0 g) was added to the biphasic mixture. The two clear phases were separated, and the organic layer was washed with 10 wt % $Na_2CO_3$ aq. (105.6 g, 99.6 mmol) at 40° C. and 2.4 wt % NaCl aq. (697.0 g) at 40° C., respectively, to obtain the crude product (95.4 wt %, 464.4 g, 973.8 mmol) as dark red liquid. Distillation under reduced pressure (2.5 mmHg) gave 429.7 g of a fraction, b.p. 75-76° C. (2.5 mmHg), containing 97-98 wt % of 2-iodo-4-(perfluoropropan-2-yl)-6-(trifluoromethyl)aniline (yield 93.2%).

Step 1-C: Preparation of 2-fluoro-3-nitrobenzoyl chloride

A 10 L, four-necked, round-bottomed flask equipped with an internal thermometer, a mechanical stirrer, a dropping funnel, and a reflux condenser was charged with 2-fluoro-3-nitrobenzoic acid (1269 g, 6.86 mol), N,N-dimethylformamide (20.5 g) and toluene (4450 g). The suspension mixture was heated to 75° C., and thionylchloride (1227 g, 10.31 mol) was added dropwisely at 80° C. over 1 hr 55 min. The reaction mixture was stirred at 80° C. for 2 hr. After completion of the reaction, the solution was concentrated under reduced pressure at 40° C. 2-fluoro-3-nitrobenzoyl chloride was obtained as yellow oil (1529 g), and was used for the next step without further purification.

Step 1-D: Preparation of 2-fluoro-N-(2-iodo-4-(perfluoropropan-2-yl)-6-(trifluoromethyl)phenyl)-3-nitrobenzamide A 10 L, round-bottomed flask equipped with a mechanical stirrer, a thermometer, a reflux condenser, and a dropping funnel was charged with 2-iodo-4-(perfluoropropan-2-yl)-6-(trifluoromethyl)aniline (2600 g, 5.71 mol), 1,3-dimethylimidazolidin-2-one (4200 g), and diisopropylethylamine (1774 g, 13.73 mol). 2-fluoro-3-nitrobenzoyl chloride (1529 g) was added to the suspension at 20° C., and the resulting mixture was heated to 105° C., and stirred for 5 hr at this temperature. After cooling the reaction mixture to 20° C., water (7800 g) and ethyl acetate (13.0 L) were added. The resulting two layers were separated, and the organic layer was washed with 10% HCl aq. (3900 g) and sat. NaCl aq. (4000 g), with sat. NaHCO$_3$ aq. (4000 g) and sat. NaCl aq. (4000 g), and with sat. NaCl aq. (8000 g) successively, then concentrated to give a crude product (4050 g). The obtained crude product was purified with column chromatography (silica gel: 12000 g, eluent: ethyl acetate/n-hexane=1/3, 70.0 L). Diisopropylether (7.0 L) and n-hexane (7.0 L) were added to the purified product, and the resulting mixture was stirred overnight. After filtration, the obtained solid was washed with diisopropylether (3.5 L)/n-hexane (3.5 L), and dried under reduced pressure to give 2-fluoro-N-(2-iodo-4-(perfluoropropan-2-yl)-6-(trifluoromethyl)phenyl)-3-nitrobenzamide (2518 g, yield 70.8%).

Step 1-E: Preparation of 3-amino-2-fluoro-N-(2-iodo-4-(perfluoropropan-2-yl)-6-(trifluoromethyl)phenyl)benzamide 20 L, four-necked, round-bottomed flask equipped with an internal thermometer, a mechanical stirrer, a dropping funnel, and a reflux condenser was charged with 2-fluoro-N-(2-iodo-4-(perfluoropropan-2-yl)-6-(trifluoromethyl)phenyl)-3-nitrobenzamide (2518 g, 4.05 mol), ethanol (9950 g) and water (2180 g). After heating to 50° C., conc. HCl (16.9 g, 0.16 mol) was added dropwisely to the suspension. Fe (565 g 10.12 mol) was added in 11 portions (about 50 g each) at 60° C. over 3 hr, and the reaction mixture was stirred at 65° C. After 3 hr, conc. HCl (17.0 g, 0.16 mol) was added additionally and the mixture was stirred at 65° C. for 3 hr again. After cooling to 20° C., the resulting mixture was filtrated through CELITE© pad, the filter cake was washed with ethanol (3.0 L), and the filtrate was concentrated at 50° C. The obtained residue was dissolved in ethyl acetate (5.0 L) and washed with water (5.0 L). The organic layer was dried over Na$_2$SO$_4$ (500 g) and concentrated at 40° C., to give a crude product (2650 g). The crude product thus obtained was stirred with diisopropylether (2.7 L) and n-hexane (2.7 L) at room temperature for 4 hr. After filtration, the obtained solid was washed with diisopropylether/n-hexane=1/1 (2.7 L) and dried under reduced pressure to give 3-amino-2-fluoro-N-(2-iodo-4-(perfluoropropan-2-yl)-6-(trifluoromethyl)phenyl)benzamide (2268 g, yield 94.6%).

Step 1-F: Preparation of 6-(trifluoromethyl)nicotinoyl chloride

A 5 L, four-necked, round-bottomed flask equipped with an internal thermometer, a mechanical stirrer, a dropping funnel, and a reflux condenser was charged with 6-(trifluoromethyl)nicotinic acid (782 g, 4.09 mol), N,N-dimethylformamide (10.6 g) and toluene (2340 g). After heating the mixture to 80° C., thionylchloride (878 g, 7.38 mol) was added dropwisely over 1.5 hr. After stirring at 80° C. for 2 hr, the mixture was cooled to 40° C. and concentrated under reduced pressure at 50° C., to give 6-(trifluoromethyl) nicotinoyl chloride (786 g) as yellow oil. The 6-(trifluoromethyl)nicotinoyl chloride obtained was used for the next step without further purification.

Step 1-G: Preparation of N-(2-fluoro-3-((2-iodo-4-(perfluoropropan-2-yl)-6-(trifluoromethyl)phenyl)carbamoyl)phenyl)-6-(trifluoromethyl)nicotinamide (Compound 67)

A 20 L, four necked, round-bottomed flask equipped with a mechanical stirrer, a thermometer, a reflux condenser, and a dropping funnel was charged with 6-(trifluoromethyl) nicotinoyl chloride (786 g), 3-amino-2-fluoro-N-(2-iodo-4-(perfluoropropan-2-yl)-6-(trifluoromethyl)phenyl)benzamide (2019 g, 3.41 mol) and tetrahydrofuran (5390 g). Pyridine (907 g) was added dropwisely over 0.5 hr, and the resulting mixture was stirred at 20° C. for 2 hr. After completion of the reaction, water (7800 g), ethyl acetate (13 L) and sat. NaCl aq. (2510 g) was added to the reaction mixture and the resulting two layers were separated. The organic layer was washed with 1N HCl aq. (ca.2000 g) and sat. NaCl.aq. (ca.2500 g), (three times), with sat. NaHCO$_3$ (4000 g) and sat. NaCl aq. (1000 g) and with sat. NaCl aq. (4000 g) successively. The organic layer was dried over sodium sulfate (1000 g) and concentrated at 40° C. Ethyl acetate (5.0 L) was added to the obtained residue, and the resulting solution was dried over sodium sulfate (500 g) again and concentrated at 40° C. to give a crude product The obtained crude product was stirred with n-hexane (6.0 L) and diisopropylether (6.0 L) at room temperature overnight. After filtration, the obtained solid was washed with diisopropylether/n-hexane (1/1, 4.0 L) and dried under reduced pressure at 40° C. for 6 hr to give N-(2-fluoro-3-((2-iodo-4-(perfluoropropan-2-yl)-6-(trifluoromethyl)phenyl)carbamoyl)phenyl)-6-(trifluoromethyl)nicotinamide (2461 g, yield 94.3%).

Example 2: Preparation of N-(2-fluoro-3-((2-bromo-4-(perfluoropropan-2-yl)-6-(trifluoromethoxy)phenyl)carbamoyl)phenyl)-6-(trifluoromethyl)nicotinamide (Compound 99)

Step 2-A: Preparation of 4-(perfluoropropan-2-yl)-6-(trifluoromethoxy)aniline

According to the method of Step 1-A of Example 1, 4-(perfluoropropan-2-yl)-6-(trifluoromethoxy)aniline was prepared from 2-trifluoromethoxyaniline.

Step 2-B: Preparation of 2-bromo-4-(perfluoropropan-2-yl)-6-(trifluoromethoxy)aniline N-Bromosuccinimide (4.33 g, 24.3 mmol) was added portionwisely to a N,N-dimethylformamide (42 mL) solution of 4-(perfluoropropan-2-yl)-6-(trifluoromethoxy)aniline (7.0 g, 20.3 mmol), and the resulting mixture was stirred at room temperature overnight. Water and ethyl acetate were added to the mixture, and the resulting two layers were separated. The obtained organic layer was washed with sat. NaCl aq., was dried over Na$_2$SO$_4$ and was concentrated to give a crude product. The crude product thus obtained was purified with column chromatography (silica gel, eluent: ethyl acetate/n-hexane gradient=from 0/100 to 10/90) to give 2-bromo-4-(perfluoropropan-2-yl)-6-(trifluoromethoxy)aniline (5.6 g, yield 65%) as orange-colored oil.

Step 2-C: Preparation of 2-fluoro-N-(2-bromo-4-(perfluoropropan-2-yl)-6-(trifluoromethoxy)phenyl)-3-nitrobenzamide 2-Fluoro-3-nitrobenzoic acid (2.91 g 15.7 mmol) was stirred with toluene (13 mL), and thionylchloride (5.7 mL, 78.3 mmol) and N,N-dimethylformamide (2 drops) were added. The resulting mixture was stirred at 90° C. for 0.5 hr and concentrated to give an acid chloride. The acid chloride thus obtained was added to the mixture of 2-bromo-4-(perfluoropropan-2-yl)-6-(trifluoromethoxy)aniline (5.5 g 13.1 mmol), 1,3-dimethylimidazolidin-2-one (8.5 mL) and diisopropylethylamine (5.43 mL 31.1 mmol), the resulting mixture was heated to 110° C. and stirred for 3 hr at this temperature. After cooling the reaction mixture to room temperature, water and ethyl acetate were added and the resulting two layers were separated. The obtained organic layer was washed with 1N HCl aq., sat. NaHCO$_3$ aq. and sat. NaCl aq. successively, then concentrated to give a crude product. The obtained crude product was purified with column chromatography (silica gel, eluent: ethyl acetate/n-heptane gradient=from 5/95 to 15/85). Then diisopropyl-ether/n-heptane=1/1 (160 mL) was added to the purified product, and the resulting mixture was stirred. After filtration, 2-fluoro-N-(2-bromo-4-(perfluoropropan-2-yl)-6-(trifluoromethoxy)phenyl)-3-nitrobenzamide (4.9 g, yield 59%) was obtained.

Step 2-D: Preparation of 3-amino-2-fluoro-N-(2-bromo-4-(perfluoropropan-2-yl)-6-(trifluoromethoxy)phenyl)benzamide 2-Fluoro-N-(2-bromo-4-(perfluoropropan-2-yl)-6-(trifluoromethoxy)phenyl)-3-nitrobenzamide (4.9 g, 8.3 mmol) was dissolved in ethanol (39 mL), and SnCl$_2$ (4.92 g, 25.9 mmol) was added portionwisely under cooling. After conc. HCl (5.35 g, 9.04 mmol) was added dropwisely to the suspension, the resulting mixture was heated to 50° C. After 1.5 hr, the mixture was cooled to room temperature, and 10% NaOH aq. (80 mL) was added. After filtration through CELITE© pad, the resulting filtrate was concentrated, dissolved in ethyl acetate and washed with water and sat. NaCl aq. successively. The organic layer was dried over Na$_2$SO$_4$ and concentrated to give a crude product. The crude product thus obtained was purified with column chromatography (silica gel, eluent: ethyl acetate/n-heptane gradient=from 20/80 to 25/75) to give 3-amino-2-fluoro-N-(2-bromo-4-(perfluoropropan-2-yl)-6-(trifluoromethoxy)phenyl)benzamide as pale red solid (4.8 g).

Step 2-E: Preparation of N-(2-fluoro-3-((2-bromo-4-(perfluoropropan-2-yl)-6-(trifluoromethoxy)phenyl)carbamoyl)phenyl)-6-(trifluoromethyl)nicotinamide (Compound 99)

6-(Trifluoromethyl)nicotinic acid (100 mg) was stirred with toluene, and thionylchloride (60 μL) and N,N-dimethylformamide (1 drops) were added to the mixture. The resulting mixture was stirred at 90° C. for 2 hr and concentrated to give an acid chloride. The acid chloride thus obtained was added to a tetrahydrofuran solution of 3-amino-2-fluoro-N-(2-bromo-4-(perfluoropropan-2-yl)-6-(trifluoromethoxy)phenyl)benzamide (300 mg). Pyridine (100 μL) was added, and the resulting mixture was stirred at room temperature for overnight. Water and ethyl acetate were added to the reaction mixture, and the resulting two layers were separated. The organic layer was concentrated, and the crude product thus obtained was purified with column chromatography (silica gel, eluent: ethyl acetate/n-hexane) to give N-(2-fluoro-3-((2-bromo-4-(perfluoropropan-2-yl)-6-(trifluoromethoxy)phenyl)carbamoyl)phenyl)-6-(trifluoromethyl)nicotinamide.

Example 3: Preparation of N-(2-fluoro-3-((2-iodo-4-(perfluoropropan-2-yl)-6-(trifluoromethoxy)phenyl)carbamoyl)phenyl)-6-(trifluoromethyl)nicotinamide (Compound 118)

Step 3-A: Preparation of 2-iodo-4-(perfluoropropan-2-yl)-6-(trifluoromethoxy)aniline Sulfuric acid (0.87 g, 0.1 eq) and iodine (6.29 g, 24.8 mmol) were added to a methanol (45 g) solution of 4-(perfluoropropan-2-yl)-6-(trifluoromethoxy)aniline (15.0 g, 43.5 mmol), and the resulting mixture was heated to 60° C. 50.5% ammonium peroxodisulfate aq. (6.43 g, 28.1 mmol) was added dropwisely to the solution at 60° C. After stirring at 60° C. for 4 hr, the resulting mixture was cooled to room temperature, and 10 wt % Na$_2$SO$_3$ aq. (60 mL) was added. After stirring for 0.5 hr, n-hexane was added, and the resulting two clear phases were separated. Then, the organic layer was washed with sat. NaCl aq. and concentrated. The obtained crude product was purified with column chromatography (silica gel: eluent: n-hexane) to give 2-iodo-4-(perfluoropropan-2-yl)-6-(trifluoromethoxy)aniline as yellow oil (13.5 g yield 65.8%).

Step 3-C: Preparation of 2-fluoro-N-(2-iodo-4-(perfluoropropan-2-yl)-6-(trifluomethoxy)phenyl)-3-nitrobenzamide 2-Fluoro-3-nitrobenzoic acid (5.4 g 29.6 mmol) was stirred with toluene (25 mL), and thionylchloride (10.7 mL, 147 mmol) and N,N-dimethylformamide (2 drops) were added. The resulting mixture was stirred at 90° C. for 0.5 hr and concentrated to give an acid chloride. The acid chloride thus obtained was added to the suspension of 2-iodo-4-(perfluoropropan-2-yl)-6-(trifluoromethoxy)aniline (11.6 g 24.6 mmol), 1,3-dimethylimidazolidin-2-one (17 mL) and diisopropylethylamine (10.2 mL 58.6 mmol), and the resulting mixture was heated to 110° C. and stirred for 3 hr at this temperature. After cooling the reaction mixture to room temperature, water and ethyl acetate were added, and the resulting two layers were separated. The obtained organic layer was washed with 1N HCl aq., sat. NaHCO$_3$ aq. and sat. NaCl aq. successively, then concentrated to give a crude product. The obtained crude product was purified with column chromatography (silica gel, eluent: ethyl acetate/n-heptane gradient=from 5/95 to 15/85). Then diisopropyl-ether/n-heptane=1/1 (160 mL) was added to the purified product, and the resulting mixture was stirred. After filtration, 2-fluoro-N-(2-iodo-4-(perfluoropropan-2-yl)-6-(trifluoromethoxy)phenyl)-3-nitrobenzamide (9.9 g, yield 63%) was obtained.

Step 3-D: Preparation of 3-amino-2-fluoro-N-(2-iodo-4-(perfluoropropan-2-yl)-6-(trfluoromethoxy)phenyl)benzamide 2-Fluoro-N-(2-iodo-4-(perfluoropropan-2-yl)-6-(trifluoromethoxy)phenyl)-3-nitrobenzamide (11.2 g, 8.31 mmol) was dissolved in ethanol (89 mL), and SnCl$_2$ (10.3 g, 54.4 mmol) was added portionwisely under cooling. After conc. HCl (12.1 g, 18.9 mmol) was added dropwisely to the suspension, the resulting mixture was heated to 50° C. After 1 hr, the mixture was cooled to room temperature, and 10% NaOH aq. (80 mL) was added. After filtration through CELITE© pad, the filtrate was concentrated, dissolved in ethyl acetate and washed with water and sat. NaCl aq. successively. The organic layer was dried over Na$_2$SO$_4$ and concentrated to give a crude product. The crude product thus obtained was purified with column chromatography (silica gel, eluent: ethyl acetate/n-heptane gradient=from 15/85 to 30/70) to give 3-amino-2-fluoro-N-(2-iodo-4-(perfluoropropan-2-yl)-6-(trifluoromethoxy)phenyl)benzamide as pale red solid (12 g).

Step 3-E: Preparation of N-(2-fluoro-3-((2-iodo-4-(perfluoropropan-2-yl)-6-(trifluoromethoxy)phenyl)carbamoyl)phenyl)-6-(trifluoromethyl)nicotinamide (Compound 118)

According to the method of Step 2-E of Example 2, N-(2-fluoro-3-((2-iodo-4-(perfluoropropan-2-yl)-6-(trifluoromethoxy)phenyl)carbamoyl)phenyl)-6-(trifluoromethyl)nicotinamide was prepared from 6-(trifluoromethyl)nicotinic acid and 3-amino-2-fluoro-N-(2-iodo-4-(perfluoropropan-2-yl)-6-(trifluoromethoxy)phenyl)benzamide.

Example 4: Preparation of N-(2-fluoro-3-((2-iodo-4-(perfluoropropan-2-yl)-6-(trifluoromethoxy)phenyl)carbamoyl)phenyl)-N-methyl-6-(trifluoromethyl)nicotinamide (Compound 117)

Step 4-A: Preparation of 2-fluoro-N-(2-iodo-4-(perfluoropropan-2-yl)-6-(trifluoromethoxy)phenyl)-3-(methylamino)benzamide 3-Amino-2-fluoro-N-(2-iodo-4-(perfluoropropan-2-yl)-6-(trifluoromethoxy)phenyl)benzamide (4.0 g, 6.5 mmol) was dissolved in sulfuric acid (51 mL, 963 mmol), and formalin (10 mL) was added dropwisely to the solution. During the addition, the temperature of the solution was controlled below 25° C. by cooling with ice-water bath. After stirring at room temperature for 65 hr, the reaction mixture was added dropwisely to 5 N NaOH aq. (300 mL). Water and ethyl acetate were added to the mixture, and the resulting two layers were separated. The obtained organic layer was dried over $Na_2SO_4$ and concentrated to give 2-fluoro-N-(2-iodo-4-(perfluoropropan-2-yl)-6-(trifluoromethoxy)phenyl)-3-(methylamino)benzamide (4.65 g).

Step 4-B: Preparation of N-(2-fluoro-3-((2-iodo-4-(perfluoropropan-2-yl)-6-(trifluoromethoxy)phenyl)carbamoyl)phenyl)-N-methyl-6-(trifluoromethyl)nicotinamide (Compound 117)

According to the method of Step 2-E of Example 2, N-(2-fluoro-3-((2-iodo-4-(perfluoropropan-2-yl)-6-(trifluoromethoxy)phenyl)carbamoyl)phenyl)-N-methyl-6-(trifluoromethyl)nicotinamide was prepared from 6-(trifluoromethyl)nicotinic acid and 2-fluoro-N-(2-iodo-4-(perfluoropropan-2-yl)-6-(trifluoromethoxy)phenyl)-3-(methylamino)benzamide.

Example 5: Preparation of N-(2-fluoro-3-((2-iodo-4-(perfluoropropan-2-yl)-6-(trifluoromethyl)phenyl)carbamoyl)phenyl)-N-methyl-6-(trifluoromethyl)nicotinamide (Compound 66)

Step 5-A: Preparation of 2-fluoro-N-(2-iodo-4-(perfluoropropan-2-yl)-6-(trifluoromethyl)phenyl)-3-(methylamino)benzamide According to the method of Step 4-A of Example 4, 2-fluoro-N-(2-iodo-4-(perfluoropropan-2-yl)-6-(trifluoromethyl)phenyl)-3-(methylamino)benzamide was prepared from 3-amino-2-fluoro-N-(2-iodo-4-(perfluoropropan-2-yl)-6-(trifluoromethyl)phenyl)benzamide.

Step 5-B: Preparation of N-(2-fluoro-3-((2-iodo-4-(perfluoropropan-2-yl)-6-(trifluoromethyl)phenyl)carbamoyl)phenyl)-N-methyl-6-(trifluoromethyl)nicotinamide (Compound 66)

According to the method of Step 2-E of Example 2, N-(2-fluoro-3-((2-iodo-4-(perfluoropropan-2-yl)-6-(trifluoromethyl)phenyl)carbamoyl)phenyl)-N-methyl-6-(trifluoromethyl)nicotinamide was prepared from 6-(trifluoromethyl)nicotinic acid and 2-fluoro-N-(2-iodo-4-(perfluoropropan-2-yl)-6-(trifluoromethyl)phenyl)-3-(methylamino)benzamide.

Example 6: Preparation of 6-fluoro-N-(2-fluoro-3-((2-iodo-4-(perfluoropropan-2-yl)-6-(trifluoromethyl)phenyl)carbamoyl)phenyl)nicotinamide (Compound 116)

6-fluoronicotinic acid (21.45 g) was stirred with toluene (115 mL), and thionylchloride (27.7 mL, 380 mmol) and N,N-dimethylformamide (0.49 mL) were added to the mixture. The resulting mixture was stirred under reflux for 2 hr and concentrated to give an acid chloride. The acid chloride thus obtained was added to a tetrahydrofuran solution of 3-amino-2-fluoro-N-(2-iodo-4-(perfluoropropan-2-yl)-6-(trifluoromethyl)phenyl)benzamide (75 g, 127 mmol). Diisopropylethylamine (26.5 mL, 152 mmol) was added dropwisely, and the resulting mixture was stirred at room temperature. Water and ethyl acetate were added to the reaction mixture, and the resulting two layers were separated. The organic layer was dried over $Na_2SO_4$, concentrated, and the crude product thus obtained was washed with diisopropylether (500 mL 6 times 40° C. 2 hr each), acetonitrile (400 mL twice 40° C. 1 hr each) and n-heptane (500 mL 6 times 40° C. each) to give 6-fluoro-N-(2-fluoro-3-((2-iodo-4-(perfluoropropan-2-yl)-6-(trifluoromethyl)phenyl)carbamoyl)phenyl)nicotinamide (78 g, 109 mmol 86% yield) as white solid.

Example 7: Preparation of 6-fluoro-N-(2-fluoro-3-((2-iodo-4-(perfluoropropan-2-yl)-6-(trifluoromethyl)phenyl)carbamoyl)phenyl)-N-methylnicotinamide (Compound 115)

According to the method of Step 2-E of Example 2, 6-fluoro-N-(2-fluoro-3-((2-iodo-4-(perfluoropropan-2-yl)-6-(trifluoromethyl)phenyl)carbamoyl)phenyl)-N-methylnicotinamide was prepared from 2-fluoro-N-(2-iodo-4-(perfluoropropan-2-yl)-6-(trifluoromethyl)phenyl)-3-(methylamino)benzamide.

Example 8: Preparation of 2-fluoro-3-(4-fluoro-N-methylbenzamido)-N-(2-iodo-4-(perfluoropropan-2-yl)-6-((trifluoromethyl)sulfonyl)phenyl)benzamide (Compound 70)

Step 8-A: Preparation of 4-(perfluoropropan-2-yl)-2-((trifluoromethyl)thio)aniline According to the method of Step 1-A of Example 1, 4-(perfluoropropan-2-yl)-2-((trifluoromethyl)thio)aniline was prepared from 2-((trifluoromethyl)thio)aniline.

Step 8-B: Preparation of 2-iodo-4-(perfluoropropan-2-yl)-6-((trifluoromethyl)thio)aniline Sulfuric acid (8.99 mL, 169 mmol) and iodine (65.21 g, 514 mmol) were added to a methanol (1104 mL) solution of 4-(perfluoropropan-2-yl)-2-((trifluoromethyl)thio)aniline (290 g, 803 mmol), and the resulting mixture was heated to 60° C. 50% Ammonium peroxodisulfate aq. (119.09 g, 522 mmol) was added dropwisely to the solution at 60° C. After stirring at 60° C. for 2 hr, iodine (21.4 g, 169 mmol) and ammonium peroxodisulfate (17.29 g, 361 mmol) were added and stirred at 60° C. for 1 hr. The resulting mixture was cooled to room temperature and an aqueous solution (450 mL) of $Na_2SO_3$ (17.29 g) and water (593 mL) was added. The resulting mixture was extracted with n-heptane (4470 mL), and the obtained organic layer was washed with sat. NaCl aq., dried over $Na_2SO_4$ and concentrated. The obtained crude product was purified with column chromatography (silica gel: eluent: ethyl acetate/n-heptane=1/9) to give 2-iodo-4-(perfluoropropan-2-yl)-6-((trifluoromethyl)thio)aniline as yellow oil (297 g yield 76%).

Step 8-C: Preparation of 2-fluoro-N-(2-iodo-4-(perfluoropropan-2-yl)-6-((trifluoromethyl)thio)phenyl)-3-nitrobenzamide A 2 L, round-bottomed flask equipped with a reflux condenser was charged with 2-fluoro-3-nitrobenzoic acid (118.76 g, 642 mmol) and toluene (656 mL). N,N-Dimethylformamide (20.5 g) and thionylchloride (71.1 mL, 975 mmol) were added, and the resulting mixture was stirred at 90° C. for 1.5 hr. After completion of the reaction, the mixture was concentrated under reduced pressure to give an acid chloride.

A 3 L, round-bottomed flask equipped with a mechanical stirrer, a thermometer and a reflux condenser was charged with 2-iodo-4-(perfluoropropan-2-yl)-6-((trifluoromethyl)thio)aniline (250 g, 513 mmol), 1,3-dimethylimidazolidin-2-one (365 mL), and diisopropylethylamine (215 mL, 1232 mmol). A 1,3-dimethylimidazolidin-2-one solution of the above acid chloride was added at 27° C., the resulting mixture was heated to 105° C., and stirred for 3.5 hr at this temperature. After cooling the reaction mixture to room temperature, water (1 L) and ethyl acetate (1.3 L) were added. The resulting two layers were separated, and the organic layer was washed with 10% HCl aq. (1 L), sat. NaHCO$_3$ aq. (1 L) and sat. NaCl aq. (1 L) successively, then concentrated to give a crude product (380 g). The obtained crude product was purified with column chromatography (silica gel: 5 kg, eluent: ethyl acetate/n-heptane=1/3). n-Heptane (1 L) was added to the purified product, and the resulting mixture was stirred overnight. After filtration, the obtained solid was washed with n-heptane (1.3 L), and dried under reduced pressure to give 2-fluoro-N-(2-iodo-4-(perfluoropropan-2-yl)-6-((trifluoromethyl)thio)phenyl)-3-nitrobenzamide (292 g, yield 87%) as orange-colored solid.

Step 8-D: Preparation of 3-amino-2-fluoro-N-(2-iodo-4-(perfluoropropan-2-yl)-6-((trifluoromethyl)thio)phenyl) benzamide A 3 L, four-necked, round-bottomed flask equipped with an internal thermometer, a mechanical stirrer, and a reflux condenser was charged with 2-fluoro-N-(2-iodo-4-(perfluoropropan-2-yl)-6-((trifluoromethyl)thio)phenyl)-3-nitrobenzamide (265 g, 405 mmol), ethanol (1419 mL), water (226 mL) and conc. HCl (1.661 mL, 57.4 mmol). After heating to 60° C., Fe (565 g 10.12 mol) was added portionwisely and stirred for 1 hr. After cooling to room temperature, the resulting mixture was filtrated through CELITE© pad, and the filter cake was washed with ethyl acetate (1 L 4 times). After concentration of the filtrate at 40° C., the obtained residue was dissolved in ethyl acetate (1.6 L) and washed with water (1 L) and sat. NaCl aq. (1 L) successively. The organic layer was dried over Na$_2$SO$_4$ and concentrated to give a crude product. The crude product thus obtained was stirred with n-heptane at 40° C. After filtration, the obtained solid was washed with n-heptane and dried under reduced pressure to give 3-amino-2-fluoro-N-(2-iodo-4-(perfluoropropan-2-yl)-6-((trifluoromethyl)thio)phenyl)benzamide (228 g, yield 95%)

Step 8-E: Preparation of 2-fluoro-3-(4-fluorobenzamido)-N-(2-iodo-4-(perfluoropropan-2-yl)-6-((trifluoromethyl)thio)phenyl)benzamide 4-Fluorobenzoyl chloride (63.41 g, 0.4 mol) was added to a tetrahydrofuran (2.41 L) solution of 3-amino-2-fluoro-N-(2-iodo-4-(perfluoropropan-2-yl)-6-((trifluoromethyl)thio)phenyl)benzamide (207.0 g, 0.333 mol). Pyridine (31.63 g) was added, and the resulting mixture was stirred at room temperature for 2 hr. After completion of the reaction, water (3.5 L) and ethyl acetate (3.5 L) were added to the reaction mixture, and the resulting two layers were separated. The organic layer was washed with 10% HCl aq. (3.5 L), sat. NaHCO$_3$ (3.5 L) and sat. NaCl aq. (3.5 L) successively, dried over sodium sulfate and concentrated to give a crude product. The obtained crude product was washed with n-heptane/acetone and n-heptane successively, and dried under reduced pressure to give 2-fluoro-3-(4-fluorobenzamido)-N-(2-iodo-4-(perfluoropropan-2-yl)-6-((trifluoromethyl)thio)phenyl)benzamide (252 g, yield 92.5%).

Step 8-F: Preparation of 2-fluoro-3-(4-fluoro-N-methylbenzamido)-N-(2-iodo-4-(perfluoropropan-2-yl)-6-((trifluoromethyl)sulfonyl)phenyl)benzamide (Compound 70)

20 L, five-necked, round-bottomed flask equipped with an internal thermometer and a mechanical stirrer was charged with 2-fluoro-3-(4-fluorobenzamido)-N-(2-iodo-4-(perfluoropropan-2-yl)-6-((trifluoromethyl)thio)phenyl)benzamide (163 g, 218 mmol), water (4371 mL), acetonitrile (2202 mL) and dichloromethane (2192 mL), then sodium periodate (214.89 g, 1005 mmol) and RuCl$_3$ (4.36 g, 65.3 mmol) were added. After stirring for 1 hr at room temperature, an aqueous solution (3 L) of sodium thiosulfate (345.3 g, 2184 mmol) was added, and the mixture was stirred for 0.5 hr additionally. The resulting mixture was extracted with ethyl acetate (3 L, 4 times) and the combined organic layer was dried over sodium sulfate and concentrated to give a crude product. The crude product thus obtained was stirred with ethyl acetate (500 mL) for 2 hr. After filtration, the obtained solid was washed with ethyl acetate (100 mL) and dried under reduced pressure for 2 days to give 2-fluoro-3-(4-fluoro-N-methylbenzamido)-N-(2-iodo-4-(perfluoropropan-2-yl)-6-((trifluoromethyl)sulfonyl)phenyl)benzamide (103 g, 132 mmol, yield 60.6%).

Example 9: Preparation of 2-fluoro-3-(4-fluoro-N-methylbenzamido)-N-(2-iodo-4-(perfluoropropan-2-yl)-6-((trifluoromethyl)sulfonyl)phenyl)benzamide (Compound 70)

Step 9-A: Preparation of 2-fluoro-N-(2-iodo-4-(perfluoropropan-2-yl)-6-((trifluoromethyl)thio)phenyl)-3-(methylamino)benzamide According to the method of Step 4-A of Example 4, 2-fluoro-N-(2-iodo-4-(perfluoropropan-2-yl)-6-((trifluoromethyl)thio)phenyl)-3-(methylamino)benzamide was prepared from 3-amino-2-fluoro-N-(2-iodo-4-(perfluoropropan-2-yl)-6-((trifluoromethyl)thio)phenyl)benzamide Step 9-B: Preparation of 2-fluoro-3-(4-fluoro-N-methylbenzamido)-N-(2-iodo-4-(perfluoropropan-2-yl)-6-((trifluoromethyl)thio)phenyl)benzamide According to the method of Step 2-E of Example 2, 2-fluoro-3-(4-fluoro-N-methylbenzamido)-N-(2-iodo-4-(perfluoropropan-2-yl)-6-((trifluoromethyl)thio)phenyl)benzamide was prepared from 2-fluoro-N-(2-iodo-4-(perfluoropropan-2-yl)-6-((trifluoromethyl)thio)phenyl)-3-(methylamino)benzamide.

Step 9-C: Preparation of 2-fluoro-3-(4-fluoro-N-methylbenzamido)-N-(2-iodo-4-(perfluoropropan-2-yl)-6-((trifluoromethyl)sulfonyl)phenyl)benzamide (Compound 70)

According to the method of Step 8-F of Example 8, 2-fluoro-3-(4-fluoro-N-methylbenzamido)-N-(2-iodo-4-(perfluoropropan-2-yl)-6-((trifluoromethyl)sulfonyl)phenyl)benzamide was prepared from 2-fluoro-3-(4-fluoro-N-methylbenzamido)-N-(2-iodo-4-(perfluoropropan-2-yl)-6-((trifluoromethyl)thio)phenyl)benzamide.

Compounds according to the invention shown in the following Table 242 were produced in the same manner as Examples 1 or by using any one of methods disclosed in WO 2005/073165, WO 2010/018714, WO 2011/093415, WO2010/013567 or WO 2010/018857. The Compound No. in Table 242 corresponds to the structure of the compound exemplified in Table 241.

TABLE 242

| Compound No. | MS | ¹H-NMR |
|---|---|---|
| 44 | 801 (M + 23) | ¹H-NMR (DMSO-$d_6$) δ: 10.47 (1H, s), 8.45 (1H, s), 7.92 (1H, s), 7.68-7.64 (2H, m), 7.55 (1H, s), 7.50 (1H, d, J = 8.3 Hz), 7.35 (1H, t, J = 7.8 Hz), 7.25 (1H, d, J = 7.8 Hz), 3.36 (3H, s). |
| 45 | | ¹H-NMR (CDCl$_3$) δ: 8.33 (1H, s), 8.12-8.03 (2H, m), 7.92 (1H, s), 7.76-7.72 (2H, m), 7.50-7.42 (3H, m), 7.33-7.32 (1H, m), 5.00 (1H, br s), 3.51 (3H, s). |
| 46 | 804 (M + 1) | ¹H-NMR (CDCl$_3$) δ: 8.36-8.34 (2H, br m), 8.00-7.94 (3H, m), 7.43-7.41 (2H, br m), 7.08-7.06 (1H, br m), 6.91-6.89 (1H, br m), 3.53 (3H, s), 2.36 (3H, s). |
| 47 | | ¹H-NMR (CDCl$_3$) δ: 8.33 (1H, s), 8.11(1H, br s), 8.01 (1H, t, J = 6.6 Hz), 7.92 (1H, s), 7.48 (1H, t, J = 6.6 Hz), 7.30-7.27 (4H, m), 7.07 (2H, d, J = 5.2 Hz), 3.50 (3H, s), 2.85-2.79 (1H, m), 1.16(6H, d, J = 6.7 Hz). |
| 48 | | ¹H-NMR(CDCl$_3$)δ: 8.33 (1H, s), 8.10 (1H, br-s), 8.01 (1H, t, J = 6.6 Hz), 7.92 (1H, s), 7.62 (2H, s), 7.47-7.27 (4H, m), 6.12 (1H, s), 5.73 (1H, s), 3.51 (3H, s). |
| 49 | | ¹H-NMR (CDCl$_3$) δ: 8.33 (1H, s), 8.06 (2H, m), 7.92 (1H, m), 7.81 (2H, m), 7.52 (3H, m), 7.35-7.32 (1H, m), 3.55 (3H, s), 3.00 (3H, s) |
| 50 | | ¹H-NMR (CDCl$_3$) δ: 8.33 (1H, s), 8.12-8.00 (2H, m), 7.93 (1H, s), 7.46-7.43 (1H, m), 7.30-7.26 (1H, m), 6.93-6.89 (2H, m), 6.66-6.64 (2H, m), 3.82 (3H, s), 3.73 (3H, s), 3.51 (3H, s). |
| 51 | | ¹H-NMR (CDCl$_3$) δ: 8.34 (1H, s), 8.11-8.05 (2H, m), 7.93 (1H, s), 7.49-7.46 (1H, m), 7.34-7.31 (1H, m), 7.26 (1H, m), 7.02-7.00 (2H, m) |
| 52 | 787 (M + 23)<br>765 (M + H)<br>763 (M − H) | ¹H-NMR (CDCl$_3$) δ: 8.33 (1H, s), 8.16 (1H, s), 8.03-8.00 (1H, m), 7.93 (1H, s), 7.47 (1H, t, J = 7.3 Hz), 7.29-7.27 (1H, m), 7.14-7.12 (1H, m), 6.95 (1H, br s), 6.85 (1H, br s), 3.49 (3H, s), 2.81 (1H, br s), 2.66-2.62 (4H, br m), 1.83-1.80 (1H, m), 1.71 (2H, br s). |
| 53 | | ¹H-NMR (CDCl$_3$) δ: 8.32 (1H, br s), 8.05-7.97 (2H, m), 7.92 (1H, bs), 7.52 (1H, br s), 7.32 (1H, m), 7.26 (2H, m), 7.03 (2H, m), 3.52 (3H, s), 2.42 (3H, s) |
| 54 | 778 (M + 23) | ¹H-NMR (CDCl$_3$) δ: 8.34 (1H, s), 8.08-8.06 (4H, br m), 7.93 (1H, s), 7.49-7.47 (3H, br m), 7.34-7.32 (1H, br m), 3.55 (3H, s). |
| 55 | 755 (M + 1) | ¹H-NMR (DMSO-$d_6$) δ: 10.47 (1H, s), 8.46 (1H, s), 7.92 (1H, s), 7.63-7.56 (2H, m), 7.32 (1H, t, J = 7.8 Hz), 6.85 (2H, dt, J = 15.2, 5.5 Hz), 6.76 (1H, d, J = 8.0 Hz), 5.98 (2H, s), 3.32 (3H, s). |
| 56 | | ¹H-NMR (DMSO-$d_6$, 70° C.) δ: 10.45 (1H, br s), 8.46 (1H, s), 7.93 (1H, s), 7.63-7.59 (2H, m), 7.44 (1H, br s), 7.31 (1H, br s), 7.08-7.01 (2H, m), 3.36 (3H, s). |
| 57 | | ¹H-NMR (DMSO-$d_6$, 70° C.) δ: 10.47 (1H, br s), 8.64 (1H, br s), 8.46 (1H, s), 7.96-7.94 (3H, m), 7.74 (1H, t, J = 7.0 Hz), 7.65 (1H, t, J = 6.4 Hz), 7.37 (1H, t, J = 7.8 Hz), 3.41 (3H, s). |
| 58 | | ¹H-NMR (DMSO-$d_6$) δ: 10.45 (1H, br s), 8.44 (1H, s), 7.91 (1H, s) 7.60 (1H, m), 7.53 (1H, m), 7.28 (1H, m), 7.22 (2H, m), 7.07 (2H, m), 3.34 (3H, s), 2.24 (3H, s) |
| 59 | | ¹H-NMR (DMSO-$d_6$) δ: 9.79 (1H, br s), 7.81 (1H, bs). 7.28 (1H, br s), 7.01-7.00 (4H, m), 6.92-6.91 (2H, m), 6.70 (1H, m), 2.77 (3H, s) |
| 60 | | ¹H-NMR (DMSO-$d_6$) δ: 10.5 (1H, br s), 8.5 (1H, br s) 7.9 (1H, br s), 7.7-7.6 (2H, m), 7.4-7.3 (5H, m), 3.4 (3H, s) |
| 61 | | ¹H-NMR (DMSO-$d_6$) δ: 10.42 (1H, br s), 8.45 (1H, s), 7.92 (1H, s), 7.64-7.62 (2H, m), 7.47-7.45 (2H, m), 7.32 (1H, t, J = 7.8 Hz), 7.24-7.23 (2H, m), 3.37 (3H, s). |
| 62 | | ¹H-NMR (DMSO-$d_6$) δ: 10.45 (1H, br s), 8.45 (1H, s), 7.92 (1H, s), 7.60-7.54 (2H, m), 7.30-7.29 (3H, m), 6.82-6.79 (2H, m), 3.72 (3H, s), 3.34 (3H, s). |
| 63 | | ¹H-NMR (DMSO-$d_6$) δ: 10.52 (1H, s), 10.12 (1H, s) 8.26 (1H, s), 8.10-8.06 (2H, m), 7.92 (1H, s), 7.85 (1H, t, J = 7.1 Hz), 7.56 (1H, t, J = 6.8 Hz), 7.40-7.32 (3H, m) |
| 64 | | ¹H-NMR (DMSO-$d_6$) δ: 10.61 (1H, s), 10.14 (1H, s) 8.78 (1H, s), 8.23 (1H, s), 8.10-8.06 (2H, m), 7.85 (1H, m), 7.70 (1H, m), 7.42-7.32 (3H, m) |
| 65 | | ¹H-NMR (DMSO-$d_6$) δ: 10.61 (1H, s), 10.15 (1H, s), 8.53 (1H, s), 8.11-8.06 (3H, m), 7.88-7.84 (1H, m), 7.64-7.61 (1H, m), 7.42-7.33 (3H, m) |
| 66 | | ¹H-NMR (CDCl$_3$) δ: 8.64 (1H, br s), 8.33 (1H, s), 8.09 (1H, t, J = 7.3 Hz), 8.01-7.87 (3H, m), 7.58-7.55 (2H, m), 7.38 (1H, t, J = 7.8 Hz), 3.56 (3H, s). |
| 67 | | ¹H-NMR (CDCl$_3$) δ: 9.24 (1H, d, J = 2.1 Hz), 8.62-8.60 (1H, m), 8.44 (1H, dd, J = 8.1, 2.0 Hz), 8.37 (1H, d, J = 1.5 Hz), 8.22-8.18 (2H, m), 7.97-7.93 (2H, m), 7.89 (1H, d, J = 8.0 Hz), 7.43 (1H, t, J = 8.0 Hz). |
| 68 | | ¹H-NMR (DMSO-$d_6$) δ: 10.40 (1H, s), 8.25 (1H, s), 7.90 (1H, s), 7.63-7.55 (2H, m), 7.40-7.37 (2H, m), 7.31 (1H, m), 7.09 (2H, t, J = 8.7 Hz), .3.36 (3H, s) |

TABLE 242-continued

| Compound No. | MS | ¹H-NMR |
|---|---|---|
| 69 | | ¹H-NMR (DMSO-d$_6$) δ: 10.67 (1H, s), 8.52 (1H, s), 8.08 (1H, s), 7.68-7.62 (2H, m), 7.40-7.33 (3H, m), 7.08 (2H, m), 3.36(3H, s) |
| 70 | | ¹H-NMR (DMSO-d$_6$) δ: 10.51 (1H, s), 8.76 (1H, s), 8.21 (1H, s) 7.69-7.64 (2H, m), 7.39-7.32 (3H, m), 7.08-7.05(2H, m), 3.36 (3H, s) |
| 71 | | ¹H-NMR (DMSO-d$_6$) δ: 10.50 (1H, s), 10.11 (1H, s), 8.09-8.05 (3H, m), 7.86-7.82 (1H, m), 7.71 (1H, s), 7.56-7.52 (1H, m), 7.39-7.32 (3H, m) |
| 72 | | ¹H-NMR (DMSO-d$_6$) δ: 10.39 (1H, s), 8.04 (1H, m), 7.69(1H, s), 7.62-7.53 (2H, m), 7.39-7.29 (3H, m), 7.07(2H, m), 3.35 (3H, s) |
| 73 | | ¹H-NMR (DMSO-d$_6$) δ: 10.45 (1H, s), 10.12 (1H, s), 8.17 (1H, s), 8.10-8.06 (2H, m), 7.85-7.82 (1H, m), 7.68 (1H, s), 7.58-7.55 (1H, m), 7.39-7.32 (3H, m) |
| 74 | | ¹H-NMR (DMSO-d$_6$) δ: 10.34 (1H, s), 8.16 (1H, s), 7.66(1H, s), 7.62-7.55 (2H, m), 7.39-7.37 (2H, m), 7.31 (1H, m), 7.07 (2H, m), 3.35 (3H, s) |
| 75 | 854 (M + 23) 830 (M − 1). | ¹H-NMR (DMSO-d$_6$) δ: 10.67 (1H, br s), 8.50 (1H, br s), 7.93 (1H, br s), 7.74 (1H, t, J = 7.3 Hz), 7.61-7.56 (3H, m), 7.39 (1H, t, J = 7.6 Hz), 7.23-7.22 (1H, br m), 3.36 (3H, s). |
| 76 | 816 (M − H). | ¹H-NMR (DMSO-d$_6$) δ: 10.77 (1H, br s), 10.51 (1H, br s), 8.52 (1H, br s), 8.26 (1H, d, J = 2.4 Hz), 7.99-7.95 (2H, m), 7.86-7.83 (2H, m), 7.63 (1H, t, J = 6.3 Hz), 7.42 (1H, t, J = 8.1 Hz). |
| 77 | 819 (M + 23) 797 (M + 1) 795 (M − 1) | ¹H-NMR (DMSO-d$_6$) δ: 10.44 (1H, s), 8.46 (1H, s), 7.91 (1H, s), 7.68-7.62 (2H, m), 7.27-7.40 (3H, m), 7.16 (1H, s), 3.36 (3H, s). |
| 78 | 805 (M + 23) 783 (M + 1) 781 (M − 1) | ¹H-NMR (DMSO-d$_6$) δ: 10.55 (1H, s), 10.22 (1H, s), 8.47 (1H, s), 8.04 (1H, ddd, J = 11.5, 7.8, 2.1 Hz), 7.92-7.89 (2H, m), 7.85-7.82 (1H, m), 7.56-7.67 (2H, m), 7.39 (1H, t, J = 8.0 Hz). |
| 79 | 745 (M + 23) 721 (M − 1) | ¹H-NMR (DMSO-d$_6$) δ: 10.59 (2H, s), 9.22-9.22 (1H, m), 8.51 (1H, dd, J = 8.1, 2.3 Hz), 8.46 (1H, s), 8.17 (1H, dd, J = 8.1, 0.8 Hz), 7.92-7.89 (2H, m), 7.66-7.63 (1H, m), 7.41 (1H, t, J = 7.8 Hz) |
| 80 | | ¹H-NMR (DMSO-d$_6$) δ: 9.8 (1H, br s), 9.6 (1H, bs), 7.80 (1H, br s), 7.58 (1H, d, J = 2 Hz), 7.31 (1H, dd, J = 2 Hz, 6 Hz), 7.27 (1H, br s), 7.18 (1H, m), 7.15 (1H, d, J = 6 Hz), 6.97 (1H, m), 6.71 (1H, m) |
| 81 | 780 (M + 1) 778 (M − 1) | ¹H-NMR (CDCl$_3$) δ: 8.33 (1H, s), 8.18 (1H, s), 8.07-8.05 (2H, m), 7.92 (1H, s), 7.84-7.82 (1H, m), 7.51 (1H, t, J = 7.1 Hz), 7.35 (1H, t, J = 7.8 Hz), 6.84 (1H, d, J = 6.8 Hz), 3.53 (3H, s). |
| 82 | 766 (M + 1) 764 (M − 1) | ¹H-NMR (CDCl$_3$) δ: 8.81 (1H, d, J = 2.1 Hz), 8.61 (1H, t, J = 7.3 Hz), 8.40-8.38 (1H, m), 8.36 (1H, s), 8.22 (1H, d, J = 12.2 Hz), 8.06 (1H, s), 7.94-7.92 (2H, m), 7.42 (1H, t, J = 8.0 Hz), 7.13 (1H, dd, J = 8.6, 2.8 Hz). |
| 83 | | ¹H-NMR (CDCl$_3$) δ: 8.33 (1H, s) 7.93 (1H, s), 7.76 (1H, m), 7.65 (1H, m), 7.50 (1H, m), 7.36 (1H, m), 7.22 (2H, m), 6.92 (2H, m) 3.48 (3H, m) |
| 84 | | ¹H-NMR (CDCl$_3$) δ: 10.72 (1H, s), 10.40 (1H, s), 8.51 (1H, s), 8.25-8.19 (1H, m), 8.10-8.06 (2H, m), 8.00-7.93 (2H, m), 7.57-7.46 (1H, m), 7.42-7.38 (2H, m) |
| 85 | | ¹H-NMR (DMSO-d$_6$) δ: 10.58 (1H, s), 10.48 (1H, s), 9.21 (1H, m), 8.51 (1H, m), 8.47 (1H, s), 7.92 (2H, m), 7.86 (1H, m), 7.64 (1H, m), 7.41 (1H, m), 7.02 (1H, t, J = 54.9 Hz). |
| 86 | | ¹H-NMR (DMSO-d$_6$) δ: 10.55 (1H, s), 10.21 (1H, s), 8.47 (1H, s), 8.04 (1H, m), 7.93-7.88 (2H, m), 7.85-7.81 (1H, m), 7.63-7.58 (2H, m), 7.39 (1H, m). |
| 87 | | ¹H-NMR (DMSO-d$_6$) δ: 10.49 (1H, s), 8.59 (1H, s), 8.45 (1H, s) 7.96-7.91 (2H, m), 7.71-7.61(3H, m), 7.35 (1H, m), 6.85 (1H, m, J = 54.7 Hz), 3.40 (3H, s) |
| 88 | | ¹H-NMR (DMSO-d$_6$) δ: 10.39 (1H, s), 8.04 (1H, s), 7.71 (3H, m), 7.66 (1H, m), 7.56 (1H, m), 7.49 (2H, m), 7.31 (1H, m), 3.37 (3H, s) |
| 89 | 679 (M + 1) | ¹H-NMR (DMSO-d$_6$) δ: 8.00 (1H, m), 7.90 (1H, br), 7.79 (1H, m), 7.50 (1H, s), 7.44-7.37 (3H, m), 7.27 (1H, m), 6.92 (2H, m), 6.55 (1H, m), 3.49 (3H, s) |
| 90 | 727 (M + 1) | ¹H-NMR (CDCl$_3$) δ: 8.02-7.99 (2H, m), 7.84 (1H, br), 7.51 (1H, s), 7.44-7.36 (3H, m), 7.28 (1H, m), 6.92 (2H, m), 6.55 (1H, t), 3.49 (3H, s) |
| 91 | 665 (M + 1) | ¹H-NMR (CDCl$_3$) δ: 8.64 (1H, m), 8.04-8.01 (2H, m), 7.94 (2H, m), 7.86 (1H, m), 7.81 (1H, d), 7.52 (1H, s), 7.38 (1H, m), 7.22 (2H, m), 6.61 (1H, t) |
| 92 | 713 (M + 1) | ¹H-NMR (CDCl$_3$) δ: 8.64 (1H, m), 8.05-7.92 (5H, m), 7.86 (1H, m), 7.53 (1H, s), 7.38 (1H, m), 7.22 (2H, m), 6.58 (1H, t) |
| 93 | 731 (M + 1) | ¹H-NMR (CDCl$_3$) δ: 8.12 (1H, s), 8.05-8.00 (2H, m), 7.89 (1H, s), 7.44 (1H, m), 7.35 (2H, m), 7.30 (1H, m), 6.91 (2H, m), 3.50 (3H, s) |
| 94 | 747 (M + 1) | ¹H-NMR (CDCl$_3$) δ: 8.03 (1H, m), 7.91-7.85 (2H, m), 7.44 (1H, d), 7.36 (2H, m), 7.30 (1H, m), 6.91 (2H, d), 3.49 (3H, s) |

TABLE 242-continued

| Compound No. | MS | ¹H-NMR |
|---|---|---|
| 95 | 733 (M + 1) | ¹H-NMR (CDCl₃) δ: 8.65 (1H, m), 8.03-8.00 (2H, m), 7.94 (2H, m), 7.87 (2H, m), 7.58 (1H, m), 7.39 (1H, m), 7.22 (2H, m) |
| 96 | 763 (M + 1) | ¹H-NMR (DMSO-d₆) δ: 10.4 (1H, s), 8.2 (1H, s), 7.7-7.6 (3H, m), 7.4-7.1 (4H, m), 3.4 (3H, s) |
| 97 | 749 (M + 1) | ¹H-NMR (DMSO-d₆)δ: 10.7 (2H, s), 8.8 (1H, s) 8.1-8.0 (1H, s), 7.9-7.9 (1H, m), 7.8-7.8 (1H, m), 7.8 (1H, s), 7.7-7.6 (1H, m), 7.6-7.6 (1H, m), 7.4 (1H, t, J = 7.8 Hz) |
| 98 | 748 (M + 1) | ¹H-NMR (DMSO-d₆) δ: 10.4 (1H, m), 8.7 (1H, s), 8.0-8.0 (2H, m), 7.8-7.8 (1H, m), 7.7 (1H, m), 7.7 (1H, m), 7.6-7.6 (1H, m), 7.4 (1H, m), 3.4 (3H, s) |
| 99 | 734 (M + 1) | ¹H-NMR (DMSO-d₆) δ: 10.8 (1H, s), 10.8 (1H, s), 9.3-9.3 (1H, m), 8.6-8.6 (1H, m), 8.1-8.1(2H, m) 7.9-7.9 (1H, m) 7.8 (1H, s), .7.6-7.5 (1H, m), 7.4(1H, t, J = 8.0 Hz) |
| 100 | 715 (M + 1) | ¹H-NMR (DMSO-d₆) δ: 10.4 (1H, s), 8.0 (1H, s), 7.7-7.6 (2H, m), 7.6-7.5 (1H, m), 7.4-7.3 (3H, m) 7.2 (1H, s) 3.4 (3H, s) |
| 101 | 701 (M + 1) | ¹H-NMR (DMSO-d₆) δ: 10.8 (1H, s), 10.4 (1H, s), 8.1-8.1 (1H, m), 8.1-8.0 (1H, m), 7.9-7.9 (1H, m) 7.8-7.8 (2H, m). 7.7-7.6 (1H, m), 7.6-7.5 (1H, m), 7.4 (1H, t, J = 7.8 Hz) |
| 102 | 816 (M + 1) | ¹H-NMR (DMSO-d₆) δ: 10.78 (1H, s), 10.76 (1H, s), 9.29 (1H, d, J = 1.8 Hz), 8.61 (1H, dd, J = 7.8, 1.8 Hz), 8.52 (1H, s), 8.13 (1H, d, J = 7.8 Hz), 7.96-7.91 (2H, m), 7.66-7.62 (1H, m), 7.45 (1H, t, J = 8.0 Hz) |
| 103 | 777 (M + 1) | ¹H-NMR (DMSO-d₆) δ: 10.08 (1H, s), 7.99 (1H, s), 7.60-7.55 (2H, m), 7.50 (1H, s), 7.40-7.37 (2H, m), 7.31-7.25 (1H, m), 7.18(1H, t, J = 73.1 Hz), 7.11-7.04 (2H, m), 3.35 (3H, s) |
| 104 | 763 (M + 1) | ¹H-NMR (DMSO-d₆) δ: 10.39 (1H, s), 10.30 (1H, s), 8.08 (2H, dd, J = 8.5, 5.7 Hz), 8.01 (1H, s), 7.82-7.78 (1H, m), 7.60-7.56 (1H, m), 7.52 (1H, s), 7.40-7.35 (3H, m), 7.30 (1H, t, J = 72.9 Hz) |
| 105 | 729 (M + 1) | ¹H-NMR (DMSO-d₆) δ: 10.15 (1H, s), 7.85 (1H, s), 7.62-7.54 (2H, m), 7.54-7.50 (1H, m), 7.41-7.35 (2H, m), 7.32-7.25 (1H, m), 7.23 (1H, t, J = 72.8 Hz), 7.11-7.02 (2H, m), 3.34(3H, s) |
| 106 | 715 (M + 1) | ¹H-NMR (DMSO-d₆) δ: 10.47 (1H, s), 10.31 (1H, s), 8.09 (2H, m) 7.92 (1H, s), 7.83-7.79 (1H, m), 7.59-7.17 (6H, m) |
| 107 | | ¹H-NMR (DMSO-d₆) δ: 10.17 (1H, s), 8.68 (1H, s), 8.03-7.99 (2H, m), 7.82 (1H, m), 7.71 (1H, m), 7.62 (1H, m), 7.50 (1H, s), 7.35 (1H, m), 7.18 (1H, m), 3.41 (3H, s). |
| 108 | | ¹H-NMR (DMSO-d₆) δ: 10.56 (1H, s), 10.23 (1H, s), 9.27 (1H, m), 8.59 (1H, m), 8.08 (1H, m), 8.01(1H, m), 7.93-7.90(2H, m), 7.62(1H, m), 7.52 (1H, s), 7.41 (1H, m), 7.24 (1H, t, J = 73.2 Hz) |
| 109 | | ¹H-NMR (DMSO-d₆) δ10.13 (1H, s), 8.00 (1H, m), 7.66-7.60 (2H, m), 7.51 (1H, s), 7.38-7.30 (3H, m), 7.19 (1H, t, J = 73 Hz), 7.17 (1H, m), 3.35 (3H, s) |
| 110 | | ¹H-NMR (DMSO-d₆) δ: 10.21 (2H, s), 8.05-8.01 (2H, m), 7.91-7.88 (1H, m), 7.84-7.80 (1H, m), 7.62-7.56 (2H, m), 7.52 (1H, s), 7.40-7.38 (1H, m), 7.23 (1H, t, J = 68.3 Hz) |
| 111 | 870 (M + 23) | ¹H-NMR (CDCl₃) δ: 8.38-8.36 (2H, m), 8.17-8.16 (1H, m), 8.06-8.05 (2H, m), 7.96 (1H, s), 7.92 (1H, d, J = 8.3 Hz), 7.73 (1H, d, J = 8.0 Hz), 7.66-7.64 (0.5H, m), 7.49-7.45 (2H, m), 7.29 (1H, t, J = 7.8 Hz), 3.57 (3H, s), 3.24 (1H, s). |
| 112 | 855 (M + 23) | ¹H-NMR (CDCl₃) δ: 8.61 (1H, td, J = 7.9, 1.6 Hz), 8.37 (1H, s), 8.30 (1H, d, J = 8.0 Hz), 8.15 (1H, d, J = 12.2 Hz), 8.05 (1H, d, J = 8.0 Hz), 7.97 (1H, td, J = 8.1, 1.7 Hz), 7.95 (1H, s), 7.81 (1H, s), 7.44 (1H, t, J = 8.1 Hz). |
| 113 | 803 (M + 23) | ¹H-NMR (CDCl₃) δ: 8.83 (2H, s), 8.33 (1H, s), 8.14-8.11 (1H, m), 8.01 (1H, d, J = 11.9 Hz), 7.93 (1H, s), 7.59 (1H, t, J = 7.8 Hz), 7.43 (1H, t, J = 7.8 Hz), 3.58 (3H, s). |
| 114 | 789 (M + 23) | ¹H-NMR (CDC₁₃) δ: 9.41 (2H, s), 8.60 (1H, t, J = 7.0 Hz), 8.37 (1H, s), 8.16 (1H, d, J = 12.5 Hz), 8.08 (1H, s), 8.01-7.98 (1H, m), 7.96 (1H, s), 7.47-7.45 (1H, m). |
| 115 | 752 (M + 23) | 1H-NMR (CDCl₃) δ: 8.34 (1H, s), 8.18 (1H, s), 8.09-8.00 (2H, m), 7.93 (1H, s), 7.83 (1H, s), 7.51 (1H, s), 7.36 (1H, t, J = 7.2 Hz), 6.84 (1H, s), 3.53 (3H, s). |
| 116 | 738 (M + 23) | 1H-NMR (CDCl3) δ: 8.81 (1H, d, J = 2.4 Hz), 8.62 (1H, t, J = 7.0 Hz), 8.41-8.37 (2H, m), 8.21-8.19 (1H, m), 8.05 (1H, s), 7.96-7.93 (2H, m), 7.42 (1H, t, J = 8.1 Hz), 7.13 (1H, dd, J = 8.6, 2.8 Hz). |
| 117 | | ¹H-NMR (DMSO-d₆) δ: 10.39 (1H, s), 8.67(1H, s), 8.16 (1H, m), 8.02 (1H, m), 7.81 (1H, m), 7.74(1H, m), 7.66 (1H, s), 7.61(1H, m), 7.36(1H, m), 3.41 (3H, s). |
| 118 | | ¹H-NMR (DMSO-d₆) δ: 10.53 (2H, m), 9.26 (1H, m), 8.59 (1H, m), 8.18 (1H, m), 8.07 (1H, m) 7.93 (1H, m) 7.69 (1H, s), 7.59 (1H, m), 7.42 (1H, m) |

TABLE 242-continued

| Compound No. | MS | $^1$H-NMR |
|---|---|---|
| 119 | | $^1$H-NMR (DMSO-$d_6$) δ: 10.45 (1H, s), 8.67 (1H, s), 8.45 (1H, s), 8.02 (1H, m), 7.90 (1H, s), 7.81 (1H, m), 7.75 (1H, m), 7.66 (1H, m), 7.37 (1H, m), 3.11 (3H, s) |

Compound (B) disclosed in WO 2010/018857, fluralaner and afoxolaner were used as comparative compounds in following test examples.

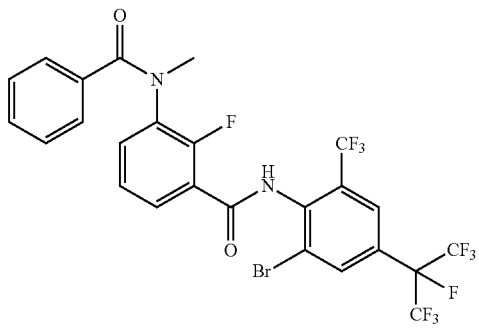

(B)

Test Example A

In Vitro Contact Tests with Fleas

In vitro contact tests with fleas were conducted with adult male and female cat fleas (*Ctenocephalides felis*).

To coat the test tubes, the test substance was dissolved and diluted in acetone p.a. to the desired concentration. The solution was then homogeneously applied to the inner wall and base of a glass tube by turning and rocking on an orbital shaker until complete evaporation of the solvent. For example, with a 900 ppm solution of test substance, an area-based dose of 5 μg/cm² was achieved.

Upon complete evaporation of the solvent, 5-10 adult cat fleas (*Ctenocephalides felis*) were added to each coated tube, which was then sealed with a perforated plastic lid and incubated in a horizontal position at room temperature and ambient humidity. After 48 h, insecticidal activity against fleas was determined. For this, fleas were collected to the base of the tube by knocking the tube, and the tube was allowed to stand upright. Fleas which remained motionless at the base or moved in an uncoordinated manner were considered dead or moribund, respectively.

A substance was judged to have good insecticidal activity against *Ctenocephalides felis* when at least 80% of the fleas were found dead or moribund at a dose of the substance of 5 μg/cm². 100% insecticidal activity means that all the fleas were found dead or moribund. 0% insecticidal activity means that no fleas were found dead or moribund.

In this test, for example, the following compounds from the preparation examples exhibited an insecticidal activity of 95% at a dose of 1 μg/cm²: Compounds 24, 26, 3, 4, 5, 6, 7, 8, 9, 10, 11, 12, 14, 15, 16, 19, 20, 21, 29, 33, 38, 39, 23, 37, 44, 46, 47, 48, 49, 51, 52, 53, 54, 55, 56, 57, 58, 59, 60, 61, 62, 17, 35, 34, 79, 66, 67, 81, 82, 75, 77, 78, 74, 73, 72, 71, 70, 64, 69, 65, 68, 63, 83, 85, 86, 87, 13, 88, 89, 90, 91, 92, 93, 36, 95, 97, 96, 101, 100, 98, 102, 104, 103, 106, 105, 107, 108, 109, 110, 111, 115, 116, 117, 118, and 119.

In this test, for example, the following compounds from the preparation examples exhibited an insecticidal activity of 95% at a dose of 0.2 μg/cm²: Compounds 24, 26, 3, 4, 5, 6, 8, 9, 10, 11, 12, 14, 15, 16, 19, 20, 21, 29, 33, 38, 23, 37, 44, 47, 49, 51, 53, 54, 55, 56, 57, 58, 59, 60, 61, 62, 17, 35, 34, 79, 66, 67, 81, 82, 75, 77, 78, 74, 73, 72, 71, 70, 64, 69, 65, 68, 83, 85, 86, 87, 13, 88, 89, 90, 91, 92, 93, 36, 95, 97, 96, 101, 100, 98, 102, 104, 103, 106, 105, 107, 108, 109, 110, 111, 115, 116, 117, 118, and 119.

In this test, for example, the following compounds from the preparation examples exhibited an insecticidal activity of 95% at a dose of 0.04 μg/cm²: Compounds 24, 26, 16, 21, 23, 37, 49, 51, 53, 54, 56, 57, 58, 17, 67, 81, 82, 74, 73, 83, 85, 86, 87, 89, 90, 91, 92, 93, 36, 97, 96, 101, 100, 104, 103, 106, 105, 107, 109, 111, 115, 116, and 119.

Test Example B

In Vitro Contact Tests with Adult Hard Ticks

In vitro contact tests with ticks were conducted with adult males and females of *Rhipicephalus sanguineus, Ixodes ricinus,* or *Dermacentor variabilis*, or nymphs of *Amblyomma americanum*.

For the coating of the test vials, the test substance was dissolved and diluted in acetone p.a. to the desired concentration. The solution was then homogeneously applied to the inner wall and base of a glass vial by turning and rocking on an orbital shaker until complete evaporation of the solvent. For example, with a 900 ppm solution of test substance, an area-based dose of 5 μg/cm² was achieved.

After the solvent was completely evaporated, 5-10 adult ticks were put in each coated test vial, which was then sealed with a perforated plastic lid and incubated in a horizontal position in the dark at room temperature and ambient humidity (*Rhipicephalus sanguineus*) or in a climate-controlled cabinet (*Ixodes ricinus, Dermacentor variabilis, Amblyomma americanum* [21° C., 85% rel. hum.]). Acaricidal activity against the respective tick species was determined after 48 h. For this, ticks were collected to the base of the test vial by gentle knocking, and test vials were then incubated on a hotplate at 45-50° C. for no longer than 5 min. Ticks which remained motionless on the base of the test vial or moved uncoordinated without deliberately climbing up to avoid the heat were considered dead or moribund, respectively.

A substance was judged to have good acaricidal activity against the respective tick species when at least 80% of ticks were found dead or moribund at a dose of the substance of 5 μg/cm². An acaricidal activity of 100% means all ticks were dead or moribund. An acaricidal activity of 0% means none of the ticks was found dead or moribund.

In this test, for example, the following compounds from the preparation examples exhibited an acaricidal activity of 90% at a dose of 1 μg/cm² against *Amblyomma americanum*: Compounds 24, 26, 1, 2, 3, 4, 9, 11, 12, 15, 16, 19, 21, 29, 33, 38, 39, 23, 37, 46, 51, 56, 57, 58, 59, 60, 62, 35, 34, 79, 67, 81, 82, 75, 76, 77, 78, 74, 73, 71, 64, 69, 65, 84, 85, 86, 87, 13, 89, 91, 92, 93, 94, 36, 95, 97, 96, 101, 100, 102, 104, 103, 106, 105, 108, 109, 110, 115, 116, 117, 118, and 119.

In this test, for example, the following compounds from the preparation examples exhibited an acaricidal activity of 90% at a dose of 0.2 µg/cm² against *Amblyomma americanum*: Compounds 24 and 26, and Compounds 11, 12, 15, 16, 21, 29, 33, 38, 39, 37, 46, 56, 58, 60, 35, 34, 79, 67, 81, 82, 78, 74, 73, 71, 64, 69, 65, 84, 85, 86, 87, 13, 91, 92, 94, 36, 95, 97, 96, 101, 100, 102, 104, 103, 106, 108, 110, 115, 116, and 118.

In this test, for example, the following compounds from the preparation examples exhibited an acaricidal activity of 90% at a dose of 0.04 µg/cm² against *Amblyomma americanum*: Compounds 12, 56, 35, 86, 91, 95, 104, 106, 105, and 110.

In this test, for example, the following compounds from the preparation examples exhibited an acaricidal activity of 90% at a dose of 1 µg/cm² against *Dermacentor variabilis*: Compounds 26, 5, 9, 16, 21, 29, 33, 38, 23, 37, 44, 51, 53, 54, 56, 57, 60, 62, 17, 35, 34, 80, 79, 66, 67, 81, 82, 76, 77, 78, 74, 73, 72, 71, 64, 68, 63, 84, 85, 86, 87, 13, 88, 89, 90, 91, 93, 94, 36, 95, 97, 96, 101, 99, 100, 98, 102, 104, 103, 106, 105, 107, 108, 109, 110, 115, and 119.

In this test, for example, the following compounds from the preparation examples exhibited an acaricidal activity of 90% at a dose of 0.2 µg/cm² against *Dermacentor variabilis*: Compounds 26, 9, 16, 21, 29, 33, 23, 37, 44, 51, 53, 54, 56, 57, 17, 35, 34, 80, 67, 81, 82, 76, 77, 78, 74, 73, 72, 71, 64, 63, 84, 85, 86, 87, 13, 88, 89, 90, 91, 92, 93, 36, 97, 96, 101, 99, 100, 98, 104, 103, 106, 105, 107, 108, 109, 110, 115, and 119.

In this test, for example, the following compounds from the preparation examples exhibited an acaricidal activity of 90% at a dose of 0.04 µg/cm² against *Dermacentor variabilis*: Compounds 23, 34, 81, 82, 78, 73, 85, 86, 91, 92, 97, 104, 103, and 106.

In this test, for example, the following compounds from the preparation examples show an acaricidal activity of 90% at a dose of 5 µg/cm² against *Ixodes ricinus*: Compounds 24, 26, 9, 12, 16, 29, 35, 34, 80, 79, 67, 81, 82, 78, 74, 73, 72, 71, 64, 65, 68, 63, 84, 85, 86, 13, 89, 90, 91, 92, 93, 36, 95, 97, 101, 102, 104, 103, 106, 105, 108, 109, 110, 115, and 118.

In this test, for example, the following compounds from the preparation examples exhibited an acaricidal activity of 90% at a dose of 1 µg/cm² against *Ixodes ricinus*: Compounds 24, 26, 9, 12, 16, 35, 34, 79, 67, 78, 74, 73, 72, 71, 64, 65, 68, 63, 84, 85, 86, 13, 89, 90, 91, 92, 36, 95, 97, 96, 101, 99, 104, 106, 105, 108, 109, 110, 116, and 118.

In this test, for example, the following compounds from the preparation examples exhibited an acaricidal activity of 90% at a dose of 0.2 µg/cm² against *Ixodes ricinus*: Compounds 24, 9, 12, 16, 35, 67, 78, 73, 72, 71, 63, 84, 85, 86, 13, 89, 91, 92, 36, 95, 97, 101, 104, 103, 106, 108, 109, 110, 116, and 118.

In this test, for example, the following compounds from the preparation examples exhibited an acaricidal activity of 90% at a dose of 1 µg/cm² against *Rhipicephalus sanguineus*: Compounds 24, 26, 3, 10, 11, 12, 14, 15, 16, 19, 21, 29, 39, 23, 37, 44, 51, 54, 57, 58, 59, 60, 62, 17, 35, 34, 80, 79, 66, 67, 81, 82, 75, 76, 77, 78, 74, 73, 72, 71, 70, 64, 69, 65, 68, 63, 84, 85, 86, 13, 88, 89, 90, 91, 92, 94, 36, 95, 97, 96, 101, 99, 100, 102, 104, 103, 106, 105, 108, 110, 115, 116, 117, and 118.

In this test, for example, the following compounds from the preparation examples exhibited an acaricidal activity of 90% at a dose of 0.2 µg/cm² against *Rhipicephalus sanguineus*: Compounds 3, 9, 11, 12, 14, 15, 16, 19, 21, 29, 37, 44, 51, 54, 57, 59, 60, 17, 35, 34, 79, 66, 67, 81, 82, 75, 76, 78, 74, 73, 72, 71, 70, 64, 69, 65, 68, 63, 84, 85, 86, 13, 88, 89, 90, 91, 92, 94, 36, 95, 97, 101, 99, 102, 104, 103, 106, 107, 108, 110, 115, 117, and 118.

In this test, for example, the following compounds from the preparation examples show an acaricidal activity of 90% at a dose of 0.04 µg/cm² against *Rhipicephalus sanguineus*: Compounds 11, 12, 16, 21, 29, 17, 35, 67, 82, 76, 74, 73, 72, 71, 68, 84, 86, 13, 91, 92, 36, 95, 104, 106, 108, 109, and 115.

Test Example C

In Vitro Injection Test with *Rhipicephalus* (*Boophilus*) *microplus* (BOOPMI Inj)

To produce an appropriate mixture for injection, the test substance was dissolved and diluted in dimethyl sulphoxide to the desired concentration. 1 µl of the test mixture was injected into the abdomen of each of 5 engorged adult female cattle ticks (*Rhipicephalus* (*Boophilus*) *microplus*). The ticks were transferred into petri dishes and maintained in a climate-controlled room [28° C., 85% rel. hum.].

Acaricidal activity against cattle ticks was assessed after 7 days by assessment of laid fertile eggs. Eggs which did not appear normal were stored in a climate-controlled cabinet [28° C., 85% rel h.] until larval hatch after 42 days. An acaricidal activity of 100% means that none of the ticks laid eggs or laid eggs were infertile; 0% means that the ticks laid eggs, and all the eggs were fertile.

In this test, for example, the following compounds from the preparation examples exhibited an acaricidal activity of 100% at a dose of 0.8 µg/animal: Compounds 24, 26, 1, 2, 3, 4, 5,6,7,9, 10, 11, 12, 14, 15, 16, 19, 20, 21, 32, 33, 38, 39, 40, 42, 23, 37, 44, 45, 46, 47, 48, 49, 51, 52, 53, 54, 56, 57, 58, 59, 60, 61, 62, 17, 35, 34, 80, 79, 66, 67, 81, 82, 75, 76, 77, 78, 74, 73, 72, 71, 70, 64, 69, 65, 68, 63, 83, 84, 85, 86, 87, 13, 88, 89, 90, 91, 92, 93, 94, 36, 95, 97, 96, 101, 99, 100, 98, 102, 104, 103, 106, 105, 107, 108, 109, 110, 111, 112, 113, 114, 115, 116, 117, 118, and 119.

In this test, for example, the following compounds from the preparation examples exhibited an acaricidal activity of 100% at a dose of 0.16 µg/animal: Compounds 24, 26, 5, 9, 10, 11, 12, 14, 15, 16, 19, 20, 21, 33, 38, 39, 42, 23, 37, 44, 45, 48, 49, 51, 53, 54, 56, 57, 58, 59, 60, 61, 62, 17, 35, 34, 79, 66, 67, 81, 82, 75, 76, 77, 78, 74, 73, 72, 71, 70, 64, 69, 65, 68, 63, 83, 84, 85, 86, 87, 13, 88, 89, 90, 91, 92, 93, 94, 36, 95, 97, 96, 101, 99, 100, 98, 102, 104, 103, 106, 105, 107, 108, 109, 110, 111, 113, 115, 116, 117, 118, and 119.

In this test, for example, the following compounds from the preparation examples exhibited an acaricidal activity of 100% at a dose of 0.032 µg/animal: Compounds 24, 26, 20, 21, 23, 37, 51, 54, 56, 57, 58, 59, 60, 17, 35, 34, 79, 81, 82, 77, 78, 74, 73, 72, 71, 70, 64, 84, 85, 86, 87, 13, 88, 89, 90, 91, 92, 93, 94, 36, 95, 96, 102, 104, 103, 106, 105, 107, 108, 109, 110, 113, 115, 116, 117, 118, and 119.

In this test, for example, the following compounds from the preparation examples exhibited an acaricidal activity of 100% at a dose of 0.0064 µg/animal: Compounds 23, 37, 35, 34, 81, 82, 89, 90, 92, 94, 104, 103, 106, and 109.

Test Example D

Ctenocephalides felis In-Vitro Feeding Test with Fleas (CTECFE Oral)

To prepare a test blood mixture for feeding fleas, the test substance was dissolved in dimethyl sulphoxide and diluted with citrated cattle blood to the desired concentration.

To assemble the test set-up, about 20 unfed adult male and female cat fleas (Ctenocephalides felis) were placed in a chamber which was closed at the top and bottom with gauze. A metal cylinder was sealed at one end with parafilm membrane, placed with the sealed base onto the chamber, and filled with the test blood mixture, which could be imbibed by the fleas through the parafilm membrane. The assembled test set-up was maintained at about 37° C. After 48 hours, the insecticidal feeding activity against fleas was determined. 100% means that all of the fleas were killed; 0% means that none of the fleas was killed.

In this test, for example, the following compounds from the preparation examples exhibited an insecticidal feeding activity of 95% at a dose of 4 ppm: Compounds 24, 26, 3, 5, 6,7, 8,9, 10, 11, 12, 14, 15, 16, 19, 20, 21, 29, 32, 33, 38, 39, 40, 42, 18, 23, 37, 44, 45, 46, 47, 48, 49, 50, 51, 52, 53, 54, 55, 56, 57, 58, 59, 60, 61, 62, 17, 35, 34, 80, 79, 66, 67, 81, 82, 75, 76, 77, 78, 74, 73, 72, 71, 70, 64, 69, 65, 68, 63, 83, 84, 85, 86, 87, 13, 88, 89, 90, 91, 92, 93, 94, 36, 95, 97, 96, 101, 99, 100, 98, 102, 104, 103, 106, 105, 107, 108, 109, 110, 111, 112, 113, 114, 115, 116, 117, 118, and 119.

In this test, for example, the following compounds from the preparation examples exhibited an insecticidal feeding activity of 95% at a dose of 0.8 ppm: Compounds 24, 26, 6, 8,9, 11, 12, 14, 16, 19, 20, 21, 29, 33, 38, 39, 40, 42, 18, 23, 37, 44, 45, 46, 48, 49, 51, 53, 54, 56, 57, 58, 59, 60, 61, 62, 17, 35, 34, 80, 79, 66, 67, 81, 82, 75, 76, 77, 78, 74, 73, 72, 71, 70, 64, 69, 65, 68, 63, 83, 84, 85, 86, 87, 13, 88, 89, 90, 91, 92, 93, 94, 36, 95, 97, 96, 101, 99, 100, 98, 102, 104, 103, 106, 105, 107, 108, 109, 110, 111, 112, 113, 114, 115, 116, 117, 118, and 119.

In this test, for example, the following compounds from the preparation examples exhibited an insecticidal feeding activity of 95% at a dose of 0.16 ppm: Compounds 11, 14, 16, 33, 38, 23, 37, 44, 45, 46, 48, 49, 51, 53, 54, 56, 57, 59, 60, 62, 17, 35, 34, 80, 79, 66, 67, 81, 82, 77, 78, 74, 73, 70, 64, 69, 65, 68, 63, 83, 84, 85, 86, 87, 13, 88, 89, 90, 91, 92, 93, 94, 36, 95, 97, 96, 101, 99, 100, 102, 104, 103, 106, 105, 107, 108, 109, 110, 111, 112, 113, 114, 115, 116, 117, 118, and 119.

In this test, for example, the following compounds from the preparation examples exhibited an insecticidal feeding activity of 95% at a dose of 0.032 ppm: Compounds 16, 23, 37, 49, 51, 53, 54, 17, 35, 34, 80, 74, 70, 69, 65, 68, 63, 83, 85, 86, 87, 13, 88, 89, 90, 91, 92, 93, 94, 102, 104, 103, 106, 105, 107, 108, 109, 110, 111, 113, 115, 116, 117, 118, and 119.

In this test, for example, the following compounds from the preparation examples exhibited an insecticidal feeding activity of 95% at a dose of 0.0064 ppm: Compounds 16, 23, 49, 51, 53, 17, 34, 85, 36, 103, 106, 108, 111, 115, and 116.

Test Example E

Topical Treatment In-Vivo Test with American Dog Tick Nymph and Cat Flea on Rats Type of study and overall study design: The method is a randomized non-blinded efficacy study in accordance with European animal welfare requirements. Rats (Rattus norvegicus) were randomized based on pre-treatment flea counts. The efficacy of treatment was determined by comparison of the flea and tick counts of different treatment groups versus the placebo-treated control group. The experimental unit was the individual study animal.

Method and route of administration: The compound was applied in a suitable solvent and carrier (more specifically, added to the following mixture: 33.3% by weight propylene carbonate, 67.7% by weight N-methylpyrrolidone, 0.1% by weight BHA, 0.05% by weight BHT) considering the individual body weight as topical spot-on between the shoulder blades directly onto the skin.

Experimental infestation: On the day of treatment and weekly thereafter, 30 ticks (D. variabilis nymphs) were released onto the back of each rat, and 30 fleas (C. felis) were released onto the back of each rat 24h later.

Tick and Flea counting: Rats were thoroughly examined and ticks and fleas were manually removed 48h (±4h) after tick infestation and 24h after flea infestation. Live fleas and live attached engorged ticks were counted. In non-evident cases, engorgement status was evaluated by squeezing the tick on a filter paper to find traces of blood as sign for engorgement.

TABLE 247

Geometric mean percent reduction in live tick (Dermacentor variabilis) counts compared to untreated control rats

| | Effective dose | SD 2 | SD 9 | SD 16 | SD 23 | SD 30 |
|---|---|---|---|---|---|---|
| Compound (B) | 25 mg/kg | 58 | 85 | 65 | 4 | |
| Compound 51 | 25 mg/kg | 82 | 95 | 80 | 73 | 55 |
| Compound 67 | 25 mg/kg | 57 | 98 | 100 | 100 | 77 |

SD = study day

TABLE 248

Geometric mean percent reduction in live flea (Ctenocephalides felis) counts compared to untreated control rats

| | Effective dose | SD 2 | SD 9 | SD 16 | SD 23 | SD 30 |
|---|---|---|---|---|---|---|
| Afoxolaner | 10 mg/kg | 100 | 99 | 51 | 16 | |
| Compound (B) | 25 mg/kg | 84 | 72 | 45 | | |
| Compound 24 | 10 mg/kg | 100 | 99 | 97 | 96 | 77 |
| Compound 51 | 25 mg/kg | 100 | 98 | 91 | 95 | 93 |
| Compound 67 | 25 mg/kg | 98 | 93 | 97 | 81 | 79 |

SD = study day

Test Example F

Systemic Treatment In-Vivo Test with American Dog Tick Nymph and Cat Flea on Rats Type of study and overall study design: The method is a randomized non-blinded efficacy study in accordance with European animal welfare requirements. Rats (Rattus norvegicus) were randomized based on pre-treatment flea counts. The efficacy of treatment was determined by comparison of the flea and tick counts of different treatment groups versus the placebo-treated control group. The experimental unit was the individual study animal. Method and route of administration: The compound was applied in a suitable solvent and carrier (more specifically, added to glycerol formal; in case of poorly soluble compounds, a solvent mixture with up to 25% by volume of N-methyl pyrrolidone may be used.) considering the individual body weight as an intraperitoneal injection.

Experimental infestation: On the day of treatment and weekly thereafter, 30 ticks (*D. variabilis* nymphs) were released onto the back of each rat, and 30 fleas (*C. felis*) were released onto the back of each rat 24h later.

Tick and Flea counting: Rats were thoroughly examined and ticks and fleas were manually removed 48h (±4h) after tick infestation and 24h after flea infestation. Live fleas and live attached engorged ticks were counted. In non-evident cases, engorgement status was evaluated by squeezing the tick on a filter paper to find traces of blood as sign for engorgement.

TABLE 249

Geometric mean percent reduction in live tick (*Dermacentor variabilis*) counts compared to untreated control rats

|  | Effective dose | SD 2 | SD 9 | SD 16 | SD 23 | SD 30 |
|---|---|---|---|---|---|---|
| Afoxolaner | 2 mg/kg | 86 | 53 | 5 | | |
| Afoxolaner | 10 mg/kg | 100 | 10 | 78 | 0 | |
| Compound (B) | 2 mg/kg | 75 | 63 | 0 | | |
| Compound (B) | 10 mg/kg | 100 | 11 | 2 | | |
| Compound 37 | 10 mg/kg | 100 | 100 | 99 | 99 | 80 |
| Compound 66 | 10 mg/kg | 100 | 100 | 100 | 100 | 95 |
| Compound 67 | 2 mg/kg | 100 | 95 | 32 | 20 | |
| Compound 67 | 10 mg/kg | 100 | 100 | 99 | 75 | 57 |
| Compound 74 | 10 mg/kg | 100 | 100 | 90 | 89 | 78 |
| Compound 90 | 2 mg/kg | 100 | 83 | 29 | | |
| Compound 103 | 10 mg/kg | 100 | 100 | 74 | 43 | |
| Compound 115 | 10 mg/kg | 100 | 99 | 86 | 46 | 17 |
| Compound 119 | 2 mg/kg | 100 | 96 | 63 | 1 | 61 |
| Compound 119 | 10 mg/kg | 100 | 100 | 100 | 89 | 61 |

SD = study day

TABLE 250

Geometric mean percent reduction in live flea (*Ctenocephalides felis*) counts compared to untreated control rats

|  | Effective dose | SD 2 | SD 9 | SD 16 | SD 23 | SD 30 |
|---|---|---|---|---|---|---|
| Fluralaner | 5 mg/kg | 100 | 100 | 51 | 7 | |
| Afoxolaner | 2 mg/kg | 69 | 20 | 48 | | |
| Afoxolaner | 10 mg/kg | 100 | 97 | 60 | 0 | |
| Compound (B) | 2 mg/kg | 97 | 32 | | | |
| Compound (B) | 10 mg/kg | 100 | 53 | 6 | | |
| Compound 24 | 5 mg/kg | 100 | 99 | 99 | 36 | |
| Compound 43 | 5 mg/kg | 100 | 99 | 90 | 91 | 13 |
| Compound 37 | 10 mg/kg | 100 | 97 | 97 | 100 | 80 |
| Compound 51 | 2 mg/kg | 100 | 96 | 67 | 37 | |
| Compound 51 | 10 mg/kg | 100 | 100 | 98 | 90 | 90 |
| Compound 66 | 10 mg/kg | 100 | 100 | 100 | 100 | 79 |
| Compound 67 | 2 mg/kg | 100 | 96 | 78 | 11 | |
| Compound 67 | 10 mg/kg | 100 | 100 | 93 | 61 | 58 |
| Compound 74 | 10 mg/kg | 91 | 96 | 86 | 89 | 78 |
| Compound 70 | 10 mg/kg | 99 | 100 | 99 | 49 | 7 |
| Compound 93 | 10 mg/kg | 100 | 97 | 68 | 14 | |
| Compound 96 | 10 mg/kg | 99 | 97 | 96 | 46 | 25 |
| Compound 103 | 10 mg/kg | 100 | 92 | 70 | 20 | |
| Compound 115 | 2 mg/kg | 100 | 98 | 73 | | |
| Compound 115 | 10 mg/kg | 100 | 100 | 99 | 47 | 8 |
| Compound 119 | 10 mg/kg | 100 | 97 | 94 | 62 | 44 |

SD = study day

Test Example G

Insecticidal Testing against Common Cutworm (*Spodoptera litura*)

Cabbage leaves were immersed in a liquid containing the testing compound at a predetermined concentration for 30 seconds and air-dried. The leaves were placed in a 7-cm polyethylene cup, and the second-stage larvae of common cutworm were left therein. The cup was placed in a constant-temperature room at 25° C., and the survival rate was investigated after 6 days. The test was carried out with two groups of 5 larvae per group. As a result, Compound Nos. 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, and 119 exhibited an pesticidal rate of 70% or more at a concentration of 100 ppm.

Test Example H

Insecticidal Testing against Diamondback Moth (*Plutella xylostella*)

Cabbage leaves were immersed in a liquid containing the testing compound at a predetermined concentration for 30 seconds and air-dried. They were placed in a 7-cm polyethylene cup, and the third-stage larvae of diamondback moth were left therein. The cup was placed in a constant-temperature room at 25° C., and the survival rate was investigated after 6 days. The test was carried out with two groups of 5 larvae per group. As a result, Compound Nos. 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, and 119 exhibited an pesticidal rate of 70% or more at a concentration of 100 ppm.

Test Example I

Insecticidal Testing against Small Brown Planthopper (*Laodelphax striatellus*)

An additional test was carried out with 10 small brown planthoppers by preparing an acetone solution of the testing compound diluted to a predetermined concentration, spraying the solution onto rice seedlings and air drying the rice seedlings. The medicament was all used as received. The rice seedlings were placed in a constant-temperature room at 25° C., and the survival rate was investigated after 6 days. The test was carried out by means of one group of 10 pests. As a result, Compound Nos. 44, 47, 49, 51, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 113, 115, 116, 117, 118, and 119 exhibited an pesticidal rate of 70% or more at a concentration of 100 ppm.

The invention claimed is:

1. A method for control of an ectoparasite on an animal, comprising systemically applying a compound represented by the following Formula (2):

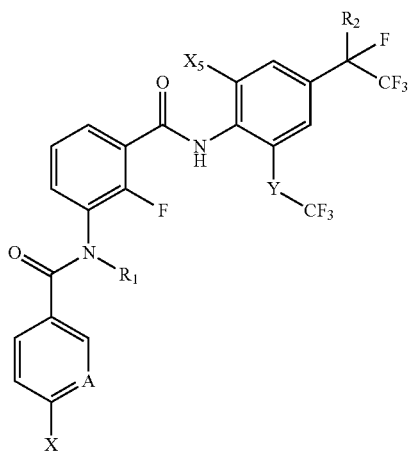

(2)

wherein:

$R_1$ represents a hydrogen atom or a $C_1$-$C_4$ alkyl group;

$R_2$ represents a trifluoromethyl group or a pentafluoroethyl group;

X represents a difluoromethyl group;

$X_5$ represents a bromine atom or an iodine atom;

A represents a nitrogen atom; and

Y represents a single bond, wherein the ectoparasite includes *Ctenocephalides felis*.

2. The method according to claim 1, wherein the compound is one selected from a group consisting of Compound Nos. 85 and 87 represented by the following structures,

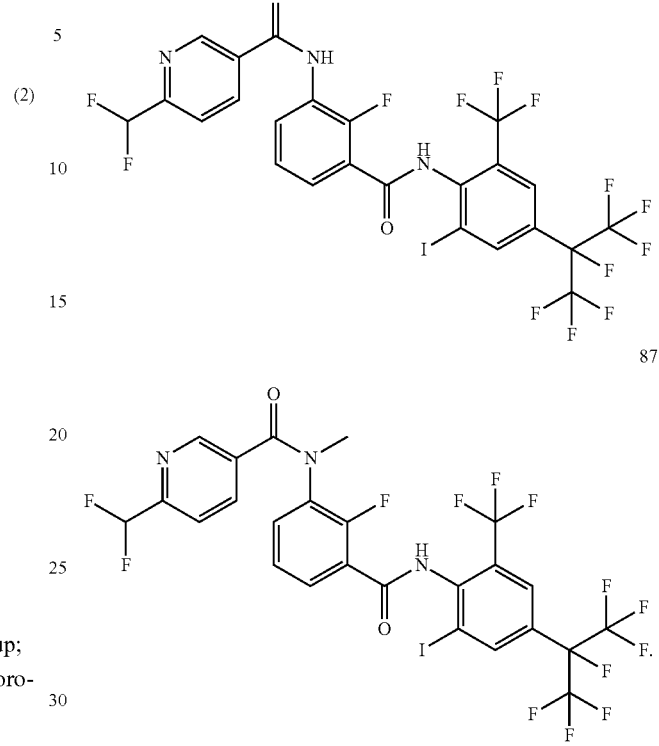

3. The method according to claim 1, comprising systemically applying the compound via at least one of an oral route, a parenteral route, or a dermal route.

4. The method according to claim 2, comprising systemically applying the compound via at least one of an oral route, a parenteral route, or a dermal route.

* * * * *